US009695438B2

(12) United States Patent
Pozniak et al.

(10) Patent No.: US 9,695,438 B2
(45) Date of Patent: *Jul. 4, 2017

(54) WHEAT PLANTS HAVING INCREASED RESISTANCE TO IMIDAZOLINONE HERBICIDES

(71) Applicant: University of Saskatchewan, Saskatoon (CA)

(72) Inventors: Curtis J. Pozniak, Saskatoon (CA); Pierre Hucl, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/284,730

(22) Filed: Oct. 4, 2016

(65) Prior Publication Data
US 2017/0022514 A1    Jan. 26, 2017

Related U.S. Application Data

(62) Division of application No. 13/366,932, filed on Feb. 6, 2012, which is a division of application No. 12/363,087, filed on Jan. 30, 2009, now Pat. No. 8,110,727, which is a division of application No. 10/486,605, filed as application No. PCT/CA02/01051 on Jul. 10, 2002, now Pat. No. 7,897,845.

(60) Provisional application No. 60/311,282, filed on Aug. 9, 2001.

(51) Int. Cl.
*A01H 5/10* (2006.01)
*C12N 15/82* (2006.01)
*C12Q 1/68* (2006.01)
*C12N 9/88* (2006.01)
*A01N 43/50* (2006.01)

(52) U.S. Cl.
CPC .......... *C12N 15/8274* (2013.01); *A01H 5/10* (2013.01); *A01N 43/50* (2013.01); *C12N 9/88* (2013.01); *C12N 15/8278* (2013.01); *C12Q 1/6895* (2013.01); *C12Y 401/03* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 4,761,373 A | 8/1988 | Anderson et al. |
| 5,013,659 A | 5/1991 | Bedbrook et al. |
| 5,304,732 A | 4/1994 | Anderson et al. |
| 5,331,107 A | 7/1994 | Anderson et al. |
| 5,731,180 A | 3/1998 | Dietrich |
| 5,767,361 A | 6/1998 | Dietrich |
| 5,853,973 A | 12/1998 | Kakefuda et al. |
| 5,928,937 A | 7/1999 | Kakefuda et al. |
| 6,211,438 B1 | 4/2001 | Anderson et al. |
| 6,211,439 B1 | 4/2001 | Anderson et al. |
| 6,222,100 B1 | 4/2001 | Anderson et al. |
| 6,225,105 B1 | 5/2001 | Sathasivan et al. |
| 6,339,184 B1 | 1/2002 | Smith |
| 6,613,963 B1 | 9/2003 | Gingera et al. |
| 6,696,294 B1 | 2/2004 | Konzak |
| 7,897,845 B2 | 3/2011 | Pozniak et al. |
| 8,110,727 B2 | 2/2012 | Pozniak et al. |

FOREIGN PATENT DOCUMENTS

| EP | 0360750 A2 | 3/1990 |
| EP | 0375875 | 7/1990 |
| EP | 0508161 A1 | 10/1992 |
| EP | 0525384 A2 | 2/1993 |
| WO | WO90/14000 A1 | 11/1990 |
| WO | WO00/53763 | 9/2000 |
| WO | WO0192512 A2 | 6/2001 |
| WO | WO02/092820 A1 | 11/2002 |
| WO | WO03/013225 A2 | 2/2003 |
| WO | WO03/014356 A2 | 2/2003 |

OTHER PUBLICATIONS

Newhouse et al 1992, Plant Physiology 100: 882-886.*
Seefeldt et al 1998, Weed Science 46: 632-634.*
Feldman et al., "Rapid Elimination of Low-Copy DNA Sequences in Polyploid Wheat: A Possible Mechanism for Differentiation of Homoeologous Chromosomes", Genetics,147:1381-1387 (1997).
Seefeldt et al., "Production of Herbicide-Resistant Jointed Goatgrass (Aegilops cylindrical) x Wheat (Triticum aestivum) Hybrids in the field by Natural Hybridization", Weed Science, 46:632-634 (1998).
J. Andrew Kendig and M.S. DeFelice, "ALS Resistance Cocklebur (Xanthium strumarium L.) in Missouri", WSSA Abstracts, vol. 34, Feb. 7-10, 1994, 1994 Meeting of the Weed Science Society of America.
Barrett, M., "Protection of Grass Crops from Sulfonylurea and Imidazolinone Toxicity," Crop Safeners for Herbicides, 1989, pp. 195-220, Academic Press, Inc.
Bernasconi, P., et al., "A Naturally Occurring Point Mutation Confers Broad Range Tolerance to Herbicides That Target Acetolactate Synthase," The Journal of Biological Chemistry, 1995, pp. 17381-17385, vol. 270(29).
Brown, M., et al., "Hydrolytic Activation versus Oxidative Degradation of Assert Herbicide, an Imidazolinone Aryl-carboxylate, in Susceptible Wild Oat versus Tolerant Corn and Wheat," Pesticide Biochemistry and Physiology, 1987, pp. 24-29, vol. 27, Academic Press, Inc.

(Continued)

*Primary Examiner* — David H Kruse
(74) *Attorney, Agent, or Firm* — Mintz, Levin, Cohn, Ferris, Glovsky and Popeo P.C.

(57) ABSTRACT

The present invention is directed to wheat plants having increased resistance to an imidazolinone herbicide. More particularly, the present invention includes wheat plants containing one or more IMI nucleic acids such as a Teal IMI cultivar. The nucleic acids are preferably located on or derived from different genomes. The present invention also includes seeds produced by these wheat plants and methods of controlling weeds in the vicinity of these wheat plants.

22 Claims, 42 Drawing Sheets

(56) References Cited

OTHER PUBLICATIONS

Chang, A., and R. Duggelby, "Herbicide-resistant Forms of Arabidopsis thaliana Acetohydroxyacid Synthase: Characterization of the Catalytic Properties and Sensitivity to Inhibitors of Four Defined Mutants," Biochemistry 1, 1998, pp. 765-777, vol. 333.
Chong C., and J. Choi, "Amino Acid Residues Conferring Herbicide Tolerance in Tobacco Acetolactate Synthase," Biochemical and Biophysical Research Communications, 2000, pp. 462-467, vol. 279, Academic Press.
Duggleby, R., et al., "Systematic Characterization of Mutations in Yeast Acetohydroxyacid Synthase," Eur. J Biochem., 2003, pp. 2895-2904, vol. 270.
Hattori, J., et al., "Multiple Resistance to Sulfonylureas and Imidazolinones Conferred by an Acetohydroxyacid Synthase Gene with Separate Mutations for Selective Resistance," Molecular Genetics, 1992, pp. 167-173, vol. 232.
Lee, Y., et al., "Effect of Mutagenesis at Serine 653 of Arabidopsis thaliana Acetohydroxyacid Synthase on the Sensitivity to Imidazolinone and Sulfonylurea Herbicides," FEBS Letters, 1999, pp. 341-345, vol. 452, Federation of European Biochemical Societies.
Mourad, G., et al., "Isolation and Genetic Analysis of a Triazolopyrimidine-Resistant Mutant of Arabidopsis," J Heredity, 1993, pp. 91-96, vol. 84.
Newhouse, K., et al., "Mutations in corn (*Zea mays* L.) Conferring Resistance to Imidazolinone Herbicides," Theor. Appl. Genet., 1991, pp. 65-70, vol. 83, Springer-Verlag.
Newhouse, K., et al., "Tolerance to Imidazolinone Herbicides in Wheat," Plant Physiology, 1992, pp. 882-886, vol. 100.
Odell, et al., "Comparison of Increased Expression of Wild-Type and Herbicide Resistant Acetolactate Synthase Genes in Transgenic Plants, and Indication of Posttranscriptional Limitation on Enzyme Activity," Plant Physiol., (1990), pp. 1647-1654, vol. 94.
Ott, K., et al., "Rational Molecular Design and Genetic Engineering of Herbicide Resistant Crops by Structure Modeling and Site-directed Mutagenesis of Acetohydroxyacid Synthase," J Mol. Biol., 1996, pp. 359-368, vol. 263, Academic Press Limited.
Repellin, A., et al., "Genetic Enrichment of Cereal Crops via Alien Gene Transfer: New Challenges," Plant Cell, Tissue and Organ Culture, 2001, pp. 159-183, vol. 64.
Sathasivan, K., et al., "Nucleotide Sequence of a Mutant Acetolactate synthase Gene from an Imidaziolinone-resistant Arabidopsis thaliana var. Columbia," Nucleic Acids Research, 1990, pp. 2188, vol. 18(8), Oxford University Press.
Sathasivan, K., et al., "Molecular Basis of Imidazolinone Herbicide Resistance in Arabidopsis thaliana var Columbia," Plant Physiol., 1991, pp. 1044-1050, vol. 97.
Paul R. Schmitzer et al., "Lack of Cross-Resistance of Imazaquin-Resistant Xanthiu strumarium Acetolactate Synthase to Flumetsulam and Chlorimuron", Plant Physiol., vol. 103, 1993, pp. 281-283.
Sebastian, S., et al., "Semidominant Soybean Mutation for Resistance to Sulfonylurea Herbicides," Crop. Sci., 1989, pp. 1403-1408, vol. 29.
Shaner, D., et al., "Imidazolinone-Resistant Crops: Selection, Characterization, and Management," Herbicide-Resistant Crops: Agricultural, Environmental, Economic, 1996, pp. 143 -157.
Shaner, D. and P.A. Robson, "Absorption, Translocation, and Metabolism of AC 25 214 in Soybean (Glycine max), Common Cocklebur (Xanthium Strumarium), and Velvetlea (Abutilon theophrasti)," Weed Sci., 1985, pp. 469-471, vol. 33.
Shaner, D., et al., "Imidazolinones: Potent Inhibitors of Acetohydroxyacid Synthase," Plant Physiol., 1984, pp. 545-546, vol. 76.
Singh, B.K., "Biosynthesis of Valine, Leucine and Isoleucine," Plant Amino Acids, 1999, pp. 227-247, Marcel Dekker Inc., New York, NY.
Swanson, E., et al., "Microspore Mutagenesis and Selection: Canola Plants with Field Tolerance to the Imidazolinones," Theor. Appl. Genet., 1989, pp. 525-530, vol. 78, Springer-Verlag.
White, A., et al., "Common sunflower resistance to acetolactate synthase-inhibiting herbicides," Weed Science, 2002, pp. 432-437, vol. 50.
Wright, T.R. and D. Penner, "Cell Selection and Inheritance of Imidazolinone Resistance in Sugarbeet (Beta vulgaris)," Theor. Appl. Genet., 1998, pp. 612-620, vol. 96, Springer-Verlag.
GenBank Accession No. BE417248. Created Jul. 24 2000.
GenBank Accession No. BF200418. Created Nov. 6 2000.
EMBL Accession No. AF059600. Created Apr. 27 1998.
Feldman et al., "Genomic asymmetry in allopolyploid plants: wheat as a model", Journal of Experimental Botany, vol. 63, No. 14, pp. 5045-5059 (2012).
Faris et al., "Chromosome Mapping and Phylogenetic Analysis of the Cytosolic Acetyl-CoA Carboxylase Loci in Wheat", Mol. Biol. Evol. 18(9):1720-1733 (2001).
Chantret et al., "Molecular Basis of Evolutionary Events That Shaped the Hardness Locus in Diploid and Polypoid Wheat Species (Triticum and Aegilops)", The Plant Cell, vol. 17, 1033-1045 (Apr. 2005).

\* cited by examiner

Figure 1

| Cross | | Resistant (R) | Intermediate (I) | Susceptible (S) | Total F₁ screened | | |
|---|---|---|---|---|---|---|---|
| | | | | | R | I | S |
| Teal | | 0 | 0 | 334 | - | | |
| 1A | | 59 | 0 | 0 | | | |
| | Teal x 1A | 0 | 5 | 0 | 0 | 10 | 0 |
| | 1A x Teal | 0 | 5 | 0 | | | |
| 9A | | 66 | 0 | 0 | | | |
| | Teal x 9A | 0 | 5 | 0 | 0 | 10 | 0 |
| | 9A x Teal | 0 | 5 | 0 | | | |
| 10A | | 66 | 0 | 0 | | | |
| | Teal x 10A | 0 | 5 | 0 | 0 | 11 | 0 |
| | 10A x Teal | 0 | 6 | 0 | | | |
| 11A | | 53 | 0 | 0 | | | |
| | Teal x 11A | 0 | 7 | 0 | 0 | 15 | 0 |
| | 11A x Teal | 0 | 8 | 0 | | | |
| 15A | | 48 | 0 | 0 | | | |
| | Teal x 15A | 7 | 0 | 0 | 14 | 0 | 0 |
| | 15A x Teal | 7 | 0 | 0 | | | |
| 16A | | 66 | 0 | 0 | | | |
| | Teal x 16A | 0 | 7 | 0 | 0 | 14 | 0 |
| | 16A x Teal | 0 | 7 | 0 | | | |

Figure 2

| Cross | F₂ Generation | | | | | BCF₁ Generation[c] | | | |
|---|---|---|---|---|---|---|---|---|---|
| | Resistant (R) | Susceptible (S) | Ratio tested (R:S) | P Value[a] | Homogeneity of reciprocal crosses[b] | R | S | Ratio tested (R:S)[d] | P Value[e] |
| Teal x 1A | 635 | 201 | 3:1 | 0.55 | 0.49 | 33 | 27 | 1:1 | 0.52 |
| Teal x 9A | 492 | 141 | 3:1 | 0.12 | 0.66 | 42 | 34 | 1:1 | 0.39 |
| Teal x 10A | 701 | 231 | 3:1 | 0.91 | 0.87 | 27 | 20 | 1:1 | 0.38 |
| Teal x 11A | 505 | 189 | 3:1 | 0.19 | 0.32 | 34 | 30 | 1:1 | 0.71 |
| Teal x 15A | 893 | 74 | 15:1 | 0.08 | 0.39 | 45 | 20 | 3:1 | 0.35 |
| Teal x 16A | 587 | 168 | 3:1 | 0.09 | 0.33 | 26 | 23 | 1:1 | 0.78 |

Figure 3

| Cross | Resistant (R) | Segregating (Seg) | Susceptible (S) | Ratio Tested (R:Seg:S)[a] | P Value[b] | Total # Families |
|---|---|---|---|---|---|---|
| Teal x 1A | 12 | 28 | 10 | 1:2:1 | 0.64 | 50 |
| Teal x 9A | 15 | 23 | 12 | 1:2:1 | 0.66 | 50 |
| Teal x 10A | 9 | 27 | 14 | 1:2:1 | 0.52 | 50 |
| Teal x 11A | 14 | 26 | 8 | 1:2:1 | 0.40 | 48 |
| Teal x 15A | 36 | 55 | 9 | 7:8:1 | 0.21 | 100 |
| Teal x 16A | 12 | 25 | 11 | 1:2:1 | 0.94 | 48 |

Figure 4

| Cross | Resistant (R) | Susceptible (S) | Ratio tested (R:S) | P Value[a] |
|---|---|---|---|---|
| 1A x 9A | 506 | 0 | - | - |
| 1A x 10A | 567 | 0 | - | - |
| 1A x 15A | 501 | 0 | - | - |
| 1A x 16A | 814 | 0 | - | - |
| 1A x SWP965001 | 309 | 0 | - | - |
| 9A x 10A | 603 | 0 | - | - |
| 9A x 15A | 424 | 0 | - | - |
| 9A x 16A | 336 | 0 | - | - |
| 9A x SWP965001 | 407 | 0 | - | - |
| 10A x 15A | 547 | 0 | - | - |
| 10A x 16A | 409 | 0 | - | - |
| 10A x SWP965001 | 686 | 0 | - | - |
| 15A x 16A | 298 | 0 | - | - |
| 15A x SWP965001 | 410 | 0 | - | - |
| 16A x SWP965001 | 509 | 0 | - | - |
| SWP965001 x 11A | 688 | 47 | 15:1 | 0.93 |
| 1A x 11A | 735 | 56 | 15:1 | 0.37 |
| 11A x 9A | 446 | 42 | 15:1 | 0.00 |
| 11A x 10A | 557 | 46 | 15:1 | 0.19 |
| 11A x 15A | 600 | 14 | 63:1 | 0.20 |
| 11A x 16A | 390 | 34 | 15:1 | 0.16 |

Figure 5

| Cross | Resistant (R) | Segregating (Seg) | Susceptible (S) | Ratio Tested (R:Seg:S)[a] | P Value[b] | Total # Families |
|---|---|---|---|---|---|---|
| SWP965001 x 11A | 32 | 42 | 7 | 7:8:1 | 0.57 | 81 |
| 1A x 11A | 33 | 58 | 9 | 7:8:1 | 0.07 | 100 |
| 11A x 9A | 36 | 49 | 5 | 7:8:1 | 0.77 | 90 |
| 11A x 10A | 34 | 59 | 7 | 7:8:1 | 0.14 | 100 |
| 11A x 16A | 45 | 47 | 7 | 7:8:1 | 0.86 | 99 |

Figure 6

| Imazamox Conc. (uM) | % Uninhibited AHAS Activity | | | |
|---|---|---|---|---|
| | Teal | 11A | BW755 | 15A |
| 0.8 | 71.1 | 84.8 | 90.0 | 92.6 |
| 1.6 | 55.2 | 71.2 | 76.9 | 88.4 |
| 3.1 | 41.8 | 59.7 | 65.7 | 84.3 |
| 6.3 | 30.9 | 50.3 | 56.6 | 80.3 |
| 12.5 | 22.3 | 42.9 | 49.6 | 76.3 |
| 25.0 | 16.2 | 37.6 | 44.5 | 72.5 |
| 50.0 | 12.6 | 34.3 | 41.4 | 68.8 |
| 100.0 | 11.4 | 33.1 | 40.4 | 65.2 |

Figure 7

| | 10X | | 30X | |
|---|---|---|---|---|
| Genotype | %Injured | %No Injury | %Injured | %No Injury |
| BW755 (one gene) | 100 | 0 | 100 | 0 |
| Teal 15A (two gene) | 0 | 100 | 100 | 0 |
| 15A/11A (three gene) | 33 | 67 | 48 | 52 |

```
         490                 500                         510
          |                   |                           |
    M  G  F  G  L  P  A  A  A  G  A  S  V  A  N  P  G  V  T  V  D  I  D  G  D  G
    ATG GGA TTT GGG CTG CCT GCT GCA GGT GCT TCT GTG GCT AAC CCA GGT GTC ACA GTT GAT ATT GAT GGG GAT GGT

M  G  F  G  L  P  A  A  A  G  A  A  V  A  N  P  G  V  T  V  D  I  D  G  D  G
    ATG GGA TTT GGG TTA CCA GCT GCA GGT GCT GCT GTG GCC AAC CCA GGT GTT ACA GTT GAC ATT GAT GGT GAT GGT

M  G  F  G  L  P  A  A  A  G  A  A  V  A  N  P  G  V  T  V  D  I  D  G  D  G
    ATG GGA TTT GGG TTA CCA GCT GCA GGT GCT GCT GTG GCC AAC CCA GGT GTT ACA GTT GAC ATT GAT GGT GAT GGT

M  G  F  G  L  P  A  A  A  G  A  A  V  A  N  P  G  V  T  V  D  I  D  G  D  G
    ATG GGA TTT GGG TTA CCA GCT GCA GGT GCA GCT GTG GCC AAC CCA GGT GTT ACA GTT GAC ATT GAT GGT GAT GGT

M  G  F  G  L  P  A  A  A  G  A  A  V  A  N  P  G  V  T  V  D  I  D  G  D  G
    ATG GGA TTT GGG TTA CCA GCT GCA GGT GCT GCT GTG GCC AAC CCA GGT GTT ACA GTT GAC ATT GAT GGT GAT GGT

M  G  F  G  L  P  A  A  A  G  A  A  V  A  N  P  G  V  T  V  D  I  D  G  D  G
    ATG GGA TTT GGG TTA CCA GCT GCA GGT GCT GCT GTG GCC AAC CCA GGT GTT ACA GTT GAC ATT GAT GGT GAT GGT

M  G  F  G  L  P  A  A  A  G  A  A  V  A  N  P  G  V  T  V  D  I  D  G  D  G
    ATG GGA TTT GGG TTA CCA GCT GCA GGT GCT GCT GTG GCC AAC CCA GGT GTT ACA GTT GAC ATT GAT GGT GAT GGT 520                 530                         540
          |                   |                           |
    S  F  L  M  N  I  Q  E  L  A  L  I  R  I  E  N  L  P  V  K  V  M  V  L  N  N  Q
    AGC TTC CTC ATG AAC ATT CAG GAG CTG GCA TTG ATC CGC ATT GAG AAC CTC CCT GTG AAG GTG ATG GTG TTG AAC AAC CAA

S  F  L  M  N  I  Q  E  L  A  L  I  R  I  E  N  L  P  V  K  V  M  I  L  N  N  Q
    AGT TTC CTC ATG AAC ATT CAG GAG TTG GCG TTG ATC CGC ATT GAG AAC CTC CCA GTG AAG GTG ATG ATA TTG AAC AAC CAG

S  F  L  M  N  I  Q  E  L  A  L  I  R  I  E  N  L  P  V  K  V  M  I  L  N  N  Q
    AGT TTC CTC ATG AAC ATT CAG GAG TTG GCG TTG ATC CGC ATT GAG AAC CTC CCA GTG AAG GTG ATG ATA TTG AAC AAC CAG

S  F  L  M  N  I  Q  E  L  A  L  I  R  I  E  N  L  P  V  K  V  M  I  L  N  N  Q
    AGT TTC CTC ATG AAC ATT CAG GAG TTG GCG TTG ATC CGC ATT GAG AAC CTC CCA GTG AAG GTG ATG ATA TTG AAC AAC CAG

S  F  L  M  N  I  Q  E  L  A  L  I  R  I  E  N  L  P  V  K  V  M  I  L  N  N  Q
    AGT TTC CTC ATG AAC ATT CAG GAG TTG GCG TTG ATC CGC ATT GAG AAC CTC CCA GTG AAG GTG ATG ATA TTG AAC AAC CAG

S  F  L  M  N  I  Q  E  L  A  L  I  R  I  E  N  L  P  V  K  V  M  I  L  N  N  Q
    AGT TTC CTC ATG AAC ATT CAG GAG TTG GCG TTG ATC CGC ATT GAG AAC CTC CCA GTG AAG GTG ATG ATA TTG AAC AAC CAG

S  F  L  M  N  I  Q  E  L  A  L  I  R  I  E  N  L  P  V  K  V  M  I  L  N  N  Q
    AGT TTC CTC ATG AAC ATT CAG GAG TTG GCG TTG ATC CGC ATT GAG AAC CTC CCA GTG AAG GTG ATG ATA TTG AAC AAC CAG
```

| | | | | | | | | | | 10 | | | | | | | | | | 20 | | | | | | | | SEQ ID NO: |
|---|---|---|---|---|---|---|---|---|---|---|---|---|---|---|---|---|---|---|---|---|---|---|---|---|---|---|---|---|
| M | A | T | T | A | A | A | A | A | A | A | A | L | S | A | A | A | T | A | K | T | G | R | K | N | H | Q | R | 14 |
| ATG | GCT | ACG | ACC | GCC | GCG | GCC | GCC | GCC | GCC | GCC | CTG | TCC | GCC | GCG | ACG | GCC | AAG | ACC | GGC | CGT | AAG | AAC | CAC | CAG | CGA | | | 13 |
| V | | | | | | | | | | | | | | | | | | | | | | | | | | | X | 26 |
| GT- | | | | | | | | | | | | | | | | | | | | | | | | | | | | 25 |
| V | | | | | | | | | | | | | | | | | | | | | | | | | | | X | 28 |
| GT- | | | | | | | | | | | | | | | | | | | | | | | | | | | | 27 |
| V | | | | | | | | | | | | | | | | | | | | | | | | | | | X | 30 |
| GT- | | | | | | | | | | | | | | | | | | | | | | | | | | | | 29 |
| V | | | | | | | | | | | | | | | | | | | | | | | | | | | X | 32 |
| GT- | | | | | | | | | | | | | | | | | | | | | | | | | | | | 31 |
| V | | | | | | | | | | | | | | | | | | | | | | | | | | | X | 34 |
| GT- | | | | | | | | | | | | | | | | | | | | | | | | | | | | 33 |

| | | | | 30 | | | | | | | | | | 40 | | | | | | | | | 50 | | | | | SEQ ID NO: |
|---|---|---|---|---|---|---|---|---|---|---|---|---|---|---|---|---|---|---|---|---|---|---|---|---|---|---|---|---|
| H | H | V | L | P | A | R | G | V | G | A | A | A | V | R | C | S | A | V | S | P | R | T | P | P | S | | | 14 |
| CAC | CAC | GTC | CTT | CCC | GCT | CGA | GGC | GTG | GGG | GCG | GCG | GCG | GTC | AGG | TGC | TCG | GCG | GTG | TCC | CCG | GTC | ACC | CCG | CCG | TCC | | | 13 |
| X | | | | | | | | | | | | | | | | | | | | | | | | | | | | 26 |
| | | | | | | | | | | | | | | | | | | | | | | | | | | | | 25 |
| X | | | | | | | | | | | | | | | | | | | | | | | | | | | | 28 |
| | | | | | | | | | | | | | | | | | | | | | | | | | | | | 27 |
| X | | | | | | | | | | | | | | | | | | | | | | | | | | | | 30 |
| | | | | | | | | | | | | | | | | | | | | | | | | | | | | 29 |
| X | | | | | | | | | | | | | | | | | | | | | | | | | | | | 32 |
| | | | | | | | | | | | | | | | | | | | | | | | | | | | | 31 |
| X | | | | | | | | | | | | | | | | | | | | | | | | | | | | 34 |
| | | | | | | | | | | | | | | | | | | | | | | | | | | | | 33 |

```
         220                                                  230                                                  240
   ----+----|----+----|----+----|----+----|----+----|----+----|----+----|----+----|----+----|----+----|
    S  G  R  P  G  P  V  L  V  D  I  P  K  D  I  Q  Q  M  A  V  P  V  W  D  T
   TCC GGC CGT CCT GGC CCG GTG CTG GTC GAC ATC CCC AAG GAC ATC CAG CAG ATG GCC GTG CCG GTC TGG GAC ACC

S  G  R  P  G  P  V  L  V  D  I  P  K  D  I  Q  Q  M  A  V  P  V  W  D  T
   TCC GGC CGC CCG GGG CCG GTG CTG GTT GAT ATC CCC AAG GAC ATC CAG CAG ATG GCT GTG CCT GTC TGG GAC ACG

S  G  R  P  G  P  V  L  V  D  I  P  K  D  I  Q  Q  M  A  V  P  V  W  D  T
   TCC GGC CGC CCG GGG CCG GTG CTG GTT GAT ATC CCC AAG GAC ATC CAG CAG ATG GCT GTG CCT GTC TGG GAC ACG

S  G  R  P  G  P  V  L  V  D  I  P  K  D  I  Q  Q  M  A  V  P  V  W  D  T
   TCC GGC CGC CCG GGG CCG GTG CTG GTT GAT ATC CCC AAG GAC ATC CAG CAG ATG GCT GTG CCT GTC TGG GAC ACG

S  G  R  P  G  P  V  L  V  D  I  P  K  D  I  Q  Q  M  A  V  P  V  W  D  T
   TCC GGC CGC CCG GGG CCG GTG CTG GTT GAT ATC CCC AAG GAC ATC CAG CAG ATG GCT GTG CCT GTC TGG GAC ACG

S  G  R  P  G  P  V  L  V  D  I  P  K  D  I  Q  Q  M  A  V  P  V  W  D  T
   TCC GGC CGC CCG GGG CCG GTG CTG GTT GAT ATC CCC AAG GAC ATC CAG CAG ATG GCT GTG CCT GTC TGG GAC ACG 250                                                  260                                                  270
   ----+----|----+----|----+----|----+----|----+----|----+----|----+----|----+----|----+----|----+----|
    G  M  N  L  P  G  Y  I  A  R  L  D  L  P  K  P  A  T  E  S  L  E  Q  V  L  R  L  V
   TCG ATG AAT CTA CCA GGG TAC ATC GCA CGC CTG GAC CTG CCC AAG CCA GCG ACA GAA TCG CTT GAG CAG GTC TTG CGT CTG GTT

P  M  S  L  P  G  Y  I  A  R  L  D  L  P  K  P  S  T  E  S  L  E  Q  V  L  R  L  V
   CCG ATG AGT TTG CCA GGG TAC ATC GCC CGC CGC CTG CCC AAG CCA TCT ACT GAA TCG CTT GAG CAG GTC CGT CTG GTT

P  M  S  L  P  G  Y  I  A  R  L  D  L  P  K  P  S  T  E  S  L  E  Q  V  L  R  L  V
   CCG ATG AGT TTG CCA GGG TAC ATC GCC CGC CGC CTG CCC AAG CCA TCT ACT GAA TCG CTT GAG CAG GTC CGT CTG GTT

P  M  S  L  P  G  Y  I  A  R  L  D  L  P  K  P  S  T  E  S  L  E  Q  V  L  R  L  V
   CCG ATG AGT TTG CCA GGG TAC ATC GCC CGC CGC CTG CCC AAG CCA TCT ACT GAA TCG CTT GAG CAG GTC CGT CTG GTT

P  M  S  L  P  G  Y  I  A  R  L  D  L  P  K  P  S  T  E  S  L  E  Q  V  L  R  L  V
   CCG ATG AGT TTG CCA GGG TAC ATC GCC CGC CGC CTG CCC AAG CCA TCT ACT GAA TCG CTT GAG CAG GTC CGT CTG GTT

P  M  S  L  P  G  Y  I  A  R  L  D  L  P  K  P  S  T  E  S  L  E  Q  V  L  R  L  V
   CCG ATG AGT TTG CCA GGG TAC ATC GCC CGC CGC CTG CCC AAG CCA TCT ACT GAA TCG CTT GAG CAG GTC CGT CTG GTT
```

```
                              330                    340                    350
                       --------+---------+---------+---------+---------+---------
     M  H  G  T  V  Y  A  N  Y  A  V  D  K  A  D  L  L  L  A  F  G  V  R  F  D  D  R
     ATG CAT GGC ACG GTG TAC GCA AAT TAT GCC GTG GAT AAG GCT GAC CTG TTG CTT GCG TTT GGT GTG CGG TTT GAT GAT CGT

M  H  G  T  V  Y  A  N  Y  A  V  D  K  A  D  L  L  L  A  F  G  V  R  F  D  D  R
     ATG CAT GGC ACT GTG TAT GCA AAT TAT GCA GTA GAT AAG GCT GAC CTG TTG CTT NTT GCA TTT GGT GTG CGG TTT GAT GAT CGT

M  H  G  T  V  Y  A  N  Y  A  V  D  K  A  D  L  L  L  A  F  G  V  R  F  D  D  R
     ATG CAT GGC ACT GTG TAT GCA AAT TAT GCA GTA GAT AAG GCT GAC CTG TTG CTT GCA TTT GGT GTG CGG TTT GAT GAT CGT

M  H  G  T  V  Y  A  N  Y  A  V  D  K  A  D  L  L  L  A  F  G  V  Q  F  D  D  R
     ATG CAT GGC ACT GTG TAT GCA AAT TAT GCA GTA GAT AAG GCT GAC CTG TTG CTT GCA TTT GGT GTG CNG GTT GAT GAT CGT

M  H  G  T  V  Y  A  N  Y  A  V  D  K  A  D  L  L  L  A  F  G  V  R  F  D  D  R
     ATG CAT GGC ACT GTG TAT GCA AAT TAT GCA GTA GAT AAG GCT GAC CTG TTG CTT GCA TTT GGT GTG CGG TTT GAT GAT CGT

M  H  G  T  V  Y  A  N  Y  A  V  D  K  A  D  L  L  L  A  F  G  V  R  F  D  D  R
     ATG CAT GGN ACT GTG TAT GCA AAT TAT GCA GTA GAT AAG GCT GAC CTG TTG CTT GCA TTT GGT GTG CGG TTT GAT GAT CGT 360                    370
                       --------+---------+---------+---------+---------+---------
     V  T  G  K  I  E  A  F  A  S  R  D  K  A  I  V  H  I  D  I  D  P  A  E  I  G  K  N
     GTG ACA GGG AAA ATT GAG GCT TTT GCA AGC AGG GAT AAG GCC ATT GTG CAC ATT GAC ATT GAT CCA GCA GAG ATT GCA AAG AAC

V  T  G  K  I  E  A  F  A  S  R  D  K  A  I  V  H  I  D  I  D  P  A  E  I  G  K  N
     GTG ACC GGG AAA ATC GAG GCT TTT GCA AGC AGG GAT AAG GCC ATT GTG CAC ATT GAC ATT GAC CCA GCT GAG ATT GGC AAG AAC

V  I  G  K  I  E  A  F  A  S  R  D  K  A  I  V  H  I  D  I  D  P  A  E  I  G  K  N
     GTG ACC GGG AAA ATC GAG GCT TTT GCA AGC AGG GAT AAG GCC ATT GTG CAC ATT GAC ATT GAC CCA GCT GAG ATT GGC AAG AAC

V  N  G  K  I  E  A  F  A  S  R  D  K  A  I  E  H  I  D  I  D  P  A  E  I  G  K  N
     GTG ANC GGG AAA ATC GAN GCT TTT GCA AGC AGG GAT AAG GCC ATT GNG CAC ATT GAC ATT GAC CCA GCT GAG ATT GGC AAG AAC

V  T  G  K  I  E  A  F  A  S  R  D  K  A  I  V  H  I  D  I  D  P  A  E  I  G  K  N
     GTG ACC GGG AAA ATC GAG GCT TTT GCA AGC AGG GAT AAG GCC ATT GTG CAC ATT GAC ATT GAC CCA GCT GAG ATT GGC AAG AAC

V  T  G  K  I  E  A  F  A  S  R  D  K  A  I  V  H  I  D  I  D  P  A  E  I  G  K  N
     GTG ACC GGG AAA ATC GAG GCT TTT GCA AGC AGG GAT AAG GCC ATT GTG CAC ATT GAC ATT GAC CCA GCT GAG ATT GGC AAG AAC
```

Figure 9 Continued

```
           380                390                400                                430
             |                  |                  |                                  |
  K   Q   P   H   V   S   I   C   A   D   V   K   L   A   L   Q   G   L   N   A   L   L   Q   S   T   T
AAG CAA CCA CAT GTG TCA ATT TGC GCA GAT GTT AAG CTT GCT TTA CAG GGC TTG AAT GCT CTG CTA CAA AGC ACA ACA

K   Q   P   H   V   S   I   C   A   D   V   K   L   A   L   Q   G   L   N   A   L   L   N   G   S   K   A
AAG CAG CCA CAT GTC TCC ATT TGT GCA GAT GTT AAG CTT GCT TTA CAG GGG TTG AAT GCT CTA TTA AAT GGG AGC AAA GCA

K   Q   P   H   V   S   I   C   A   D   V   K   L   A   L   Q   G   L   N   A   L   L   N   G   S   K   A
AAG CAG CCA CAT GTC TCC ATT TGT GCA GAT GTT AAG CTT GCT TTA CAG GGG TTG AAT GCT CTA TTA AAT GGG AGC AAA GCA

K   Q   P   H   V   S   I   C   A   D   V   K   L   A   L   Q   G   L   N   A   L   L   N   G   S   K   A
AAG CAG CCA CAT GTC TCC ATT TGT GCA GAT GTT AAG CTT GCT TTA CAG GGG TTG AAT GCT CTA TTA AAT GGG AGC AAA GCA

K   Q   P   H   V   S   I   C   A   D   V   K   L   A   L   Q   G   L   N   A   L   L   N   G   S   K   A
AAG CAG CCA CNT GTC TCC ATT TGT GCA GAT GTT AAN CTT GCT TTA CAG GGG TTG AAT GCN CTA TTA AAT GGG AGC AAA GCA

K   Q   P   H   V   S   I   C   A   D   V   K   L   A   L   Q   G   L   N   A   L   L   N   G   S   K   A
AAG CAG CCA CAT GTC TCC ATT TGT GCA GAT GTT AAG CTT GCT TTA CAG GGG TTG AAT GCT CTA TTA AAT GGG AGC AAA GCA

K   Q   P   H   V   S   I   C   A   D   V   K   L   A   L   Q   G   L   N   A   L   L   N   G   S   K   A
AAG CAG CCA CAT GTC TCC ATT TGT GCA GAT GTT AAG CTT GCT TTA CAG GGG TTG AAT GCT CTA TTA AAT GGG AGC AAA GCA 410                                  420
                               |                                    |
  K   T   S   F   S   A   W   H   N   E   L   D   Q   Q   K   R   E   E   F   P   L   G   Y   K   T   F
AAG ACA TCT GAT TTT AGT GCA TGG CAC AAT GAG TTG GAC CAG CAG AAG AGG GAG TTT CCT CTG GGG TAC AAA ACT TTT

Q   Q   G   L   D   F   G   P   W   H   K   E   L   D   Q   Q   K   R   E   E   F   P   L   G   F   K   T   F
CAG CAG GGT CTG GAT TTT GGT CCA TGG CAC AAG GAG TTG GAT CAG CAG AAG AGG GAG TTT CCT CTA GGA TTC AAG ACT TTT

Q   Q   G   L   D   F   G   P   W   H   K   E   L   D   Q   Q   K   R   E   E   F   P   L   G   F   K   T   F
CAA CAG GGT CTG GAT TTT GGT CCA TGG CAC AAG GAG TTG GAT CAG CAG AAG AGG GAG TTT CCT CTA GGA TTC AAG ACT TTT

Q   Q   G   L   D   F   G   P   W   H   K   E   L   D   Q   Q   K   R   E   E   F   P   L   G   F   K   T   F
CAA CAG GGN CTG GAT TTT GGT CCA TGG CNC AAG GAG TTG GAT CAG CAG AAG ANG GAG TTT CCT CTA GGA TTC AAG AAN ACT TTT

Q   Q   G   L   D   F   G   P   W   H   K   E   L   D   Q   Q   K   R   E   E   F   P   L   G   F   K   T   F
CAA CAG GGT CTG GAT TTT GGT CCA TGG CAC AAG GAG TTG GAT CAG CAG AAG AGG GAG TTT CCT CTA GGA TTC AAG ACT TTT

Q   Q   G   L   D   F   G   P   W   H   K   E   L   D   Q   Q   K   R   E   E   F   P   L   G   F   K   T   F
CAA CAG GGT CTG GAT TTT GGT CCA TGG CAC AAG GAG TTG GAT CAG CAG AAG AGG GAG TTT CCT CTA GGA TTC AAG ACT TTT

Q   Q   G   L   D   F   G   P   W   H   K   E   L   D   Q   Q   K   R   E   E   F   P   L   G   F   K   T   F
CAA CAG GGT CTG GAT TTT GGT CCA TGG CAC AAG GAG TTG GAT CAG CAG AAG AGG GAG TTT CCT CTA GGA TTC AAG ACT TTT
```

```
              490                 500                 510                 
                +                   +                   +                   
     M   G   F   G   L   P   A   A   A   S   V   A   N   P   G   V   T   V   V   D   I   D   G   D   G
     ATG GGA TTT GGG CTG CCT GCT GCA GCT TCT GTG GCT AAC CCA GGT GTC ACA GTT GTT GAT ATT GAT GGG GAT GGT

M   G   F   G   L   P   A   A   A   A   V   A   N   P   G   V   T   V   V   D   I   D   G   D   G
     ATG GGA TTT GGG TTG CCA GCT GCA GCT GCC GTG GCC AAC CCA GGT GTT ACA GTT GTT GAC ATT GAT GGG GAT GGT

M   G   F   G   L   P   A   A   A   A   V   A   N   P   G   V   T   V   V   D   I   D   G   D   G
     ATG GGA TTT GGG TTG CCA GCT GCA GCT GCC GTG GCC AAC CCA GGT GTT ACA GTT GTT GAC ATT GAT GGG GAT GGT

M   G   F   G   L   P   A   A   A   A   V   A   N   P   G   V   T   V   V   D   I   D   G   D   G
     ATG GGA TTT GGG TTG CCA GCT GCA GCT GCC GTG GCC AAC CCA GGT GTT ACA GTT GTT GAC ATT GAT GGG GAT GGT

M   G   F   G   L   P   A   A   A   G   X   G   N   P   G   V   T   V   V   D   I   D   G   D   G
     ATG GGA TTT GGG TTG CCA GCT GCA GCT GGC -CT GGC AAC CCA GGT GTT ACA GTT GTT GAC ATT GAT GGG GAT GGT

M   G   F   G   L   P   A   A   A   A   V   A   N   P   G   V   T   V   V   D   I   D   G   D   G
     ATG GGA TTT GGG TTG CCA GCT GCA GCT ·A GTG GCC AAC CCA GGT GTT ACA GTT GTT GAC ATT GAT GGG GAT GGT

M   G   F   G   L   P   A   A   A   A   V   A   N   P   G   V   T   V   V   D   I   D   G   D   G
     ATG GGA TTT GGG TTG CCA GCT GCA GCT GCC GTG GCC AAC CCA GGT GTT ACA GTT GTT GAC ATT GAT GGG GAT GGT 520                 530                 540
                +                   +                   +
     S   F   L   M   N   I   Q   E   L   A   L   H   R   I   E   N   L   P   V   T   V   V   M   V   K   V   P   L   N   Q
     AGC TTC CTC ATG AAC ATT CAG GAG CTG GCA TTG ATC CGC ATT GAG AAC CTC CCT GTG AAG GTG ATG GTG AAA CAA

S   F   L   M   N   I   Q   E   L   A   L   R   I   E   N   L   P   V   K   V   M   I   L   N   Q
     AGT TTC CTC ATG AAC ATT CAG GAG TTG GCG TTG ATC CGT ATT GAG AAC CTC CCA GTG AAG GTG ATG ATA TTG AAC CAA

S   F   L   M   N   I   Q   E   L   A   L   R   I   E   N   L   P   V   K   V   M   I   L   N   Q
     AGT TTC CTC ATG AAC ATT CAG GAG TTG GCG TTG ATC CGT ATT GAG AAC CTC CCA GTG AAG GTG ATG ATA TTG AAC CAG

S   F   L   M   N   I   Q   E   L   A   L   R   I   E   N   L   P   V   K   V   M   I   L   N   Q
     AGT TTC CTC ATG AAC ATT CAG GAG TTG GCG TTG ATC CGT ATT GAG AAC CTC CCA GTG AAG GTG ATG ATA TTG AAC CAG

S   F   L   M   N   I   Q   E   L   A   L   R   I   E   N   L   P   V   K   V   M   I   L   N   Q
     AGT TTC CTC ATG AAC ATT CAG GAG TTG GCG TTG ATC CGT ATT GAG AAC CTC CCA GTG AAG GTG ATG ATA TTG AAC CAG

S   F   L   M   N   I   Q   E   L   A   L   R   I   E   N   L   P   V   K   V   M   I   L   N   Q
     AGT TTC CTC ATG AAC ATT CAG GAG TTG GCG TTG ATC CGT ATT GAG AAC CTC CCA GTG AAG GTG ATG ATA TTG AAC CAG

S   F   L   M   N   I   Q   E   L   A   L   R   I   E   N   L   P   V   K   V   M   I   L   N   Q
     AGT TTC CTC ATG AAC ATT CAG GAG TTG GCG TTG ATC CGT ATT GAG AAC CTC CCA GTG AAG GTG ATG ATA TTG AAC CAG
```

Figure 9 Continued

```
                    550                                        560
        ----+----|----+----|----+----|----+----|----+----|----+----|
      H  L  G  M  V  Q  W  E  D  R  F  Y  K  A  N  R  A  H  T  Y  L  G  N  P  E  C
      CAT TTG GGT ATG GTG CAA TGG GAG GAT AGG TTT TAC AAG GCG AAT AGG GCG CAT ACA TAC TTG GGC AAC CCG GAA TGT

H  L  G  M  V  Q  W  E  D  R  F  Y  K  A  N  R  A  H  T  Y  L  G  N  P  E  N
      CAT CTG GGA ATG GTG CAG TGG GAG GAT AGG TTT TAC AAG GCC AAC CGG GCG CAC ACA TAC CTT GGC AAC CCA GAA AAT

H  L  G  M  V  Q  W  E  D  R  F  Y  K  A  N  R  A  H  T  Y  L  G  N  P  E  N
      CAT CTG GGA ATG GTG CAG TGG GAG GAT AGG TTT TAC AAG GCC AAC CGG GCG CAC ACA TAC CTT GGC AAC CCA GAA AAT

H  L  G  M  V  Q  W  E  D  R  F  Y  K  A  N  R  A  H  T  Y  L  G  N  P  E  N
      CAT CTG GGA ATG GTG CAG TGG GAG GAT AGG TTT TAC AAG GCC AAC CGG GCG CAC ACA TAC CTT GGC AAC CCA GAA AAT

H  L  G  M  V  Q  W  E  D  R  F  Y  K  A  N  R  A  H  T  Y  L  G  N  P  E  N
      CAT CTG GGA ATG GTG CAG TGG GAG GAT AGG TTT TAC AAG GCC AAC CGG GCG CAC ACA TAC CTT GGC AAC CCA GAA AAT

H  L  G  M  V  Q  W  E  D  R  F  Y  K  A  N  R  A  H  T  Y  L  G  N  P  E  N
      CAT CTG GGA ATG GTG CAG TGG GAG GAT AGG TTT TAC AAG GCC AAC CGG GCG CAC ACA TAC CTT GGC AAC CCA GAA AAT 570                                        580                                590
        ----+----|----+----|----+----|----+----|----+----|----+----|----+----|----+----|----+----|----+----|
      E  S  I  Y  P  D  F  V  T  I  A  K  G  F  N  I  P  A  V  R  V  T  K  K  S  E
      GAG AGC ATA TAT CCA GAT TTT GTG ACT ATT GCT AAG GGG TTC AAT ATT CCT GCA GTC CGT GTA ACA AAG AAG AGT GAA

E  S  I  Y  P  D  F  V  T  I  A  K  G  F  N  V  P  A  V  R  V  T  K  K  S  E
      GAG AGT ATA TAT CCA GAT TTT GTG ACG ATT GCT AAA GGA TTC AAC GTT CCG GCA GTT CGT GTG ACG AAG AAG AGC GAA

E  S  I  Y  P  D  F  V  T  I  A  K  G  F  N  V  P  A  V  R  V  T  K  K  S  E
      GAG AGT ATA TAT CCA GAT TTT GTG ACG ATT GCT AAA GGA TTC AAC GTT CCG GCA GTT CGT GTG ACG AAG AAG AGC GAA

E  S  I  Y  P  D  F  V  T  I  A  K  G  F  N  V  P  A  V  R  V  T  K  K  S  E
      GAG AGT ATA TAT CCA GAT TTT GTG ACG ATT GCT AAA GGA TTC AAC GTT CCG GCA GTT CGT GTG ACG AAG AAG AGC GAA

E  S  I  Y  P  D  F  V  T  I  A  K  G  F  N  V  P  A  V  R  V  T  K  K  S  E
      GAG AGT ATA TAT CCA GAT TTT GTG ACG ATT GCT AAA GGA TTC AAC GTT CCG GCA GTT CGT GTG ACG AAG AAG AGC GAA

E  S  I  Y  P  D  F  V  T  I  A  K  G  F  N  V  P  A  V  R  V  T  K  K  S  E
      GAG AGT ATA TAT CCA GAT TTT GTG ACG ATT GCT AAA GGA TTC AAC GTT CCG GCA GTT CGT GTG ACG AAG AAG AGC GAA
```

Partial DNA sequence and deduced amino acid sequence of TeaIIMI1 15A

SEQ ID NO:2
SEQ ID NO:1

```
      D   V   F   A   Y   P   G   E   A   S   M   I   H   Q   A   L   T   R   S   P
  C  GAC GTC TTC GCC TAC CCC GGC GAG GCC TCC ATG ATC CAC CAG GCG CTG ACG CGC TCG CCC

V   I   T   N   H   L   F   R   H   E   Q   G   E   A   F   A   A   S   M   B   I   H   Q   A   L   T   R   S   P
 GTC ATC ACC AAC CAC CTC TTC CGC CAC GAG CAG GGG GAG GCG TTC GCG GCG TCC ATG GAG ATC CAC CAG GCG CTG ACG CGC TCG CCC

C   V   A   T   S   G   P   G   A   T   N   L   V   S   A   L   L   D   S   I   P
 GGC GTC TGC GTC GCC ACC TCC GGC CCG GGG GCC ACC AAC CTC GTC TCC GCG CTC CTC GAC TCC ATC CCC

M   V   A   I   T   G   Q   V   P   R   M   R   I   G   T   D   A   F   Q   E   T   P   I   V   E   V   T
 ATG GTC GCC ATC ACG GGC CAG GTC CCC CGC ATG CGC ATC GGC ACG GAC GCG TTC CAG GAG ACG CCC ATA GTG GAG GTC ACG

R   S   I   T   K   H   N   Y   L   V   L   D   V   E   D   I   P   R   V   I   Q   E   A   F   F   L   A
 CGC TCC ATC ACC AAG CAC AAC TAC CTG GTC CTT GAC GTG GAG GAT ATC CCC CGC GTC ATC CAG GAA GCC TTC TTC CTT GCA

S   G   R   P   G   P   V   L   V   D   Y   I   P   K   P   Q   Q   M   A   V   P   V   W   D   T
 TCC GGC CGC CCG GGG CCG GTG CTA GTT GAT ATC AAG CCC CAG CAG ATG GCT GTG CCC GTC TGG GAC ACT

P   M   S   L   P   G   Y   I   A   R   L   Y   G   V   L   E   Q   V   L   R   L   V
 CCA ATG AGT TTG CCA GGG TAC ATC GCC CGC CTG GGT GTT GAG CAG CAG GTC CTG CGT CTG GTT

G   E   S   R   R   P   P   I   L   Y   G   C   A   A   S   G   E   E   L   R   R   F   V   E   L
 GGG GAG TCA CGG CGC CCA ATT CTG TAT GTT GGT GCG TCT GCT GAG GAG TTG CGC CGC TTT GTT GAG CTT

T   G   I   P   V   T   T   T   L   M   G   L   M   G   N   F   P   S   D   P   L   S   R   M   L   G
 ACT GGG ATT CCA GTT ACA ACT ACT CTG ATG GGC CTT AAC TTC CCC AGC GAC GAC CCA CTG TCT CTG CGC ATG CTT GGG
```

Figure 10 continued

```
M   H   G   T   V   Y   A   N   Y   A   V   D   K   A   D   L   L   I   A   F   G   V   R   F   D   R
ATG CAT GGC ACT GTG TAT GCA AAT TAT GCA GTA GAT AAG GCT GAC CTG TTG NTC GCA TTT GGT GTG CGG TTT GAT CGT

V   T   G   K   I   E   A   F   S   R   S   K   I   E   H   I   D   I   D   P   A   E   I   G   K   N
GTG ACT GGG AAA ATC GAG GCT TTT GCA AGC AGG TCC AAG ATT GNG CAC ATT GAC ATT GAC CCA GCT GAG ATT GGC AAG AAC

K   Q   P   H   V   S   I   C   A   D   V   K   L   A   L   Q   G   L   N   L   P   L   N   G   S   K   A
AAG CAG CCA CAT GTC TCC ATT TGT GCA GAT GTT AAN CTT GCT TTA CAG GGG TTG AAT CTA TTA AAT GGG AGC AAA GCA

Q   Q   L   D   F   G   P   W   H   K   E   L   D   Q   K   R   E   F   P   L   G   F   K   T   F
CAA CAG CTG GAT TTT GGT CCA TGG CAC AAG GAG TTG GAT CAG CAN AGG GAG TTT CCT CTA GGA TTC AAG ACT TTT

G   E   A   I   P   P   Q   Y   A   I   Q   V   L   T   K   A   E   A   H   I   A   T   G   V
GGC GAG GCC ATC CCG CCG CAA TAT GCT ATC CAG GTA CTG ACA AAA GAG GCG ATC GCC ACT GGT GTT

G   Q   H   Q   M   W   A   A   Y   Q   R   P   W   L   S   S   D   L   G   A
GGG CAG CAC CAG ATG TGG GCG GCT TAT CAG CGG CCA TGG CTG TCT TCG GAC TTG GGG GCA

M   G   F   G   L   P   A   E   L   A   N   P   G   T   V   K   V   M   I   L   N   N   Q
ATG GGA TTT GGG TTA CCA GCT GAG TTG GCG AAC CCA GGT GTT ACA AAG GTG ATG ATA TTG AAC CAG

S   F   L   M   N   I   Q   E   R   D   R   Y   K   A   I   R   N   L   T   H   A   V   K   N   P   E   N
AGT TTC CTC ATG AAC ATT CAG GAG TGG GAT AGG TAC AAG GCC ATC CGC AAT CTC GCG CAC ACA CTT GGC AAC CCA GAA AAT

H   L   G   M   V   Q   V   M   E   F   Y   K   G   F   A   K   P   A   V   R   V   T   K   S   E
CAT CTG GGA ATG GTG GTG CAG GAG TGG GAG GAT TTT TAC AAG GGA GCC GCG GTT CGA GTG ACG AAG AGC GAA

E   S   I   Y   P   D   F   V   P   I   A   K   G   F   N   V   P   A   V   R   V   T   K   S   E
GAG AGT GAG ATA TAT CCA GAT TTT GTG ACG ATT GCT AAA GGA TTC AAC GTT CCA GCA GTT CGA GTG ACG AAG AGC GAA
```

Figure 10 continued

```
V   T   A   A   I   K   K   M   L   E   T   P   G   P   Y   L   L   D   I   I   V   P   H   Q   E   H   V
GTC ACT GCA GCA ATC AAG AAG ATG CTT GAG ACC CCA GGG CCA TAC TTG TTG GAT ATC ATA GTC CCG CAT CAG GAG CAC GTG

L   P   M   I   P   N   G   G   A   F   K   D   M   I   M   E   G   D   G   R   T   S   Y
CTG CCT ATG ATC CCA AAC GGT GGT GCT TTC AAG GAC ATG ATC ATG GAG GGT GAT GGC AGG ACC TCG TAC TGA
```

Figure 11

Partial DNA sequence and deduced amino acid sequence of TealMI2 11A

```
SEQ ID NO:4
SEQ ID NO:3

D   V   F   A   Y   P   G   G   A   S   M   E   I   H   Q   A   L   T   R   S   P
  C GAC GTC TTC GCC TAC CCT GGC GGC GCG TCC ATG GAG ATC CAC CAG GCG CTG ACG CGC TCG CCA

V   I   T   N   H   L   F   R   H   E   Q   G   E   A   F   A   A   S   G   R   V
GTC ATC ACC AAC CAC CTC TTC CGC CAC GAG CAG GGG GAG GCG TTC GCG GCG TCC GGC CGC GTC

G   V   C   V   A   T   S   G   P   G   A   T   N   L   V   S   A   L   D   I   P
GGC GTC TGC GTC GCC ACC TCC GGC CCG GGG GCC ACC AAC CTC GTC TCC GCG CTC GAC ATC CCC

M   V   A   I   T   G   Q   V   P   R   P   M   I   G   T   D   A   F   Q   E   V   T
ATG GTC GCC ATC ACG GGC CAG GTC CCC CGC CCC ATG ATC GGC ACG GAT GCG TTC CAG GAG GTC ACG

R   S   I   T   K   H   N   Y   L   V   D   V   E   D   I   P   R   I   Q   E   A   L   A
CGC TCC ATC ACC AAG CAC AAC TAC CTG GTC GAC GTG GAG GAT ATC CCC CGC ATC CAG GAA GCC TTC CTC GCA

S   G   R   P   G   P   V   L   V   D   I   P   K   D   I   Q   Q   M   A   V   P   V   W   D   T
TCC GGC CGC CCG GGG CCG GTG CTC GTT GAT ATC CCC AAG GAC ATC CAG CAG ATG GCT GTG CCT GTC TGG GAC ACG

P   M   S   L   P   G   Y   I   A   R   L   P   K   P   P   S   T   E   S   L   E   Q   V   L   R   L   V
CCG ATG AGT TTG CCA GGG TAC ATC GCC CGC CTG CCC AAG CCA CCA TCT ACT GAA TCG CTT GAG CAG GTC CTG CGT GTT

G   E   S   R   R   P   P   I   L   Y   V   G   G   G   C   A   A   S   G   E   E   L   R   R   F   V   E   L
GGG GAG TCA CGG CGC CGC CCA ATT CTG TAT GTT GGT GGT GGC TGC GCT GCA TCT GGT GAG GAG TTG CGC CGC TTT GTT GAG CTC

T   G   I   P   V   T   T   T   L   M   G   L   G   N   F   P   S   D   D   P   L   S   L   R   M   L   G
ACT GGG ATT CCA GTT ACA ACT ACT CTT ATG GGC CTT GGC AAC TTC CCC AGT GAC GAC CCA CTG TCT CGC ATG CTG GGG
```

Figure 11 continued

```
M   H   G   T   V   Y   A   N   Y   A   V   D   K   A   D   L   L   L   A   F   G   V   R   F   D   R
ATG CAT GGC ACT GTG TAT AAT TAT GCA GTA GAT AAG GCT GAC CTG TTG CTT GCA TTT GGT GTG CGG TTT GAT CGT

V   T   G   K   I   E   V   H   S   A   F   A   S   R   I   G   P   A   E   I   G   K   N
GTG ACC GGG AAA ATC GAG GTC CAT TCC GCA TTT GCA AGC AGG ATC GGA CCA GCT GAG ATT GGC AAG AAC

K   Q   P   H   V   A   D   I   C   A   V   K   L   A   L   N   A   L   L   T   G   S   K   A
AAG CAG CCA CAT GTC GCA GAT ATT TGT GCA GTT AAG CTT GCT TTA AAT GCT CTA TTA ACC GGG AGC AAA GCA

Q   Q   G   L   D   F   G   P   W   H   K   E   L   R   E   F   P   L   G   F   K   T   F
CAA CAG GGT CTG GAT TTT GGT CCA TGG CAC AAG GAG TTG AGG GAG TTT CCT CTA GGA TTC AAG ACT TTT

G   E   A   I   P   P   Q   Y   A   Q   I   D   V   L   D   E   T   K   G   E   A   I   I   A   T   G   V
GGT GAG GCC ATC CCG CCG CAA TAT GCT CAG ATC GAT GTA CTG GAT GAG ACA AAA GGG GAG GCG ATC ATT GCC ACC GGT GTT

G   Q   H   Q   M   W   A   A   Q   Y   Y   T   A   A   V   W   L   R   P   G   Q   S   S   G   L   G   A
GGG CAG CAT CAG ATG TGG GCG GCT CAG TAT TAC ACT GCT GCC GTT TGG CTG CGG CCA GGT CAG TCT TCA TCC GGT TTG GGT GCA

M   G   F   G   L   P   A   A   G   A   V   T   V   D   I   D   G   D   G
ATG GGA TTT GGG TTG CCA GCT GCA GGA GCT GTT ACA GTT GAT ATT GAT GGG GAT GGT

S   F   L   M   N   I   Q   E   W   Q   V   M   V   P   V   K   A   H   T   Y   L   M   I   N   Q
AGT TTC CTC ATG AAC ATT CAG GAG TGG CAG GTG ATG GTT CCA GTG AAG GCG CAC ACA TAC CTT ATG ATA TTG AAC CAG

H   L   G   M   V   D   R   F   Y   T   A   K   R   A   H   T   Y   L   G   T   V   N   P   E   N
CAT CTG GGA ATG GTG GAT AGG TTT TAC AAG GCC CGG GCG CAC ACA TAC CTT GGC AAC GTT ACG AAC CCA GAA AAT

E   S   E   I   Y   P   D   F   V   T   H   A   K   G   F   N   V   P   A   V   R   V   T   K   K   S   E
GAG AGT GAG ATA TAT CCA GAT TTT GTG ACG CAT GCT AAA GGA TTC AAC GTT CCG GCA GTT CGT GTG ACG AAG AAG AGC GAA
```

Figure 11 continued

```
V   T   A   A   I   K   K   M   L   E   T   P   G   P   Y   L   L   D   I   I   V   P   H   Q   E   H   V
GTC ACT GCA GCA ATC AAG AAG ATG CTT GAG ACC CCA GGG CCA TAC TTG TTG GAT ATC ATT GTC CCG CAT CAG GAG CAC GTG

L   P   M   I   P   N   G   G   A   F   K   D   M   I   M   E   G   D   G   R   T   S
CTG CCT ATG ATC CCA AAC GGT GGT GCT TTT AAG GAC ATG ATC ATG GAG GGT GAT GGC AGG ACC TCG TAC
```

Figure 12

```
Als1_ORF_Teal   (SEQ ID NO:5)
Als2_ORF_Teal   (SEQ ID NO:6)
Als3_ORF_Teal   (SEQ ID NO:7)
                                                                                          100
Consensus
Als1_ORF_Teal      (1) GTCTGCGTCGCCACCTCCGGCCCGGGGCCACCAACCTCGTCTCCGCGCT
Als2_ORF_Teal      (1) GTCTGCGTCGCCACCTCCGGCCCGGGGCCACCAACCTCGTCTCCGCGCT
Als3_ORF_Teal      (1) GTCTGCGTCGCCACCTCCGGCCCGGGGCCACCAACCTCGTCTCCGCGCT
Consensus          (1) GTCTGCGTCGCCACCTCCGGCCCGGGGCCACCAACCTCGTCTCCGCGCT 150
Als1_ORF_Teal     (51) CGCCGACGCCCTCCTCGACTCCATCCCCATGGTCGCCATCACGGGCCAGG
Als2_ORF_Teal     (51) CGCCGACGCTCTCCTCGACTCCATCCCCATGGTCGCCATCACGGGCCAGG
Als3_ORF_Teal     (51) CGCTGACGCCCCTCCTCGACTCCATCCCCATGGTCGCCATCACGGGCCAGG
Consensus         (51) CGCCGACGCCCCTCCTCGACTCCATCCCCATGGTCGCCATCACGGGCCAGG 200
Als1_ORF_Teal    (101) TCCCCGCCGCATGATGGCACGGACGCGTTCCAGGAGACGCCCATAGTG
Als2_ORF_Teal    (101) TCCCCGCCGCATGATGGCACGGACGCGTTCCAGGAGACGCCCATCGTG
Als3_ORF_Teal    (101) TCCCCGCCGCATGATGGCACGGATGCGTTCCAGGAGACGCCCATAGTG
Consensus        (101) TCCCCGCCGCATGATGGCACGGACGCGTTCCAGGAGACGCCCATAGTG 250
Als1_ORF_Teal    (151) GAGGTCACGCGCTCCATCACCAAGCACAACTACCTGGTCCTTGACGTGGA
Als2_ORF_Teal    (151) GAGGTCACGCGCTCCATCACCAAGCACAACTACCTGGTCCTTGACGTGGA
Als3_ORF_Teal    (151) GAGGTCACGCGCTCCATCACCAAGCACAACTACCTGGTCCTTGACGTGGA
Consensus        (151) GAGGTCACGCGCTCCATCACCAAGCACAACTACCTGGTCCTTGACGTGGA 300
Als1_ORF_Teal    (201) GGATATCCCCGCGTCATCAGGAAGCCTTCTTCCTTGCATCCTCTGGCC
Als2_ORF_Teal    (201) GGATATCCCCGCGTCATCAGGAAGCCTTCTTCCTTGCATCCTCTGGCC
Als3_ORF_Teal    (201) GGATATCCCCGCGTCATCAGGAAGCCTTCTTCCTCGCGTCCTCTGGCC
Consensus        (201) GGATATCCCCGCGTCATCAGGAAGCCTTCTTCCTTGCATCCTCTGGCC Als1_ORF_Teal    (251) GCCCGGGGCCGGTGCTGGTAGTTGATATCCCCAAGGACATCCAGCAGCAGATG
Als2_ORF_Teal    (251) GCCCGGGGCCGGTGCTGGTTGATATCCCCAAGGACATCCAGCAGCAGATG
Als3_ORF_Teal    (251) GCCCGGGGCCGGTGCTGGTTGATATCCCCAAGGATATCCAGCAGCAGATG
Consensus        (251) GCCCGGGGCCGGTGCTGGTTGATATCCCCAAGGACATCCAGCAGCAGATG
```

Figure 12 Continued

```
              301                                                      350
Als1_ORF_Teal (301) GCTGTGCCCGTCTGGGACACTCCAATGAGTTTGCCAGGGTACATCGCCCG
Als2_ORF_Teal (301) GCTGTGCCTGTCTGGGACACACGCCGATGAGTTTGCCAGGGTACATCGCCCG
Als3_ORF_Teal (301) GCCGTGCCTATCTGGGACACGCCGATGAGTTTGCCAGGGTACATCGCCCG
    Consensus (301) GCTGTGCCTGTCTGGGACACGCCGATGAGTTTGCCAGGGTACATCGCCCG
              351                                                      400
Als1_ORF_Teal (351) CCTGCCCAAGCCACCATCTACTGAATCGCTTGAGCAGGTCCTGCGTCTGG
Als2_ORF_Teal (351) CCTGCCCAAGCCACCATCTACTGAATCGCTTGAGCAGTCCTGCGTCTGG
Als3_ORF_Teal (351) CCTGCCCAAGCCACCATCTACTGAATCGCTTGAGCAGTCCTGCGTCTGG
    Consensus (351) CCTGCCCAAGCCACCATCTACTGAATCGCTTGAGCAGTCCTGCGTCTGG
              401                                                      450
Als1_ORF_Teal (401) TTGGCGAGTCACGGCGCCCAATTCTGTATGTTGGTGGTGCTGCGCTGCG
Als2_ORF_Teal (401) TTGGCGAGTCACGGCGCGCCCAATTCTGTATGTTGGTGGTGCTGCGCTGCA
Als3_ORF_Teal (401) TTGGCGAGTCACGGCGCGCCCAATTCTGTATGTTGGTGGTGCTGCGCTGCA
    Consensus (401) TTGGCGAGTCACGGCGCGCCCAATTCTGTATGTTGGTGGTGCTGCGCTGCA
              451                                                      500
Als1_ORF_Teal (451) TCTGGGCGAGGAGTTGCGCGCCCGCTTTGTTGTTGAGCTTACTGGGATTCCAGTTAC
Als2_ORF_Teal (451) TCTGGTGCGAGGAGTTGCGCCCGCTTTGTTGTTGAGCTCACTGGGATTCCAGTTAC
Als3_ORF_Teal (451) TCCGGCGAGGAGTTGCGCCCGCTTTGTTGTTGAGCTCACTGGGATTCCGGTTAC
    Consensus (451) TCTGGGCGAGGAGTTGCGCCCGCTTTGTTGTTGAGCTCACTGGGATTCCAGTTAC
              501                                                      550
Als1_ORF_Teal (501) AACTACTCTGATGGCCTTGGCAACTTCCCCAGCGACGACGACCACTGTCTC
Als2_ORF_Teal (501) AACTACTCTTATGGCCTTGGCAACTTCCCCAGTGACGACGACCACTGTCTC
Als3_ORF_Teal (501) AACTACTCTGATGGCCTTGGCAACTTCCCCAGCGACGACGACCACTGTCTC
    Consensus (501) AACTACTCTGATGGCCTTGGCAACTTCCCCAGCGACGACGACCACTGTCTC
              551                                                      600
Als1_ORF_Teal (551) TGCGCATGCTTGGGATGCATGGCACTGTGTATGCAAATTATGCAGTAGAT
Als2_ORF_Teal (551) TGCGCATGCTTGGGATGCATGGCACTGTGTATGCAAATTATGCAGTAGAT
Als3_ORF_Teal (551) TGCGCATGCTTGGGATGCATGGCACTGTGTATGCAAATTATGCAGTCGAT
    Consensus (551) TGCGCATGCTTGGGATGCATGGCACTGTGTATGCAAATTATGCAGTAGAT
```

Figure 12 Continued

```
                 601                                                   650
Als1_ORF_Teal  (601) AAGGCTGACCTGTTGCTCGCATTTGTGTGTGCGGTTTGATGATCGTGTGAC
Als2_ORF_Teal  (601) AAGGCTGACCTGTTGCTTGCTTGCATTTGTTGTGTGCGGTTTGATGATCGTGTGAC
Als3_ORF_Teal  (601) AAGGCTGACCTGTTGCTTGCTTGCATTTGTTGTGTGCGGTTTGATGATCGCGTGAC
      Consensus (601) AAGGCTGACCTGTTGCTTGCTTGCATTTGTGTGTGCGGTTTGATGATCGTGTGAC
                 651                                                   700
Als1_ORF_Teal  (651) TGGGAAAATCGAGGCTTTTGCAAGCAGGTCCAAGATTGTGCACATTGACA
Als2_ORF_Teal  (651) CGGGAAAATCGAGGCTTTTGCAAGCAGGTCCAAGATTGTGCACATTGACA
Als3_ORF_Teal  (651) TGGGAAAATCGAGGCCTTTGCAAGCAGGTCCAAGATTGTGCACATTGACA
      Consensus (651) TGGGAAAATCGAGGCTTTTGCAAGCAGGTCCAAGATTGTGCACATTGACA
                 701                                                   750
Als1_ORF_Teal  (701) TTGACCCAGCTGAGATTGGCAAGAACAAGCAGCCACATGTCTCCATTTGT
Als2_ORF_Teal  (701) TTGACCCAGCTGAGATTGGCAAGAACAAGCAGCCACATGTCTCCATTTGT
Als3_ORF_Teal  (701) TTGACCCAGCTGAGATTGGCAAGAACAAGCAGCCACATGTCTCCATTTGT
      Consensus (701) TTGACCCAGCTGAGATTGGCAAGAACAAGCAGCCACATGTCTCCATTTGT
                 751                                                   800
Als1_ORF_Teal  (751) GCAGATGTTAAGCTTGCTTTACAGGGGTTGAATGATCTATTAAATGGGAG
Als2_ORF_Teal  (751) GCAGATGTTAAGCTTGCTTTACAGGGGTTGAATGCTCTATTAAATGGGAG
Als3_ORF_Teal  (751) GCAGATGTTAAGCTTGCTTTACAGGGGTTGAATGCTCTATTAAATGGGAG
      Consensus (751) GCAGATGTTAAGCTTGCTTTACAGGGGTTGAATGCTCTATTAAATGGGAG
                 801                                                   850
Als1_ORF_Teal  (801) CAAAGCACAACACAGGGTCTCGGATTTGGTCCATGGCACAAGGAGTTGGATC
Als2_ORF_Teal  (801) CAAAGCACAACACAGGGTCTCGGATTTGGTCCATGGCACAAGGAGTTGGATC
Als3_ORF_Teal  (801) CAAAGCACAACACAGGGTCTCGGATTTTGGTCCATGGCACAAGGAGTTGGATC
      Consensus (801) CAAAGCACAACACAGGGTCTCGGATTTGGTCCATGGCACAAGGAGTTGGATC
                 851                                                   900
Als1_ORF_Teal  (851) AGCAGAAGAGAGGAGTTTCCTCTAGGATTCAAGACTTTTGGCGAGGCCATC
Als2_ORF_Teal  (851) AGCAGAAGAGAGGAGTTTCCTCTAGGATTCAAGACTTTTGGTGAGGCCATC
Als3_ORF_Teal  (851) AGCAGAAGAGAGGAGTTTCCTCTAGGATTCAAGACTTTTGGCGAGGCCATC
      Consensus (851) AGCAGAAGAGAGGAGTTTCCTCTAGGATTCAAGACTTTTGGCGAGGCCATC
```

Figure 12 Continued

```
                 901                                                                                              950
Als1_ORF_Teal   (901)  CCGCCGCAATATGCTATCCAGGTACTGGATGAGCTGACAAAAGGGGAGGC
Als2_ORF_Teal   (901)  CCGCCGCAATATGCTATCCAGGTACTGGATGAGCTGACAAAAGGGGAGGC
Als3_ORF_Teal   (901)  CCGCCGCAATATGCTATCCAGGTACTGGATGAGCTGACAAAAGGGGAGGC
    Consensus   (901)  CCGCCGCAATATGCTATCCAGGTACTGGATGAGCTGACAAAAGGGGAGGC
                 951                                                                                             1000
Als1_ORF_Teal   (951)  GATCATTGCCACTGGTGTTGGGCAGCACCAGATGTGGGCGGCTCAGTATT
Als2_ORF_Teal   (951)  GATCATTGCCACCGGTGTTGGGCAGCACCAGATGTGGGCGGCTCAGTATT
Als3_ORF_Teal   (951)  GATCATTGCTACTGGTGTTGGGCAGCACCAGATGTGGGCGGCTCAGTATT
    Consensus   (951)  GATCATTGCCACTGGTGTTGGGCAGCACCAGATGTGGGCGGCTCAGTATT
                1001                                                                                             1050
Als1_ORF_Teal  (1001)  ACACTTACAAGCGGCCACGGCAGTGGCTGTCTTCGTCTGGTTTGGGGCA
Als2_ORF_Teal  (1001)  ACACTTACAAGCGGCCACGGCAGTGGCTGTCTTCATCCGGTTTGGGTGCA
Als3_ORF_Teal  (1001)  ACACTTACAAGCGGCCACGGCAGTGGCTGTCTTCGTCTGGTTTGGGGCA
    Consensus  (1001)  ACACTTACAAGCGGCCACGGCAGTGGCTGTCTTCGTCTGGTTTGGGGCA
                1051                                                                                             1100
Als1_ORF_Teal  (1051)  ATGGGATTTGGGTTACCAGCTGCAGCTGGCGCTGCTGTGGCCAACCCAGG
Als2_ORF_Teal  (1051)  ATGGGATTTGGGTTGCCAGCTGCAGCTGGCGCTGCTGTGGCCAACCCAGG
Als3_ORF_Teal  (1051)  ATGGGATTTGGGTTACCAGCTGCAGCTGGCGCTGCTGTGGCCAACCCAGG
    Consensus  (1051)  ATGGGATTTGGGTTACCAGCTGCAGCTGGCGCTGCTGTGGCCAACCCAGG
                1101                                                                                             1150
Als1_ORF_Teal  (1101)  TGTTACAGTTGTTGACATTGATGGTAGTTTCCTCATGAACATTC
Als2_ORF_Teal  (1101)  TGTTACAGTTGTTGACATTGATGGGATGGTAGTTTCCTCATGAACATTC
Als3_ORF_Teal  (1101)  TGTTACAGTTGT-GACATTGATGGAGATGGTAGTTTCCTCATGAACATTC
    Consensus  (1101)  TGTTACAGTTGTTGACATTGATGG[]GATGGTAGTTTCCTCATGAACATTC
                1151                                                                                             1200
Als1_ORF_Teal  (1151)  AGGAGTTGGCGTTGATCCGCATTGAGAACCTCCCAGTGAAGGTGATGATA
Als2_ORF_Teal  (1151)  AGGAGTTGGCGTTGATCCGTATTGAGAACCTCCCAGTGAAGGTGATGATA
Als3_ORF_Teal  (1151)  AGGAGTTGGCATTGATCCGTATTGAGAACCTCCCTGTGAAGGTGATGATA
    Consensus  (1151)  AGGAGTTGGCGTTGATCCGTATTGAGAACCTCCCAGTGAAGGTGATGATA
```

Figure 12 Continued

```
                1201                                              1250
Als1_ORF_Teal  (1201) TTGAACAACCAGCATCTGGGAATGGTGGTGCAGTGGGAGGATAGGTTTTA
Als2_ORF_Teal  (1201) TTGAACAACCAGCATCTGGGAATGGTGGTGCAGTGGGAGGATAGGTTTTA
Als3_ORF_Teal  (1201) TTGAACAACCAGCATCTGGGAATGGTGGTGCAGTGGGAGGATAGGTTTTA
Consensus      (1201) TTGAACAACCAGCATCTGGGAATGGTGGTGCAGTGGGAGGATAGGTTTTA
                1251                                              1300
Als1_ORF_Teal  (1251) CAAGGCCAATCGGGCGCACACATACCTTGGCAACCCAGAAAATGAGAGTG
Als2_ORF_Teal  (1251) CAAGGCCAATCGGGCGCACACATACCTTGGCAACCCAGAAAATGAGAGTG
Als3_ORF_Teal  (1251) CAAGGCCAATCGGGCGCACACATACCTTGGCAACCCAGAAAATGAGAGTG
Consensus      (1251) CAAGGCCAATCGGGCGCACACATACCTTGGCAACCCAGAAAATGAGAGTG
                1301                                              1350
Als1_ORF_Teal  (1301) AGATATATCCAGATTTTGTGACGATTGCTAAAGGATTCAACGTTCCAGCA
Als2_ORF_Teal  (1301) AGATATATCCAGATTTTGTGACGATTGCTAAAGGATTCAACGTTCCGGCA
Als3_ORF_Teal  (1301) AGATATATCCAGATTTTGTGACGATTGCTAAAGGATTCAACGTTCCGGCA
Consensus      (1301) AGATATATCCAGATTTTGTGACGATTGCTAAAGGATTCAACGTTCCGGCA
                1351                                              1400
Als1_ORF_Teal  (1351) GTTCGAGTGACGAAGAAGAGCGAAGTCACTGCAGCAATCAAGAAGATGCT
Als2_ORF_Teal  (1351) GTTCGTGTGACGAAGAAGAGCGAAGTCACTGCAGCAATCAAGAAGATGCT
Als3_ORF_Teal  (1351) GTTCGTGTGACGAAGAAGAGCGAAGTCACTGCAGCAATCAAGAAGATGCT
Consensus      (1351) GTTCGTGTGACGAAGAAGAGCGAAGTCACTGCAGCAATCAAGAAGATGCT
                1401                                              1450
Als1_ORF_Teal  (1401) TGAGACCCCCAGGGCCCATACTTGTTGGATATCATAGTCCCGCATCAGGAGC
Als2_ORF_Teal  (1401) TGAGACCCCCAGGGCCCATACTTGTTGGATATCATTGTCCCGCATCAGGAGC
Als3_ORF_Teal  (1401) TGAGACCCCCAGGGCCCATACTTGTTGGATATCATCGTCCCGCATCAGGAGC
Consensus      (1401) TGAGACCCCCAGGGCCCATACTTGTTGGATATCAT[ ]GTCCCGCATCAGGAGC
                1451                                              1500
Als1_ORF_Teal  (1451) ACGTGCTGCCTATGATCCCAAGCGGTGGTGCTTTCAAGGACATGATCATG
Als2_ORF_Teal  (1451) ACGTGCTGCCTATGATCCCAAGCGGTGGTGCTTTTAAGGACATGATCATG
Als3_ORF_Teal  (1451) ACGTGCTGCCTATGATCCCAAGCGGTGGTGCTTTCAAGGACATGATCATG
Consensus      (1451) ACGTGCTGCCTATGATCCCAAGCGGTGGTGCTTTCAAGGACATGATCATG
```

Figure 12 Continued

```
                        1501                     1524
Als1_ORF_Teal  (1501)   GAGGGTGATGGCAGGACCTCGTAC
Als2_ORF_Teal  (1501)   GAGGGTGATGGCAGGACCTCGTAC
Als3_ORF_Teal  (1501)   GAGGGTGATGGCAGGACCTCGTAC
   Consensus   (1501)   GAGGGTGATGGCAGGACCTCGTAC
```

WHEAT PLANTS HAVING INCREASED RESISTANCE TO IMIDAZOLINONE HERBICIDES

CROSS-REFERENCE TO RELATED APPLICATIONS

This application is a divisional of U.S. patent application Ser. No. 13/366,932, filed Feb. 6, 2012, which is a divisional of U.S. patent application Ser. No. 12/363,087, filed Jan. 30, 2009, which is now U.S. Pat. No. 8,110,727, issued on Feb. 07, 2012, which is a divisional of U.S. patent application Ser. No. 10/486,605, filed Feb. 9, 2004, which is now U.S. Pat. No. 7,897,845, issued on Mar. 1, 2011, which is the U.S. National Stage of International Application PCT/CA02/01051, filed Jul. 10, 2002, which published in English on Feb. 20, 2003 and designates the U.S., which claims priority benefit of U.S. Provisional Patent Application Ser. No. 60/311,282, filed Aug. 9, 2001; all of which are hereby incorporated herein in their entirety by reference.

FIELD OF THE INVENTION

The present invention relates in general to plants having an increased resistance to imidazolinone herbicides. More specifically, the present invention relates to wheat plants obtained by mutagenesis and cross-breeding and transformation that have an increased resistance to imidazolinone herbicides.

BACKGROUND OF THE INVENTION

Acetohydroxyacid synthase (AHAS; EC 4.1.3.18) is the first enzyme that catalyzes the biochemical synthesis of the branched chain amino acids valine, leucine and isoleucine (Singh B. K., 1999 Biosynthesis of valine, leucine and isoleucine in: Singh B. K. (Ed) Plant amino acids. Marcel Dekker Inc. New York, N.Y. Pg 227-247). AHAS is the site of action of four structurally diverse herbicide families including the sulfonylureas (LaRossa R A and Falco S C, 1984 Trends Biotechnol 2:158-161), the imidazolinones (Shaner et al., 1984 Plant Physiol 76:545-546), the triazolopyrimidines (Subramanian and Gerwick, 1989 Inhibition of acetolactate synthase by triazolopyrimidines in (ed) Whitaker J R, Sonnet P E Biocatalysis in agricultural biotechnology. ACS Symposium Series, American Chemical Society. Washington, D.C. Pg 277-288), and the pyrimidyloxybenzoates (Subramanian et al., 1990 Plant Physiol 94: 239-244). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, fluazasulfuron, imazosulfuron, pyrazosulfuron ethyl and halosulfuron.

Due to their high effectiveness and low-toxicity, imidazolinone herbicides are favored for application by spraying over the top of a wide area of vegetation. The ability to spray an herbicide over the top of a wide range of vegetation decreases the costs associated with plantation establishment and maintenance and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson, 1985 Weed Sci. 33:469-471). Other crops such as corn (Newhouse et al., 1992 Plant Physiol. 100:882-886) and rice (Barrette et al., 1989 Crop Safeners for Herbicides, Academic Press New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al., 1984 Plant Physiol. 76:545-546; Brown et al., 1987 Pestic. Biochm. Physiol. 27:24-29). Other plant physiological differences such as absorption and translocation also play an important role in sensitivity (Shaner and Robinson, 1985 Weed Sci. 33:469-471).

Crop cultivars resistant to imidazolinones, sulfonylureas and triazolopyrimidines have been successfully produced using seed, microspore, pollen, and callus mutagenesis in *Zea mays*, *Arabidopsis thaliana*, *Brassica napus*, *Glycine max*, and *Nicotiana tabacum* (Sebastian et al., 1989 Crop Sci. 29:1403-1408; Swanson et al., 1989 Theor. Appl. Genet. 78:525-530; Newhouse et al., 1991 Theor. Appl. Genet. 83:65-70; Sathasivan et al., 1991 Plant Physiol. 97:1044-1050; Mourand et al., 1993 J. Heredity 84: 91-96). In all cases, a single, partially dominant nuclear gene conferred resistance. Four imidazolinone resistant wheat plants were also previously isolated following seed mutagenesis of *Triticum aestivum* L. cv Fidel (Newhouse et al., 1992 Plant Physiol. 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al., 1992 Plant Physiol. 100:882-886).

Computer-based modeling of the three dimensional conformation of the AHAS-inhibitor complex predicts several amino acids in the proposed inhibitor binding pocket as sites where induced mutations would likely confer selective resistance to imidazolinones (Ott et al., 1996 J. Mol. Biol. 263:359-368) Wheat plants produced with some of these rationally designed mutations in the proposed binding sites of the AHAS enzyme have in fact exhibited specific resistance to a single class of herbicides (Ott et al., 1996 J. Mol. Biol. 263:359-368).

Plant resistance to imidazolinone herbicides has also been reported in a number of patents. U.S. Pat. Nos. 4,761,373, 5,331,107, 5,304,732, 6,211,438, 6,211,439 and 6,222,100 generally describe the use of an altered AHAS gene to elicit herbicide resistance in plants, and specifically discloses certain imidazolinone resistant corn lines. U.S. Pat. No. 5,013,659 discloses plants exhibiting herbicide resistance possessing mutations in at least one amino acid in one or more conserved regions. The mutations described therein encode either cross-resistance for imidazolinones and sulfonylureas or sulfonylurea-specific resistance, but imidazolinone-specific resistance is not described. Additionally, U.S. Pat. No. 5,731,180 and U.S. Pat. No. 5,767,361 discuss an isolated gene having a single amino acid substitution in a wild-type monocot AHAS amino acid sequence that results in imidazolinone-specific resistance.

To date, the prior art has not described imidazolinone resistant wheat plants containing more than one altered AHAS gene. Nor has the prior art described imidazolinone resistant wheat plants containing mutations on genomes other than the genome from which the FS-4 gene is derived. Therefore, what is needed in the art is the identification of imidazolinone resistance genes from additional genomes. What are also needed in the art are wheat plants having increased resistance to herbicides such as imidazolinone and containing more than one altered AHAS gene. Also needed are methods for controlling weed growth in the vicinity of such wheat plants. These compositions and methods would allow for the use of spray over techniques when applying herbicides to areas containing wheat plants.

SUMMARY OF THE INVENTION

The present invention provides wheat plants comprising IMI nucleic acids, wherein the wheat plant has increased resistance to an imidazolinone herbicide as compared to a wild-type variety of the plant. The wheat plants can contain one, two, three or more IMI nucleic acids. In one embodiment, the wheat plant comprises multiple IMI nucleic acids located on different genomes. Preferably, the IMI nucleic acids encode proteins comprising a mutation in a conserved amino acid sequence selected from the group consisting of a Domain A, a Domain B, a Domain C, a Domain D and a Domain E. More preferably, the mutation is in a conserved Domain E or a conserved Domain C. Also provided are plant parts and plant seeds derived from the wheat plants described herein. In another embodiment, the wheat plant comprises an IMI nucleic acid that is not an Imi1 nucleic acid. The IMI nucleic acid can be an Imi2 or Imi3 nucleic acid, for example.

The IMI nucleic acids of the present invention can comprise a nucleotide sequence selected from the group consisting of: a polynucleotide of SEQ ID NO:1; a polynucleotide of SEQ ID NO:3; a polynucleotide sequence encoding a polypeptide of SEQ ID NO:2; a polynucleotide sequence encoding a polypeptide of SEQ ID NO:4, a polynucleotide comprising at least 60 consecutive nucleotides of any of the aforementioned polynucleotides; and a polynucleotide complementary to any of the aforementioned polynucleotides.

The plants of the present invention can be transgenic or non-transgenic. Examples of non-transgenic wheat plants having increased resistance to imidazolinone herbicides include a wheat plant having an ATCC Patent Deposit Designation Number PTA-3953 or PTA-3955; or a mutant, recombinant, or genetically engineered derivative of the plant with ATCC Patent Deposit Designation Number PTA-3953 or PTA-3955; or of any progeny of the plant with ATCC Patent Deposit Designation Number PTA-3953 or PTA-3955; or a plant that is a progeny of any of these plants.

In addition to the compositions of the present invention, several methods are provided. Described herein are methods of modifying a plant's tolerance to an imidazolinone herbicide comprising modifying the expression of an IMI nucleic acid in the plant. Also described are methods of producing a transgenic plant having increased tolerance to an imidazolinone herbicide comprising, transforming a plant cell with an expression vector comprising one or more IMI nucleic acids and generating the plant from the plant cell. The invention further includes a method of controlling weeds within the vicinity of a wheat plant, comprising applying an imidazolinone herbicide to the weeds and to the wheat plant, wherein the wheat plant has increased resistance to the imidazolinone herbicide as compared to a wild type variety of the wheat plant and wherein the plant comprises one or more IMI nucleic acids. In some preferred embodiments of these methods, the plants comprise multiple IMI nucleic acids that are located on different wheat genomes.

BRIEF DESCRIPTION OF THE DRAWINGS

FIG. 1 is a table showing the results of single plant evaluation of imazamox resistance in parental and $F_1$ populations resulting from reciprocal crosses between resistant lines and CDC Teal. The numbers presented represent the number of plants scored into each phenotypic class. Parental lines are indicated in bold. The number of parental lines scored include those scored with the $F_2$ populations.

FIG. 2 is a table showing the reaction to imazamox in $F_2$ and $BCF_1$ populations resulting from crosses between resistant lines and CDC Teal and Chi-square tests of single locus and two locus models (15A×Teal) for control of resistance. The symbols used in FIG. 2 indicate the following: a—Chi-square P value (1 df) represents the probability that deviations from the tested ratio are due to chance alone. Chi-square P values greater than 0.05 indicate that observed values were not significantly different from expected values; b—Chi-square P value representing the probability that deviations between $F_2$ populations resulting from reciprocal crosses between CDC Teal and resistant lines are due to chance alone. Chi-square values greater than 0.05 indicate that reciprocal $F_2$ populations were homogeneous, and data from the two reciprocal populations was pooled; c—CDC Teal was used as the recurrent parent; d—Ratios tested were based on the results of the $F_2$ generation; and e—Chi-square P value (1 df) for $BCF_1$ ratio.

FIG. 3 is a table showing the results of an evaluation of resistance to imazamox in $F_{2:3}$ families resulting from crosses between resistant lines and CDC Teal and Chi-square tests of single-locus and two locus models (15A× Teal) for control of resistance. The symbols used in FIG. 3 indicate the following: a—Family segregation ratios tested were based on the results of the $F_2$ and $BCF_1$ populations; b—Chi-square P value (2 df) representing the probability that deviations from the tested ratio are due to chance alone. Chi-square P values greater than 0.05 indicate that observed values were not significantly different from expected values.

FIG. 4 is a table showing the results of a single plant evaluation of imazamox resistance in $F_2$ populations resulting from inter-crosses between resistant lines. Chi-square ratios tested were based on the results of the $F_2$ and $F_{2:3}$ family results obtained from crosses between resistant lines and CDC Teal. The 15:1 ratio tested is for a two locus model and the 63:1 ratio tested is for a three locus model. The "a" symbol used in FIG. 4 indicates the following: Chi-square P value (1 df) representing the probability that deviations from the tested ratio are due to chance alone. Chi-square P values greater than 0.05 indicate that observed values were not significantly different from expected values.

FIG. 5 is a table showing the results of an evaluation of imazamox resistance in $F_{2:3}$ families resulting from segregating inter-crosses between resistant lines. The symbols used in FIG. 5 indicate the following: a—Family segregation ratios tested were based on the results of the $F_2$ populations examined; b—Chi-square P value (2 df) representing the probability that deviations from the tested ratio are due to chance alone. Chi-square P values greater than 0.05 indicate that observed values were not significantly different from expected values.

FIG. 6 is a table comparing the percent uninhibited in vitro AHAS activity in four wheat lines in the presence of increasing concentrations of the imidazolinone herbicide imazamox. Teal is a wild type line with no tolerance to imidazolinone herbicides while BW755 contains the FS4 mutant gene.

FIG. 7 is a table comparing injury sustained by three wheat genotypes when treated with either a 10× or 30× rate of imazamox. The 1× rate is 20 g/ha. BW755 contains the FS4 mutant gene. 15A/11A is a bulk of selfed progeny from the cross of Teal11A and Teal15A. The population was not yet homozygous at all three non-allelic loci.

Figure 9:
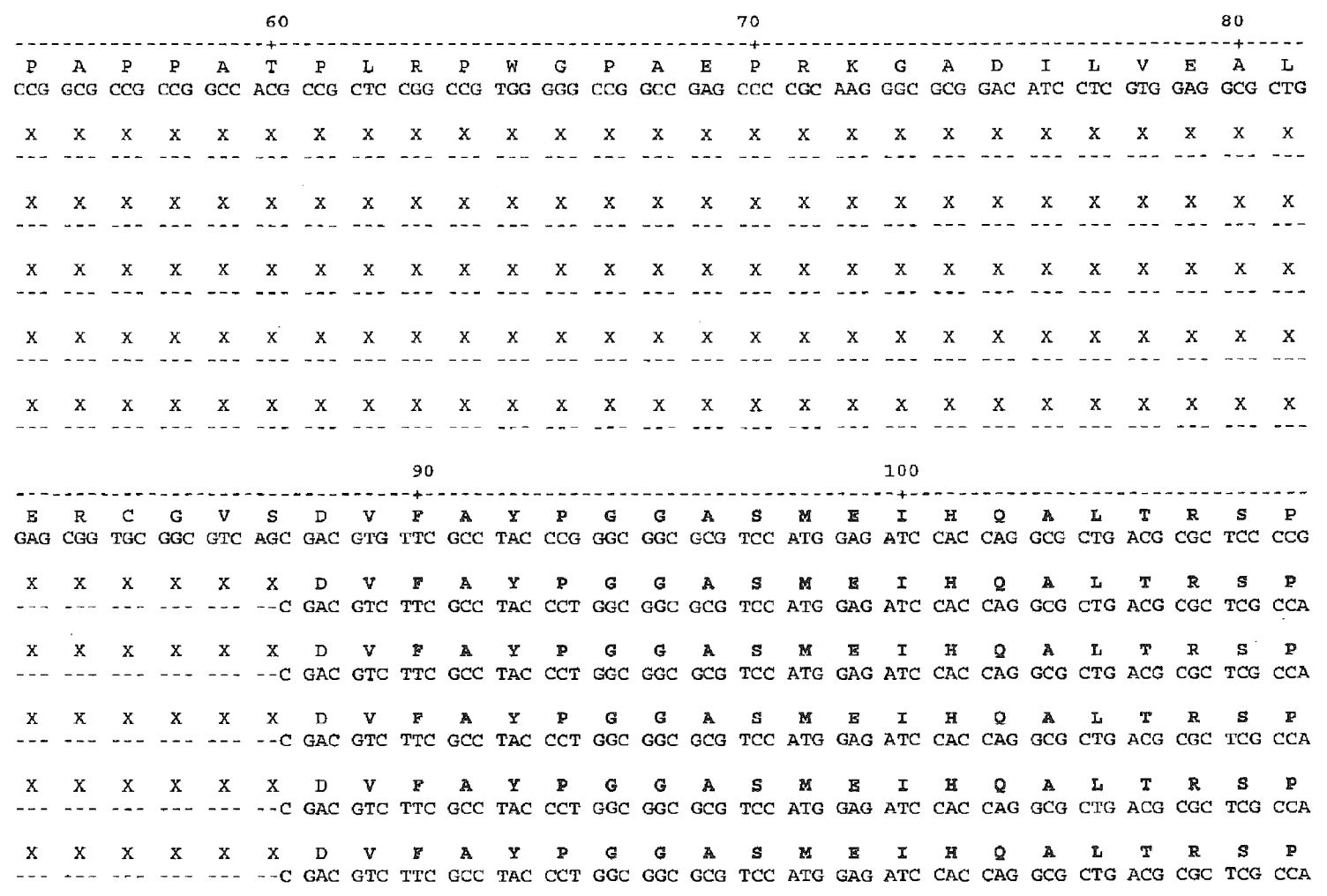
Figure 9:
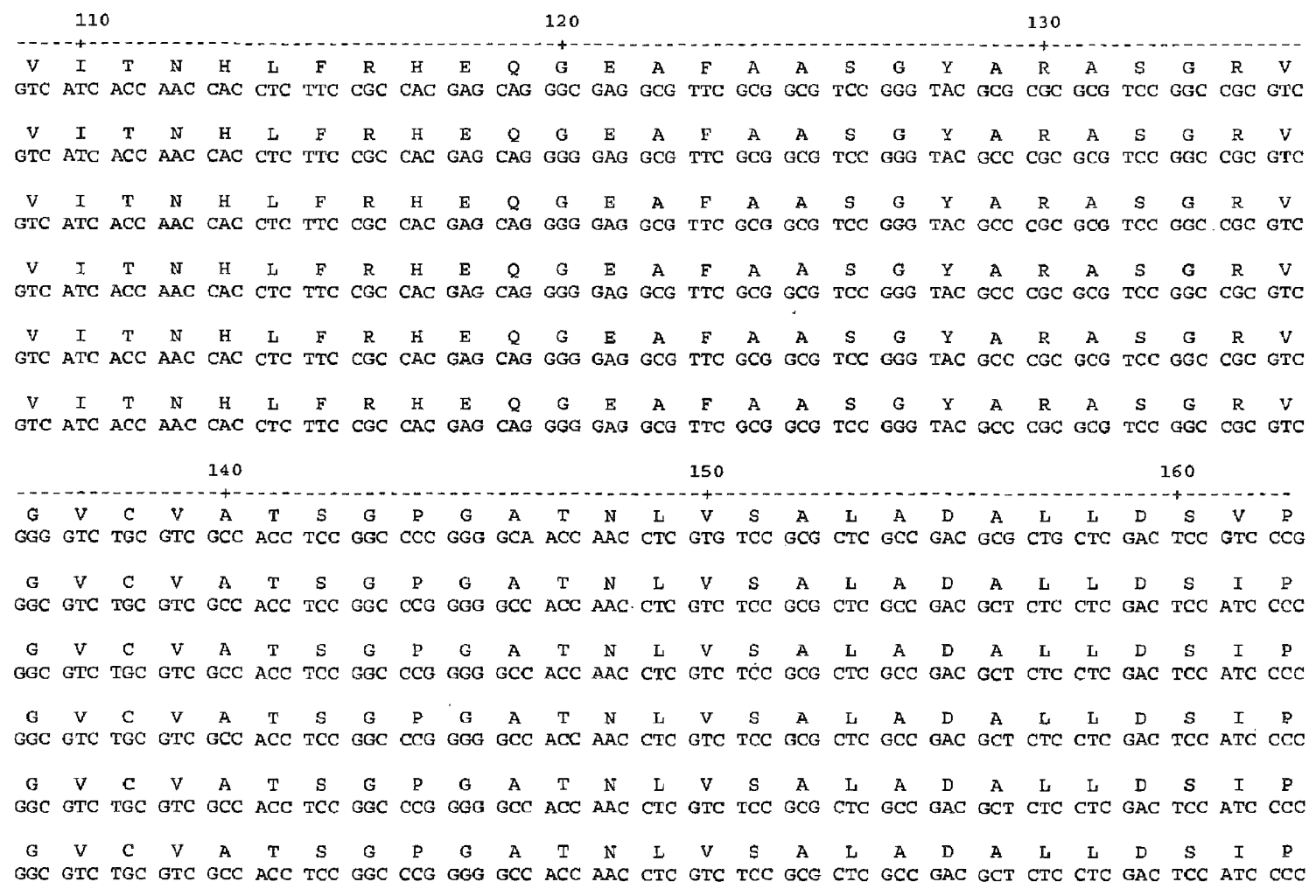
Figure 9:
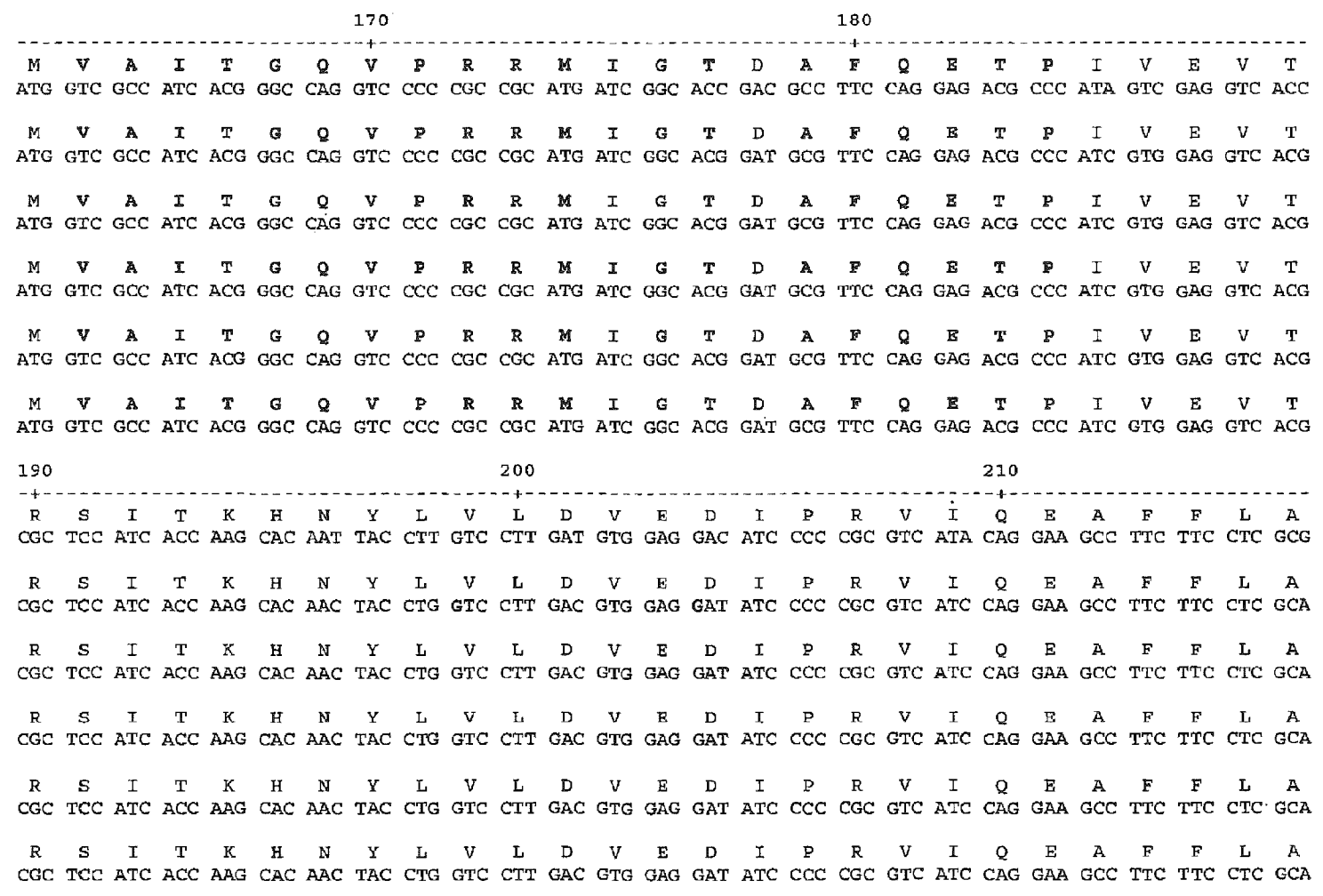
Figure 9:
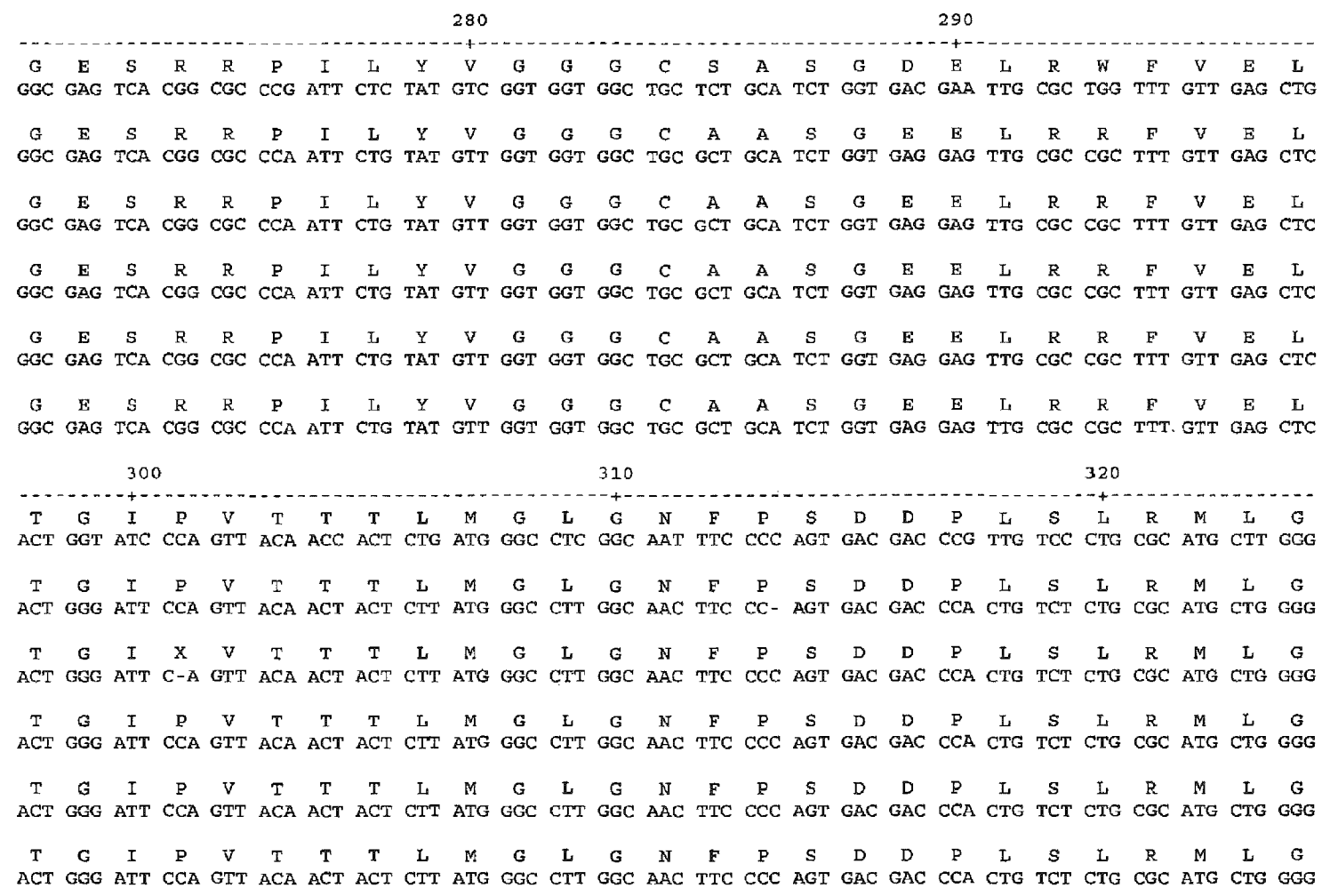
Figure 9:
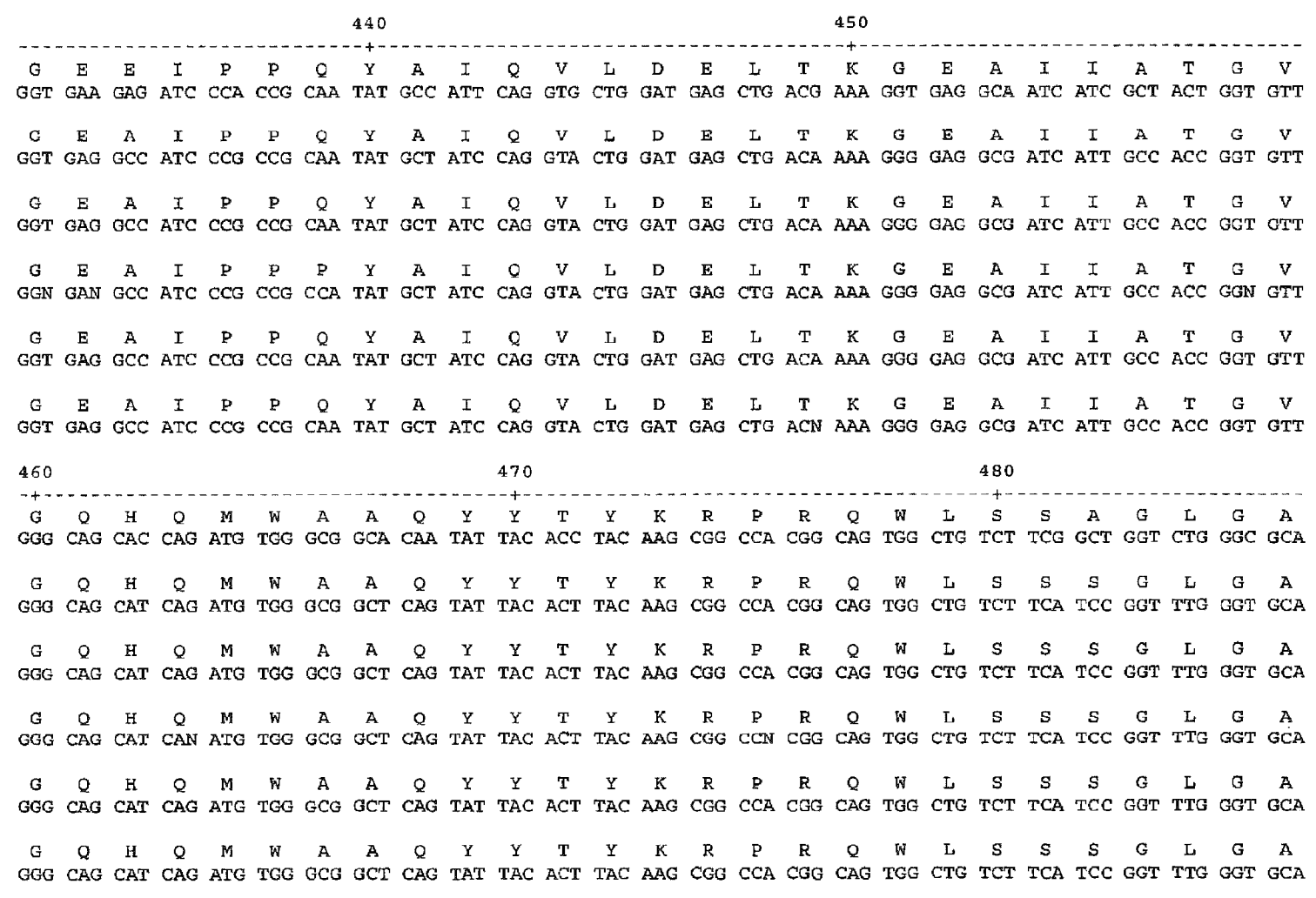
Figure 9:
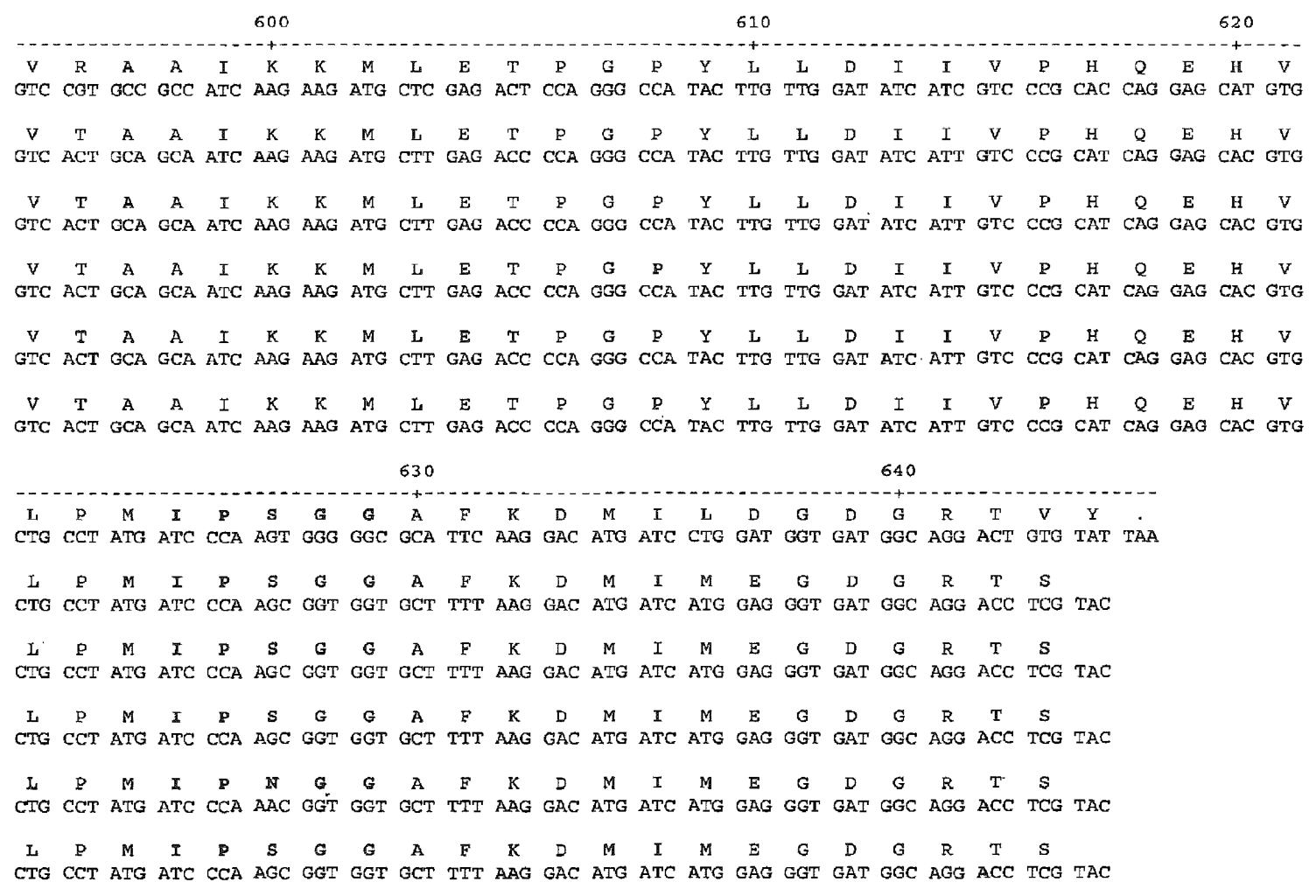

FIG. 9 shows a DNA sequence alignment of partial Als2 and Imi2 wheat genes amplified from genomic DNA: CDC Teal (row 2; SEQ ID NO:25 and SEQ ID NO:26), BW755 (row 3; SEQ ID NO:27 and SEQ ID NO:28), TealIMI 10A (row 4; SEQ ID NO:29 and SEQ ID NO:30), TealIMI 11A (row 5; SEQ ID NO:31 and SEQ ID NO:32) and TealIMI 15A (row 6; SEQ ID NO:33 and SEQ ID NO:34). Partial AHAS sequences were aligned with a complete rice AHAS sequence (row 1; SEQ ID NO:13 and SEQ ID NO:14) derived from GenBank (Accession no. AB049822) and translated into protein sequences (presented above the DNA sequences). The five highly conserved domains known to house mutations that confer resistance to AHAS inhibitors are indicated in bold. Note the guanine to adenine substitution in TealIMI 11A, resulting in a serine to asparagine substitution (serine-627 in rice) in the IPSGG domain of the Als2 gene. Accordingly, the resistance gene present in TealIMI 11A plant has been designated as part of the Imi2 class of nucleic acids. This Teal resistance gene is referred to herein as TealIMI2 11A.

FIG. 10 shows the partial DNA sequence of TealIMI 15A (SEQ ID NO:1) and the deduced amino acid sequence of the same (SEQ ID NO:2).

FIG. 11 shows the partial DNA sequence of TealIMI2 11A (SEQ ID NO:3) and the deduced amino acid sequence of the same (SEQ ID NO:4).

FIG. 12 shows the wild type nucleic acid sequence of the Teal ALS1 ORF (SEQ ID NO:5), the Teal ALS2 ORF (SEQ ID NO:6) the Teal ALS3 ORF (SEQ ID NO:7).

DETAILED DESCRIPTION

Figure 8:
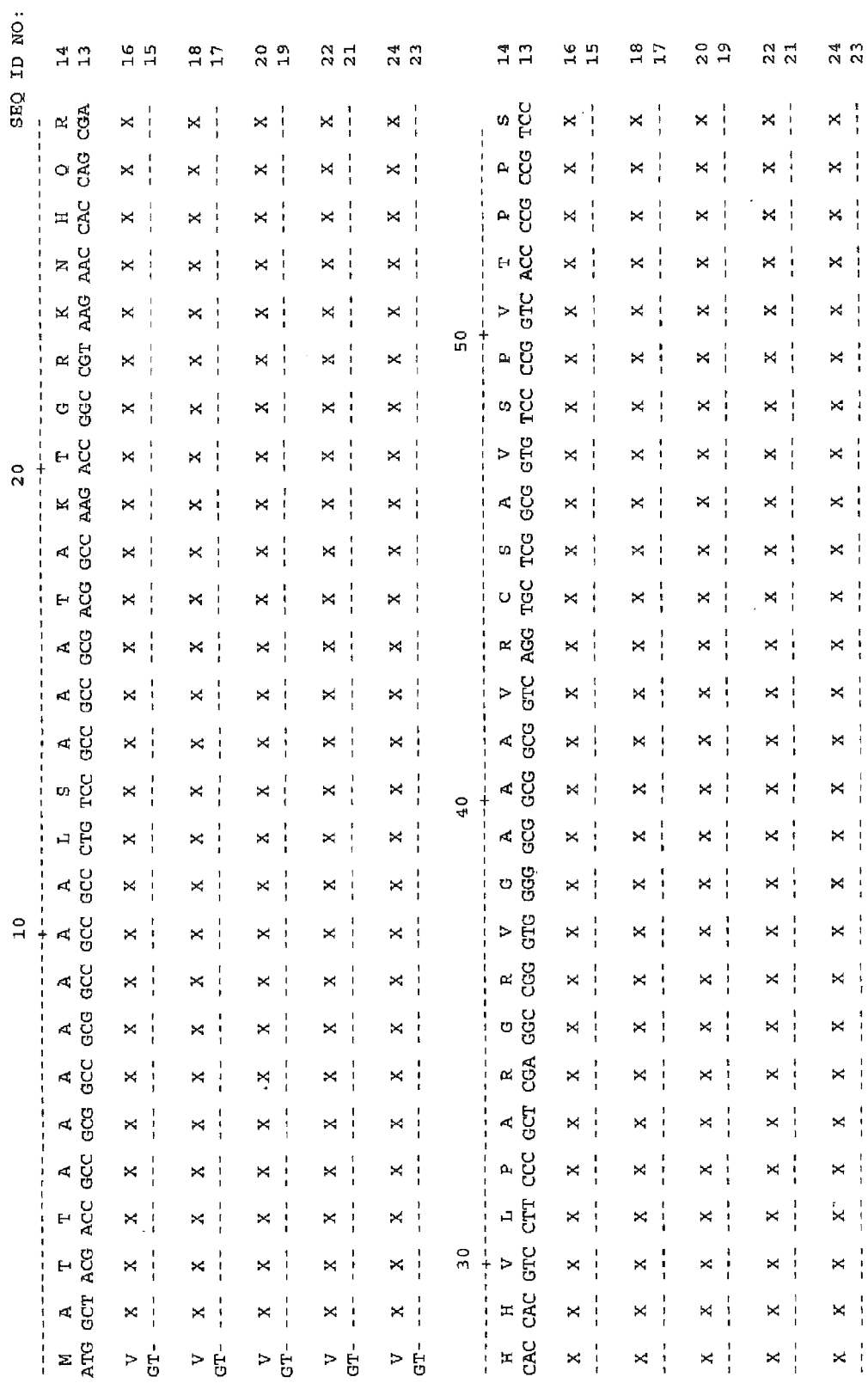
FIG. 8 shows a DNA sequence alignment of partial Als1 and Imi1 wheat genes amplified from genomic DNA: CDC Teal (row 2; SEQ ID NO:15 and SEQ ID NO:16), BW755 (row 3; SEQ ID NO:17 and SEQ ID NO:18), TealIMI 10A (row 4; SEQ ID NO:19 and SEQ ID NO:20), TealIMI 11A (row 5; SEQ ID NO:21 and SEQ ID NO:22), and TealIMI 15A (row 6; SEQ ID NO:23 and SEQ ID NO:24). Partial sequences were aligned with a complete rice ALS gene sequence (row 1; SEQ ID NO:13 and SEQ ID NO:14) derived from Genbank (Accession no. ABO49822) and translated to protein sequences (presented on top of the DNA sequences). The five highly conserved amino acid domains known to house mutations that confer resistance to AHAS inhibitors are indicated in bold. Note the guanine to adenine substitutions in BW755, TealIMI 10A, and TealIMI 15A result in a serine to asparagine substitution (serine-627 in rice) in the IPSGG domain (Domain E) of the Als1 gene. Accordingly, the resistance genes present in the BW755, TealIMI 10A, and TealIMI 15A plants have been designated as part of the Imi1 class. These Teal resistance genes are referred to herein as TealIMI 10A and TealIMI 15A.
Figure 8:
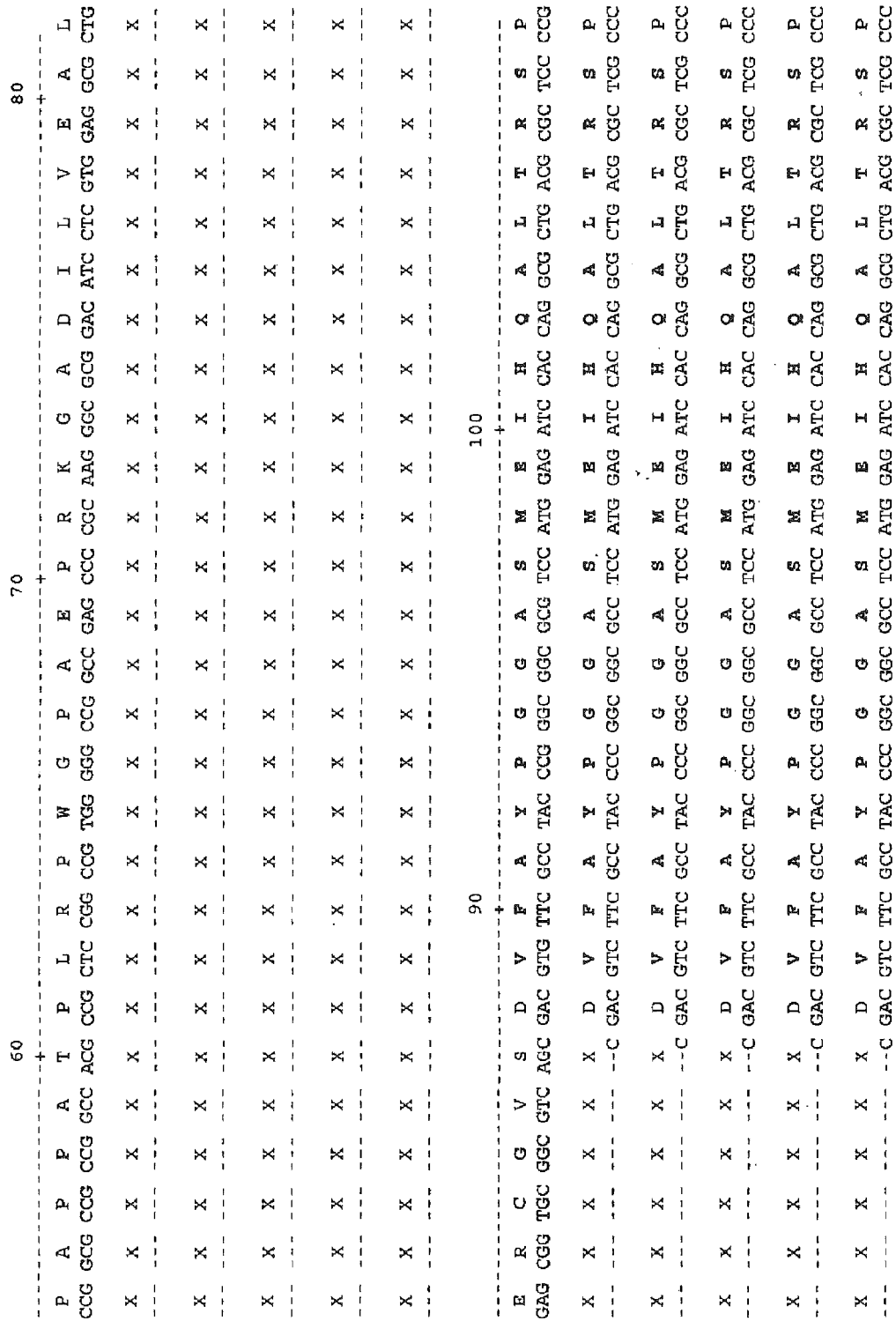
Figure 8:
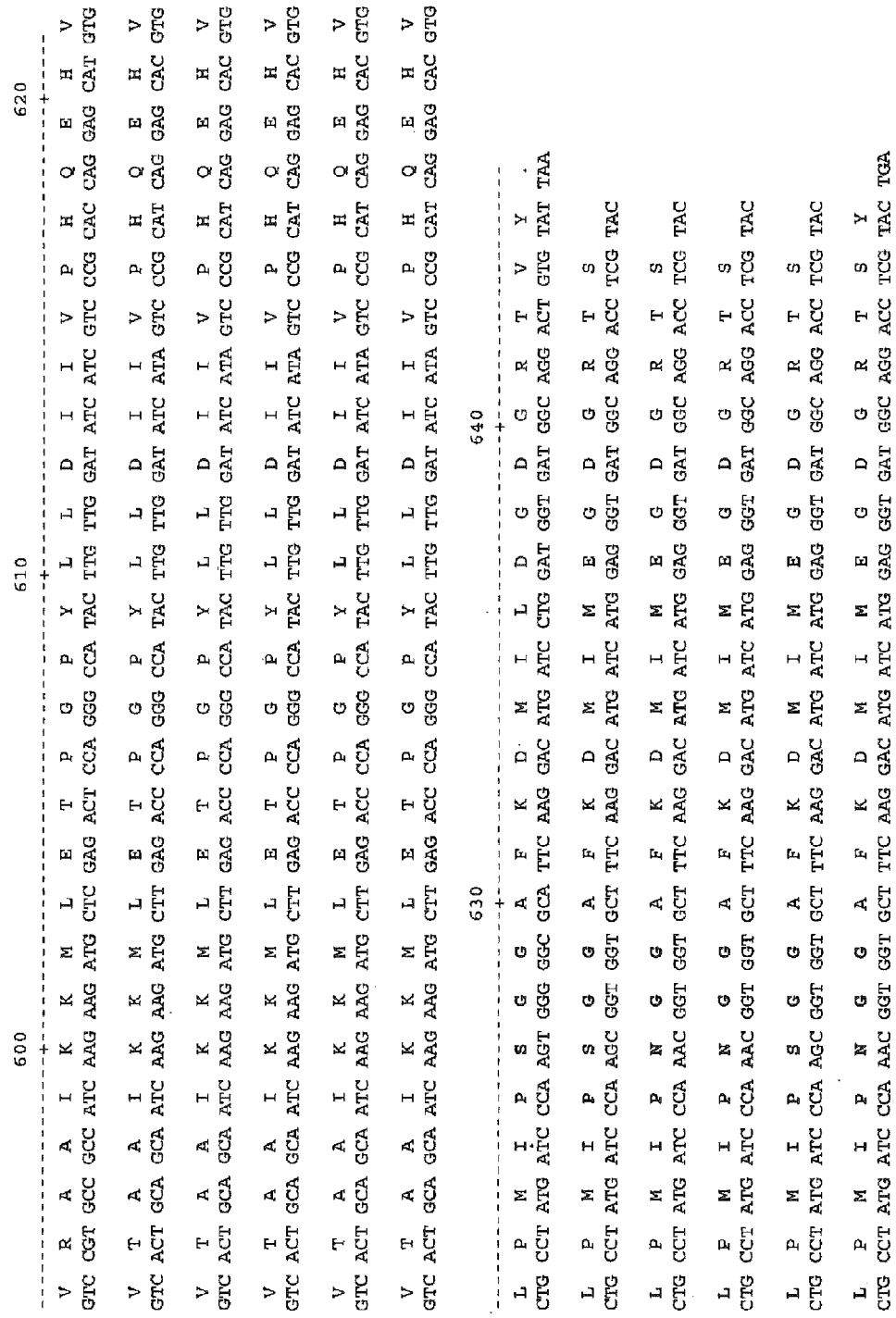

The present invention is directed to wheat plants, wheat plant parts and wheat plant cells having increased resistance to imidazolinone herbicides. The present invention also includes seeds produced by the wheat plants described herein and methods for controlling weeds in the vicinity of the wheat plants described herein. It is to be understood that as used in the specification and in the claims, "a" or "an" can mean one or more, depending upon the context in which it is used. Thus, for example, reference to "a cell" can mean that at least one cell can be utilized.

As used herein, the term "wheat plant" refers to a plant that is a member of the *Triticum* genus. The wheat plants of the present invention can be members of a *Triticum* genus including, but not limited to, *T. aestivum, T. turgidum, T. timopheevii, T. monococcum, T. zhukovskyi* and *T. urartu* and hybrids thereof. Examples of *T. aestivum* subspecies included within the present invention are *aestivum* (common wheat), *compactum* (club wheat), *macha* (*macha* wheat), *vavilovi* (vavilovi wheat), *spelta* and *sphaerococcum* (shot wheat). Examples of *T. turgidum* subspecies included within the present invention are *turgidum, carthlicum, dicoccon, durum, paleocolchicum, polonicum, turanicum* and *dicoccoides*. Examples of *T. monococcum* subspecies included within the present invention are *monococcum* (einkorn) and *aegilopoides*. In one embodiment of the present invention, the wheat plant is a member of the *Triticum aestivum* species, and more particularly, the CDC Teal cultivar.

The term "wheat plant" is intended to encompass wheat plants at any stage of maturity or development as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts and the like. The present invention also includes seeds produced by the wheat plants of the present invention. In one embodiment, the seeds are true breeding for an increased resistance to an imidazolinone herbicide as compared to a wild type variety of the wheat plant seed.

The present invention describes a wheat plant comprising one or more IMI nucleic acids, wherein the wheat plant has increased resistance to an imidazolinone herbicide as compared to a wild-type variety of the plant. As used herein, the term "IMI nucleic acid" refers to a nucleic acid that is mutated from an AHAS nucleic acid in a wild type wheat plant that confers increased imidazolinone resistance to a plant in which it is transcribed. Wild type Teal AHAS nucleic acids are shown in SEQ ID NO:5 (Teal ALS1 ORF), SEQ ID NO:6 (Teal ALS2 ORF) and SEQ ID NO:7 (Teal ALS3 ORF). In one embodiment, the wheat plant comprises multiple IMI nucleic acids. As used when describing the IMI nucleic acids, the term "multiple" refers to IMI nucleic acids that have different nucleotide sequences and does not refer to a mere increase in number of the same IMI nucleic acid.

For example, the IMI nucleic acids can be different due to the fact that they are derived from or located on different wheat genomes.

It is possible for the wheat plants of the present invention to have multiple IMI nucleic acids from different genomes since these plants can contain more than one genome. For example, a *Triticum aestivum* wheat plant contains three genomes sometimes referred to as the A, B and D genomes. Because AHAS is a required metabolic enzyme, it is assumed that each genome has at least one gene coding for the AHAS enzyme, commonly seen with other metabolic enzymes in hexaploid wheat that have been mapped. The AHAS nucleic acid on each genome can, and usually does, differ in its nucleotide sequence from an AHAS nucleic acid on another genome. One of skill in the art can determine the genome of origin of each AHAS nucleic acid through genetic crossing and/or either sequencing methods or exonuclease digestion methods known to those of skill in the art and as also described in Example 2 below. For the purposes of this invention, IMI nucleic acids derived from one of the A, B or D genomes are distinguished and designated as Imi1, Imi2 or Imi3 nucleic acids.

It is not stated herein that any particular Imi nucleic acid class correlates with any particular A, B or D genome. For example, it is not stated herein that the Imi1 nucleic acids correlate to A genome nucleic acids, that Imi2 nucleic acids correlate to B genome nucleic acids, etc. The Imi1, Imi2 and Imi3 designations merely indicate that the IMI nucleic acids within each such class do not segregate independently, whereas two IMI nucleic acids from different classes do segregate independently and may therefore be derived from different wheat genomes. The Imi1 class of nucleic acids includes the FS-4 gene as described by Newhouse et al. (1992 Plant Physiol. 100:882-886) and the TealIMI 15A gene described in more detail below. The Imi2 class of nucleic acids includes the TealIMI2 11A gene described below. Each Imi class can include members from different wheat species. Therefore, each imi class includes IMI nucleic acids that differ in their nucleotide sequence but that are nevertheless designated as originating from, or being located on, the same wheat genome using inheritance studies as described in the Examples below and known to those of ordinary skill in the art.

Accordingly, the present invention includes a wheat plant comprising one or more IMI nucleic acids, wherein the wheat plant has increased resistance to an imidazolinone herbicide as compared to a wild-type variety of the plant and wherein the one or more IMI nucleic acids are selected from a group consisting of an Imi1, Imi2 and Imi3 nucleic acid. In one embodiment, the plant comprises an Imi1 nucleic acid and an Imi3 nucleic acid. In a preferred embodiment, the Imi1 nucleic acid comprises the polynucleotide sequence shown in SEQ ID NO:1. In another embodiment, the plant comprises an Imi2 nucleic acid. In a preferred embodiment, the Imi2 nucleic acid comprises the polynucleotide sequence shown in SEQ ID NO:3.

As used herein with regard to nucleic acids, the term "from" refers to a nucleic acid "located on" or "derived from" a particular genome. The term "located on" refers to a nucleic acid contained within that particular genome. As also used herein with regard to a genome, the term "derived from" refers to a nucleic acid that has been removed or isolated from that genome. The term "isolated" is defined in more detail below.

In another embodiment, the wheat plant comprises an IMI nucleic acid, wherein the nucleic acid is a non-Imi1 nucleic acid. The term "non-Imi1", refers to an IMI nucleic acid that is not a member of the Imi1 class as described above. Examples of nucleic acids from the Imi1 class are shown in rows 3, 4 and 5 of FIG. 8. One example of non-Imi1 nucleic acid is shown in row 5 of FIG. 8. Accordingly, in a preferred embodiment, the wheat plant comprises an IMI nucleic acid comprising the polynucleotide sequence encoding the polypeptide of SEQ ID NO:4. The polynucleotide sequence can comprise the sequence shown in SEQ ID NO:3.

The present invention includes wheat plants comprising one, two, three or more IMI nucleic acids, wherein the wheat plant has increased resistance to an imidazolinone herbicide as compared to a wild-type variety of the plant. The IMI nucleic acids can comprise a nucleotide sequence selected from the group consisting of a polynucleotide of SEQ ID NO:1; a polynucleotide of SEQ ID NO:3; a polynucleotide sequence encoding a polypeptide of SEQ ID NO:2; a polynucleotide sequence encoding a polypeptide of SEQ ID NO:4, a polynucleotide comprising at least 60 consecutive nucleotides of any of the aforementioned polynucleotides; and a polynucleotide complementary to any of the aforementioned polynucleotides.

The imidazolinone herbicide can be selected from, but is not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, or a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidazolin-2-yl)-nicotinic acid, 2-(4-isopropyl)-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate. The use of 5-ethyl-2-(4-isopropyl-4-methyl-5-oxo-2-imidazolin-2-yl)-nicotinic acid and 2-(4-isopropyl-4-methyl-5-oxo-2-imidazolin-2-yl)-5-(methoxymethyl)-nicotinic acid is preferred. The use of 2-(4-isopropyl-4-methyl-5-oxo-2-imidazolin-2-yl)-5-(methoxymethyl)-nicotinic acid is particularly preferred.

In one embodiment, the wheat plant comprises two IMI nucleic acids, wherein the nucleic acids are derived from or located on different wheat genomes. Preferably, one of the two nucleic acids is an Imi1 nucleic acid, and more preferably comprises the polynucleotide sequence of SEQ ID NO:1. In another embodiment, the wheat plant comprises one IMI nucleic acid, wherein the nucleic acid comprises the polynucleotide sequence of SEQ ID NO:1 or SEQ ID NO:3. In yet another embodiment, the wheat plant comprises three or more IMI nucleic acids wherein each nucleic acid is from a different genome. Preferably, at least one of the three IMI nucleic acids comprises a polynucleotide sequence selected from the group consisting of SEQ ID NO:1 and SEQ ID NO:3.

Figure 13:
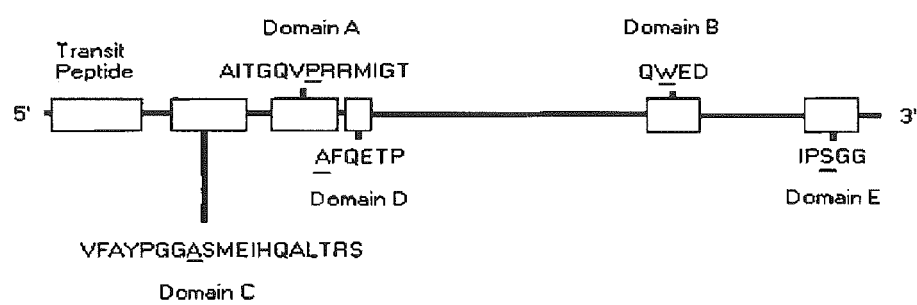
FIG. 13 is a schematic representation of the conserved amino acid sequences in the AHAS genes implicated in resistance to various AHAS inhibitors. The specific amino acid site responsible for resistance is indicated by an underline. (Modified from Devine, M. D. and Eberlein, C. V., 1997 Physiological, biochemical and molecular aspects of herbicide resistance based on altered target sites in Herbicide Activity Toxicity, Biochemistry, and Molecular Biology, IOS Press Amsterdam, p. 159-185).

In a preferred embodiment of the present invention, the one or more IMI nucleic acids contained within the plant encode an amino acid sequence comprising a mutation in a domain that is conserved among several AHAS proteins. These conserved domains are referred to herein as Domain A, Domain B, Domain C, Domain D and Domain E. FIG. 13 shows the general location of each domain in an AHAS protein. As used herein, Domain A contains the amino acid sequence AITGQVPRRMIGT (SEQ ID NO:8); Domain B contains the amino acid sequence QWED (SEQ ID NO:9); Domain C contains the amino acid sequence VFAYPGGAS-MEIHQALTRS (SEQ ID NO:10); Domain D contains the amino acid sequence AFQETP (SEQ ID NO:11); Domain E contains the amino acid sequence IPSGG (SEQ ID NO:12). The present invention also contemplates that there may be slight variations in the conserved domains, for example, in cockleberry plants, the serine residue in Domain E is replaced by an alanine residue.

Accordingly, the present invention includes a wheat plant comprising an IMI nucleic acid that encodes an amino acid sequence having a mutation in a conserved domain selected from the group consisting of a Domain A, a Domain B, a Domain C, a Domain D and a Domain E. In one embodiment, the wheat plant comprises an IMI nucleic acid that encodes an amino acid sequence having a mutation in a Domain E. In further preferred embodiments, the mutations in the conserved domains occur at the locations indicated by the following underlining: AITGQVPRRMIGT (SEQ ID NO:8); QWED (SEQ ID NO:9); VFAYPGGASMEIHQAL-TRS (SEQ ID NO:10); AFQETP (SEQ ID NO:11) and IPSGG (SEQ ID NO:12). One preferred substitution is asparagine for serine in Domain E (SEQ ID NO:12).

The wheat plants described herein can be either transgenic wheat plants or non-transgenic wheat plants. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding. Plants containing mutations arising due to non-spontaneous mutagenesis and selective breeding are referred to herein as non-transgenic plants and are included in the present invention. In embodiments wherein the wheat plant is transgenic and comprises multiple IMI nucleic acids, the nucleic acids can be derived from different genomes or the same genome. Alternatively, in embodiments wherein the wheat plant is non-transgenic and comprises multiple IMI nucleic acids, the nucleic acids are located on different genomes.

An example of a non-transgenic wheat plant cultivar comprising one IMI nucleic acid is the plant cultivar deposited with the ATCC under Patent Deposit Designation Number PTA-3953 and designated herein as the TealIMI 11A wheat cultivar. The TealIMI 11A wheat cultivar contains an Imi2 nucleic acid. The partial nucleotide and deduced amino acid sequences corresponding to the TealIMI2 11A gene are shown in SEQ ID NO:3 and SEQ ID NO:4, respectively. The only portion of the sequences not included in SEQ ID NO:3 and SEQ ID NO:4 are those sequences encoding and corresponding to a signal sequence that is cleaved from the mature TealIMI2 11A protein. Accordingly, SEQ ID NO:4 represents the full deduced sequence of the mature TealIMI2 11A protein.

An example of a wheat plant cultivar comprising two IMI nucleic acids on different genomes is the plant cultivar deposited with the ATCC under Patent Deposit Designation Number PTA-3955 and designated herein as the TealIMI 15A wheat cultivar. The TealIMI 15A wheat cultivar contains Imi1 and Imi3 nucleic acids. The Imi1 nucleic acid comprises a mutation that results in a serine to asparagine change in the IMI protein encoded thereby. The mutated AHAS genes are designated herein as TealIMI 15A and TealIMI3 15A. The partial nucleotide and deduced amino acid sequences corresponding to the TealIMI 15A gene are shown in SEQ ID NO:1 and SEQ ID NO:2, respectively. The only portion of the sequences not included in SEQ ID NO:1 and SEQ ID NO:2 are those sequences encoding and corresponding to approximately 100-150 base pairs at the 5' end and approximately 5 base pairs at the 3' end of the coding region.

Separate deposits of 2500 seeds of the TealIMI 11A and TealIMI 15A wheat cultivars were made with the American Type Culture Collection, Manassas, Va. on Jan. 3, 2002. These deposits were made in accordance with the terms and provisions of the Budapest Treaty relating to the deposit of microorganisms. The deposits were made for a term of at least thirty years and at least five years after the most recent request for the furnishing of a sample of the deposit is received by the ATCC. The deposited seeds were accorded Patent Deposit Designation Numbers PTA-3953 (TealIMI 11A) and PTA-3955 (TealIMI 15A).

The present invention includes the wheat plant having a Patent Deposit Designation Number PTA-3953 or PTA-3955; a mutant, recombinant, or genetically engineered derivative of the plant with Patent Deposit Designation Number PTA-3953 or PTA-3955; any progeny of the plant with Patent Deposit Designation Number PTA-3953 or PTA-3955; and a plant that is the progeny of any of these plants. In a preferred embodiment, the wheat plant of the present invention additionally has the herbicide resistance characteristics of the plant with Patent Deposit Designation Number PTA-3953 or PTA-3955.

Also included in the present invention are hybrids of the TealIMI 11A and TealIMI 15A wheat cultivars described herein. Example 5 demonstrates TealIMI11A/TealIMI15A hybrids having increased resistance to an imidazolinone herbicide. The present invention further includes hybrids of the TealIMI 11A or TealIMI 15A wheat cultivars and another wheat cultivar. The other wheat cultivar includes, but is not limited to, T. aestivum L. cv Fidel and any wheat cultivar harboring a mutant gene FS-1, FS-2, FS-3 or FS-4. (See U.S. Pat. No. 6,339,184 and U.S. patent application Ser. No. 08/474,832). In a preferred embodiment, the wheat plant is a hybrid between a TealIMI 11A cultivar and a Fidel FS-4 cultivar. The TealIMI 11A/FS-4 hybrids comprise an Imi1 nucleic acid and an Imi2 nucleic acid. A hybrid of TealIMI 11A and a Fidel cultivar harboring the FS-4 gene is included in the present invention and was deposited with the American Type Culture Collection, Manassas, Va. on Jan. 3, 2002. This deposit was made in accordance with the terms and provisions of the Budapest Treaty relating to the deposit of microorganisms. The deposit was made for a term of at least thirty years and at least five years after the most recent request for the furnishing of a sample of the deposit is received by the ATCC. The deposited seeds were accorded Patent Deposit Designation Number PTA-3954.

The terms "cultivar" and "variety" refer to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci.

A cultivar or variety is considered "true breeding" for a particular trait if, when the true-breeding cultivar or variety is self-pollinated, all of the progeny contain the trait. In the present invention, the trait arises from a mutation in an AHAS gene of the wheat plant or seed.

It is to be understood that the wheat plant of the present invention can comprise a wild type or non-mutated AHAS gene in addition to an IMI gene. As described in Example 4, it is contemplated that wheat cultivar TealIMI 11A contains a mutation in only one of multiple AHAS isoenzymes and that wheat cultivar TealIMI 15A contains a mutation in only two of multiple AHAS isoenzymes. Therefore, the present invention includes a wheat plant comprising one or more IMI nucleic acids in addition to one or more wild type or non-mutated AHAS nucleic acids.

In addition to wheat plants, the present invention encompasses isolated IMI proteins and nucleic acids. The nucleic acids comprise a polynucleotide selected from the group consisting of a polynucleotide of SEQ ID NO:1; a polynucleotide of SEQ ID NO:3; a polynucleotide sequence encoding a polypeptide of SEQ ID NO:2; a polynucleotide sequence encoding a polypeptide of SEQ ID NO:4, a polynucleotide comprising at least 60 consecutive nucleotides of any of the aforementioned polynucleotides; and a polynucleotide complementary to any of the aforementioned polynucleotides. In a preferred embodiment, the IMI nucleic acid comprises a polynucleotide sequence encoding a polypeptide of SEQ ID NO:2 or SEQ ID NO:4. In a further preferred embodiment, the IMI nucleic acid comprises a polynucleotide sequence of SEQ ID NO:1 or SEQ ID NO:3.

The term "AHAS protein" refers to an acetohydroxyacid synthase protein and the term "IMI protein" refers to any AHAS protein that is mutated from a wild type AHAS protein and that confers increased imidazolinone resistance to a plant, plant cell, plant part, plant seed or plant tissue when it is expressed therein. In a preferred embodiment, the IMI protein comprises a polypeptide of SEQ ID NO:2 or SEQ ID NO:4. As also used herein, the terms "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. In various embodiments, the isolated IMI nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Triticum aestivum* cell). A nucleic acid is also considered isolated if it has been altered by human intervention, or placed in a locus or location that is not its natural site, or if it is introduced into a cell by agroinfection or biolistics. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule containing a nucleotide sequence of SEQ ID NO:1, SEQ ID NO:3 or a portion thereof, can be isolated using standard molecular biology techniques and the sequence information provided herein. For example, a *T. aestivum* IMI cDNA can be isolated from a *T. aestivum* library using all or a portion of the sequence of SEQ ID NO:1 or SEQ ID NO:3. Moreover, a nucleic acid molecule encompassing all or a portion of SEQ ID NO:1 or SEQ ID NO:3 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1 or SEQ ID NO:3. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an IMI nucleotide sequence can be prepared by standard synthetic techniques, e.g., using an automated DNA synthesizer.

The IMI nucleic acids of the present invention can comprise sequences encoding an IMI protein (i.e., "coding regions"), as well as 5' untranslated sequences and 3' untranslated sequences. Alternatively, the nucleic acid molecules of the present invention can comprise only the coding regions of an IMI gene, or can contain whole genomic fragments isolated from genomic DNA. A coding region of these sequences is indicated as an "ORF position". Moreover, the nucleic acid molecule of the invention can comprise a portion of a coding region of an IMI gene, for example, a fragment that can be used as a probe or primer. The nucleotide sequences determined from the cloning of the IMI genes from *T. aestivum* allow for the generation of probes and primers designed for use in identifying and/or cloning IMI homologs in other cell types and organisms, as well as IMI homologs from other wheat plants and related species. The portion of the coding region can also encode a biologically active fragment of an IMI protein.

As used herein, the term "biologically active portion of" an IMI protein is intended to include a portion, e.g., a domain/motif, of an IMI protein that, when produced in a plant increases the plant's resistance to an imidazolinone herbicide as compared to a wild-type variety of the plant. Methods for quantitating increased resistance to imidazolinone herbicides are provided in the Examples provided below. Biologically active portions of an IMI protein include peptides encoded by polynucleotide sequences comprising SEQ ID NO:1 or SEQ ID NO:3 which include fewer amino acids than a full length IMI protein and impart increased resistance to an imidazolinone herbicide upon expression in a plant. Typically, biologically active portions (e.g., peptides which are, for example, 5, 10, 15, 20, 30, 35, 36, 37, 38, 39, 40, 50, 100 or more amino acids in length) comprise a domain or motif with at least one activity of an IMI protein. Moreover, other biologically active portions in which other regions of the polypeptide are deleted, can be prepared by recombinant techniques and evaluated for one or more of the activities described herein. Preferably, the biologically active portions of an IMI protein include one or more conserved domains selected from the group consisting of a Domain A, a Domain B, a Domain C, a Domain D and a Domain E, wherein the conserved domain contains a mutation.

The invention also provides IMI chimeric or fusion polypeptides. As used herein, an IMI "chimeric polypeptide" or "fusion polypeptide" comprises an IMI polypeptide operatively linked to a non-IMI polypeptide. A "non-IMI polypeptide" refers to a polypeptide having an amino acid sequence that is not substantially identical to an IMI polypeptide, e.g., a polypeptide that is not an IMI isoenzyme, which peptide performs a different function than an IMI polypeptide. Within the fusion polypeptide, the term "operatively linked" is intended to indicate that the IMI polypeptide and the non-IMI polypeptide are fused to each other so that both sequences fulfill the proposed function attributed to the sequence used. The non-IMI polypeptide can be fused to the N-terminus or C-terminus of the IMI polypeptide. For example, in one embodiment, the fusion polypeptide is a GST-IMI fusion polypeptide in which the IMI sequence is fused to the C-terminus of the GST sequence. Such fusion polypeptides can facilitate the purification of recombinant IMI polypeptides. In another embodiment, the fusion polypeptide is an IMI polypeptide containing a heterologous signal sequence at its N-terminus. In certain host cells (e.g., mammalian host cells), expression and/or secretion of an IMI polypeptide can be increased through use of a heterologous signal sequence.

An isolated nucleic acid molecule encoding an IMI polypeptide having sequence identity to a polypeptide encoded by a polynucleotide sequence of SEQ ID NO:1 or SEQ ID NO:3 can be created by introducing one or more nucleotide substitutions, additions or deletions into a nucleotide sequence of SEQ ID NO:1 or SEQ ID NO:3 such that one or more amino acid substitutions, additions or deletions are introduced into the encoded polypeptide. Mutations can be introduced into a sequence of SEQ ID NO:1 or SEQ ID NO:3 by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an IMI polypeptide is preferably replaced with another amino acid residue from the same side chain family. Alternatively, in another embodiment, mutations can be introduced randomly along all or part of an IMI coding sequence, such as by saturation mutagenesis, and the resultant mutants can be screened for an IMI activity described herein to identify mutants that retain IMI activity. Following mutagenesis of the sequence of SEQ ID NO:1 or SEQ ID NO:3, the encoded polypeptide can be expressed recombinantly and the activity of the polypeptide can be determined by analyzing the imidazolinone resistance of a plant expressing the polypeptide as described in the Examples below.

To determine the percent sequence identity of two amino acid sequences (e.g., SEQ ID NO:2 or SEQ ID NO:4 and a mutant form thereof), the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence (e.g., SEQ ID NO:2 or SEQ ID NO:4) is occupied by the same amino acid residue as the corresponding position in the other sequence (e.g., a mutant form of SEQ ID NO:2 or SEQ ID NO:4), then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. It is to be understood that for the purposes of determining sequence identity, when comparing a DNA sequence to an RNA sequence, a thymidine nucleotide is equivalent to a uracil nucleotide. Preferably, the isolated IMI polypeptides included in the present invention are at least about 50-60%, preferably at least about 60-70%, and more preferably at least about 70-75%, 75-80%, 80-85%, 85-90% or 90-95%, and most preferably at least about 96%, 97%, 98%, 99% or more identical to an entire amino acid sequence encoded by a polynucleotide sequence shown in SEQ ID NO:1 or SEQ ID NO:3. In another embodiment, the isolated IMI polypeptides included in the present invention are at least about 50-60%, preferably at least about 60-70%, and more preferably at least about 70-75%, 75-80%, 80-85%, 85-90% or 90-95%, and most preferably at least about 96%, 97%, 98%, 99% or more identical to an entire amino acid sequence shown in SEQ ID NO:2 or SEQ ID NO:4.

Additionally, optimized IMI nucleic acids can be created. Preferably, an optimized IMI nucleic acid encodes an IMI polypeptide that modulates a plant's tolerance to imidazolinone herbicides, and more preferably increases a plant's tolerance to an imidazolinone herbicide upon its overexpression in the plant. As used herein, "optimized" refers to a nucleic acid that is genetically engineered to increase its expression in a given plant or animal. To provide plant optimized IMI nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) eliminate sequences that cause destabilization, inappropriate polyadenylation, degradation and termination of RNA, or that form secondary structure hairpins or RNA splice sites. Increased expression of IMI nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991 Proc. Natl. Acad. Sci. USA 88:3324-3328; and Murray et al., 1989 Nucleic Acids Res. 17:477-498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation 1A=n 1 Z $X_n$−$Y_n$ $X_n$ times 100 Z where $X_n$=frequency of usage for codon n in the host cell; $Y_n$=frequency of usage for codon n in the synthetic gene, n represents an individual codon that specifies an amino acid and the total number of codons is Z. The overall deviation of the frequency of codon usage, A, for all amino acids should preferably be less than about 25%, and more preferably less than about 10%.

Hence, an IMI nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized IMI nucleic acids of this invention also preferably have CG and TA doublet avoidance indices closely approximating those of the chosen host plant (i.e., *Triticum aestivum*). More preferably these indices deviate from that of the host by no more than about 10-15%.

In addition to the nucleic acid molecules encoding the IMI polypeptides described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation and/or stability of the target polynucleotide. Methods are described in the prior art for targeting the antisense polynucleotide to the chromosomal DNA, to a primary RNA transcript or to a processed mRNA. Preferably, the target regions include splice sites, translation initiation codons, translation termination codons, and other sequences within the open reading frame.

The term "antisense", for the purposes of the invention, refers to a nucleic acid comprising a polynucleotide that is sufficiently complementary to all or a portion of a gene, primary transcript or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide encoded by the polynucleotide sequence of SEQ ID NO:1 or SEQ ID NO:3.

In addition to the IMI nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of the sequence set forth in SEQ ID NO:1 or SEQ ID NO:3, an anti-sense sequence of the sequence set forth in SEQ ID NO:1 or SEQ ID NO:3, or naturally occurring mutants thereof. Primers based on a nucleotide sequence of SEQ ID NO:1 or SEQ ID NO:3 can be used in PCR reactions to clone IMI homologs. Probes based on the IMI nucleotide sequences can be used to detect transcripts or genomic sequences encoding the same or homologous polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an IMI polypeptide, such as by measuring a level of an IMI-encoding nucleic acid, in a sample of cells, e.g., detecting IMI mRNA levels or determining whether a genomic IMI gene has been mutated or deleted.

The invention further provides an isolated recombinant expression vector comprising an IMI nucleic acid as described above, wherein expression of the vector in a host cell results in increased resistance to an imidazolinone herbicide as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., IMI polypeptides, fusion polypeptides, etc.).

In a preferred embodiment of the present invention, the IMI polypeptides are expressed in plants and plants cells such as unicellular plant cells (such as algae) (see Falciatore et al., 1999 Marine Biotechnology 1(3):239-251 and references therein) and plant cells from higher plants (e.g., the spermatophytes, such as crop plants). An IMI polynucleotide may be "introduced" into a plant cell by any means, including transfection, transformation or transduction, electroporation, particle bombardment, biolistics, agroinfection and the like. One transformation method known to those of skill in the art is the dipping of a flowering plant into an Agrobacteria solution, wherein the Agrobacteria contains the IMI nucleic acid, followed by breeding of the transformed gametes.

Other suitable methods for transforming or transfecting host cells including plant cells can be found in Sambrook, et al. (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As increased resistance to imidazolinone herbicides is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover.

In one embodiment of the present invention, transfection of an IMI polynucleotide into a plant is achieved by *Agrobacterium* mediated gene transfer. *Agrobacterium* mediated plant transformation can be performed using for example the GV3101 (pMP90) (Koncz and Schell, 1986 Mol. Gen. Genet. 204:383-396) or LBA4404 (Clontech) *Agrobacterium tumefaciens* strain. Transformation can be performed by standard transformation and regeneration techniques (Deblaere et al., 1994 Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-27314; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of antibiotica for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13:282-285. Additionally, transformation of soybean can be performed using, for example, a technique described in European Patent No. 0424 047, U.S. Pat. No. 5,322,783, European Patent No. 0397 687, U.S. Pat. No. 5,376,543 or 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

According to the present invention, the introduced IMI polynucleotide may be maintained in the plant cell stably if it is incorporated into a non-chromosomal autonomous replicon or integrated into the plant chromosomes. Alternatively, the introduced IMI polynucleotide may be present on an extra-chromosomal non-replicating vector and be transiently expressed or transiently active. In one embodiment, a homologous recombinant microorganism can be created wherein the IMI polynucleotide is integrated into a chromosome, a vector is prepared which contains at least a portion of an AHAS gene into which a deletion, addition or substitution has been introduced to thereby alter, e.g., functionally disrupt, the endogenous AHAS gene and to create an IMI gene. To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist 87(3):240-247). Other homologous recombination procedures in *Triticum* species are also well known in the art and are contemplated for use herein.

In the homologous recombination vector, the IMI gene can be flanked at its 5' and 3' ends by an additional nucleic acid molecule of the AHAS gene to allow for homologous recombination to occur between the exogenous IMI gene carried by the vector and an endogenous AHAS gene, in a microorganism or plant. The additional flanking AHAS nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95(8):4368-4373 for cDNA based recombination in *Physcomitrella patens*). However, since the IMI gene normally differs from the AHAS gene at very few amino acids, a flanking sequence is not always necessary. The homologous recombination vector is introduced into a microorganism or plant cell (e.g., via polyethylene glycol mediated DNA), and cells in which the introduced IMI gene has homologously recombined with the endogenous AHAS gene are selected using art-known techniques.

In another embodiment, recombinant microorganisms can be produced that contain selected systems that allow for regulated expression of the introduced gene. For example, inclusion of an IMI gene on a vector placing it under control of the lac operon permits expression of the IMI gene only in the presence of IPTG. Such regulatory systems are well known in the art.

Whether present in an extra-chromosomal non-replicating vector or a vector that is integrated into a chromosome, the IMI polynucleotide preferably resides in a plant expression cassette. A plant expression cassette preferably contains regulatory sequences capable of driving gene expression in plant cells that are operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof, but also all other terminators functionally active in plants are suitable. As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the polypeptide per RNA ratio (Gallie et al., 1987 Nucl. Acids Research 15:8693-8711). Examples of plant expression vectors include those detailed in: Becker, D. et al., 1992 New plant binary vectors with selectable markers located proximal to the left border, Plant Mol. Biol. 20:1195-1197; Bevan, M. W., 1984 Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operably linked to an appropriate promoter conferring gene expression in a timely, cell or tissue specific manner. Promoters useful in the expression cassettes of the invention include any promoter that is capable of initiating transcription in a plant cell. Such promoters include, but are not limited to those that can be obtained from plants, plant viruses and bacteria that contain genes that are expressed in plants, such as *Agrobacterium* and *Rhizobium*.

The promoter may be constitutive, inducible, developmental stage-preferred, cell type-preferred, tissue-preferred or organ-preferred. Constitutive promoters are active under most conditions. Examples of constitutive promoters include the CaMV 19S and 35 S promoters (Odell et al. 1985 Nature 313:810-812), the sX CaMV 35S promoter (Kay et al. 1987 Science 236:1299-1302) the Sep1 promoter, the rice actin promoter (McElroy et al. 1990 Plant Cell 2:163-171), the *Arabidopsis* actin promoter, the ubiquitan promoter (Christensen et al. 1989 Plant Molec Biol. 18:675-689); pEmu (Last et al. 1991 Theor Appl Genet. 81:581-588), the figwort mosaic virus 35S promoter, the Smas promoter (Velten et al. 1984 EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock, the PPDK promoter is induced by light, the PR-1 promoter from tobacco, *Arabidopsis* and maize are inducible by infection with a pathogen, and the Adh1 promoter is induced by hypoxia and cold stress. Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397-404) and an ethanol inducible promoter (PCT Application No. WO 93/21334).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters and the like. Seed preferred promoters are preferentially expressed during seed development and/or germination. For example, seed preferred promoters can be embryo-preferred, endosperm preferred and seed coat-preferred. See Thompson et al. 1989 BioEssays 10:108. Examples of seed preferred promoters include, but are not limited to cellulose synthase (ce1A), Cim1, gamma-zein, globulin-1, maize 19 kD zein (cZ19B1) and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991 Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980) or the legumin B4 promoter (LeB4; Baeumlein et al., 1992 Plant Journal, 2(2):233-9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soy bean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat. Nos. 5,412,085 and 5,545,546) and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, Cell 43:729-736 (1985)).

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an IMI polynucleotide can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) an IMI polynucleotide. Accordingly, the invention further provides methods for producing IMI polypeptides using the host cells of the invention. In one embodiment, the method comprises culturing the host cell of invention (into which a recombinant expression vector encoding an IMI polypeptide has been introduced, or into which genome has been introduced a gene encoding a wild-type or IMI polypeptide) in a suitable medium until IMI polypeptide is produced. In another embodiment, the method further comprises isolating IMI polypeptides from the medium or the host cell. Another aspect of the invention pertains to isolated IMI polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of IMI polypeptide in which the polypeptide is separated from some of the cellular components of the cells in which it is naturally or recombinantly produced. In one embodiment, the language "substantially free of cellular material" includes preparations of an IMI polypeptide having less than about 30% (by dry weight) of non-IMI material (also referred to herein as a "contaminating polypeptide"), more preferably less than about 20% of non-IMI material, still more preferably less than about 10% of non-IMI material, and most preferably less than about 5% non-IMI material.

When the IMI polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of IMI polypeptide in which the polypeptide is separated from chemical precursors or other chemicals that are involved in the synthesis of the polypeptide. In one embodiment, the language "substantially free of chemical precursors or other chemicals" includes preparations of an IMI polypeptide having less than about 30% (by dry weight) of chemical precursors or non-IMI chemicals, more preferably less than about 20% chemical precursors or non-IMI chemicals, still more preferably less than about 10% chemical precursors or non-IMI chemicals, and most preferably less than about 5% chemical precursors or non-IMI chemicals. In preferred embodiments, isolated polypeptides, or biologically active portions thereof, lack contaminating polypeptides from the same organism from which the IMI polypeptide is derived. Typically, such polypeptides are produced by recombinant expression of, for example, a *Triticum aestivum* IMI polypeptide in plants other than *Triticum aestivum* or microorganisms such as *C. glutamicum*, ciliates, algae or fungi.

The IMI polynucleotide and polypeptide sequences of the invention have a variety of uses. The nucleic acid and amino acid sequences of the present invention can be used to transform plants, thereby modulating the plant's resistance to imidazolinone herbicides. Accordingly, the invention provides a method of producing a transgenic plant having increased tolerance to an imidazolinone herbicide comprising, (a) transforming a plant cell with one or more expression vectors comprising one or more IMI nucleic acids, and (b) generating from the plant cell a transgenic plant with an increased resistance to an imidazolinone herbicide as compared to a wild type variety of the plant. In one embodiment, the multiple IMI nucleic acids are derived from different genomes. Also included in the present invention are methods of producing a transgenic plant having increased tolerance to an imidazolinone herbicide comprising, (a) transforming a plant cell with an expression vector comprising an IMI nucleic acid, wherein the nucleic acid is a non-Imi1 nucleic acid and (b) generating from the plant cell a transgenic plant with an increased resistance to an imidazolinone herbicide as compared to a wild type variety of the plant.

The present invention includes methods of modifying a plant's tolerance to an imidazolinone herbicide comprising modifying the expression of one or more IMI nucleic acids. Preferably, the nucleic acids are located on or derived from different genomes. The plant's resistance to the imidazolinone herbicide can be increased or decreased as achieved by increasing or decreasing the expression of an IMI polynucleotide, respectively. Preferably, the plant's resistance to the imidazolinone herbicide is increased by increasing expression of an IMI polynucleotide. Expression of an IMI polynucleotide can be modified by any method known to those of skill in the art. The methods of increasing expression of IMI polynucleotides can be used wherein the plant is either transgenic or not transgenic. In cases when the plant is transgenic, the plant can be transformed with a vector containing any of the above described IMI coding nucleic acids, or the plant can be transformed with a promoter that directs expression of endogenous IMI polynucleotides in the plant, for example. The invention provides that such a promoter can be tissue specific or developmentally regulated. Alternatively, non-transgenic plants can have endogenous IMI polynucleotide expression modified by inducing a native promoter. The expression of polynucleotides comprising SEQ ID NO:1 or SEQ ID NO:3 in target plants can be accomplished by, but is not limited to, one of the following examples: (a) constitutive promoter, (b) chemical-induced promoter, and (c) engineered promoter over-expression with for example zinc-finger derived transcription factors (Greisman and Pabo, 1997 Science 275:657).

In a preferred embodiment, transcription of the IMI polynucleotide is modulated using zinc-finger derived transcription factors (ZFPs) as described in Greisman and Pabo, 1997 Science 275:657 and manufactured by Sangamo Biosciences, Inc. These ZFPs comprise both a DNA recognition domain and a functional domain that causes activation or repression of a target nucleic acid such as an IMI nucleic acid. Therefore, activating and repressing ZFPs can be created that specifically recognize the IMI polynucleotide promoters described above and used to increase or decrease IMI polynucleotide expression in a plant, thereby modulating the herbicide resistance of the plant.

As described in more detail above, the plants produced by the methods of the present invention can be monocots or dicots. The plants can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops, for example. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover. In a preferred embodiment, the plant is a wheat plant. In each of the methods described above, the plant cell includes, but is not limited to, a protoplast, gamete producing cell, and a cell that regenerates into a whole plant. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations.

As described above, the present invention teaches compositions and methods for increasing the imidazolinone resistance of a wheat plant or seed as compared to a wild-type variety of the plant or seed. In a preferred embodiment, the imidazolinone resistance of a wheat plant or seed is increased such that the plant or seed can withstand an imidazolinone herbicide application of preferably approximately 10-400 g ai ha$^{-1}$, more preferably 20-160 g ai ha$^{-1}$, and most preferably 40-80 g ai ha$^{-1}$. As used herein, to "withstand" an imidazolinone herbicide application means that the plant is either not killed or not injured by such application.

Additionally provided herein is a method of controlling weeds within the vicinity of a wheat plant, comprising applying an imidazolinone herbicide to the weeds and to the wheat plant, wherein the wheat plant has increased resistance to the imidazolinone herbicide as compared to a wild type variety of the wheat plant, and wherein the plant comprises one or more IMI nucleic acids. In one embodiment, the plant comprises multiple IMI nucleic acids located on or derived from different genomes. In another embodiment, the plant comprises a non-Imi1 nucleic acid. By providing for wheat plants having increased resistance to imidazolinone, a wide variety of formulations can be employed for protecting wheat plants from weeds, so as to enhance plant growth and reduce competition for nutrients. An imidazolinone herbicide can be used by itself for pre-emergence, post-emergence, pre-planting and at-planting control of weeds in areas surrounding the wheat plants described herein or an imidazolinone herbicide formulation can be used that contains other additives. The imidazolinone herbicide can also be used as a seed treatment. Additives found in an imidazolinone herbicide formulation include other herbicides, detergents, adjuvants, spreading agents, sticking agents, stabilizing agents, or the like. The imidazolinone herbicide formulation can be a wet or dry preparation and can include, but is not limited to, flowable powders, emulsifiable concentrates and liquid concentrates. The imidazolinone herbicide and herbicide formulations can be applied in accordance with conventional methods, for example, by spraying, irrigation, dusting, or the like.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Mutagenesis and Selection of Resistant Wheat Lines

Approximately 40,000 seeds of *Triticum aestivum* L. cv CDC Teal (Hughes and Hucl, 1993 Can. J. Plant Sci. 73:193-197) were mutagenized using modified procedures described by Washington and Sears (1970). Seeds were pre-soaked in distilled water for four hours, followed by treatment with 0.3% EMS for six hours. Seeds were rinsed continually with tap water for seven hours and allowed to dry for approximately four hours before being planted in the field. The $M_1$ plants were selfed and the seed was harvested in bulk. Approximately $2 \times 10^6$ $M_2$ plants were grown in the field the following year and were sprayed at the two leaf stage with imazamox at a rate of 40 g ai ha$^{-1}$ in a spray volume of 100 L ha$^{-1}$. Merge 0.05% (v/v) adjuvant was added to the spray solution. Six lines resistant to imazamox were selected and designated as lines 1A, 9A, 10A, 11A, 15A, and 16A. The $M_3$ and $M_4$ generations were grown in a walk-in growth chamber and plants resistant to imazamox were selected using rates of 20 g ai ha$^{-1}$. Resistant plants were selected in the $M_5$ generation after application of 40 g ai ha$^{-1}$ in the field. $M_5$ seed was homozygous for the trait, as progeny testing detected no segregation for resistance to imazamox.

Example 2

Methods Used to Determine Inheritance and Allelism of IMI Genes

To determine the genetic control of resistance to imazamox in the six wheat lines, reciprocal crosses between the six homozygous resistant $M_6$ lines and CDC Teal (susceptible to imazamox) were made. Randomly selected $F_1$ plants from each of the crosses were backcrossed to CDC Teal to form backcross (BC)$F_1$ populations. To investigate allelism, all possible inter-crosses between the six mutants and SWP965001 (Grandin/3*Fidel—FS-4) were made. SWP965001 is a spring wheat line that is homozygous for the FS-4 allele. Parental genotypes were grown in a walk-in growth chamber with a 16 hour photoperiod and a 24° C. day and 16° C. night temperature regime. Spikes that were ¾ emerged from the boot were emasculated and then pollinated 2-3 days after the emasculation date. Randomly selected $F_2$ plants from all segregating crosses were selfed to produce $F_{2:3}$ families. Parental, $F_1$, BCF$_1$, $F_2$ plants and $F_{2:3}$ families were tested for reaction to imazamox. All experiments were conducted in a walk-in growth chamber with a 16 hour photoperiod and a 23° C. day and 16° C. night temperature regime. A completely random design was used for all experiments. In experiments involving $F_{2:3}$ families, effort was taken to randomize both within and among families. The $F_1$ and $F_2$ populations were screened in the same experiment along with parental genotypes and CDC Teal as controls. Both the BCF$_1$ and $F_{2:3}$ populations were screened in two separate experiments along with appropriate parental genotypes as controls.

Herbicide treatments were applied to plants growing in 8×16 cell flats at the two leaf stage using a traveling cable sprayer calibrated to spray 100 L ha$^{-1}$. Imazamox was applied to plants at a rate of 20 g ai ha$^{-1}$ using an 8001 EVS nozzle at a pressure of 275 kPa. Merge surfactant (0.05% v/v) was added to the herbicide solution prior to application. Fifteen days after herbicide application, plants were rated based on parental reactions and were considered as resistant, intermediate, or susceptible. Resistant plants were phenotypically unaffected following herbicide treatment whereas intermediate plants were characterized by halted growth of the first two leaves, darkening (dark-green pigmentation) of the leaves, and the emergence of coleoptilar tillers. Susceptible plants were characterized by failure to develop new leaves, extensive leaf chlorosis, and eventually, plant death. For Mendelian analysis of the segregating populations, plants were scored into resistant and susceptible categories and tested for goodness of fit to various 1 gene, 2 gene and 3 gene models using chi-square analysis. For $F_2$ and BCF$_1$ plant data, intermediate reactions were included in the resistant reaction category. Yates correction for continuity was used to adjust the chi-square value when only a single degree of freedom was used in the chi-square analysis (Steele and Torrie 1980 Principles and procedures of statistics. McGraw-Hill, New York, N.Y. pp 633).

Example 3

Results Regarding Inheritance of IMI Genes

All resistant parents produced a similar phenotype when sprayed with 20 g ai ha$^{-1}$ of imazamox. (FIG. 1). Reciprocal crosses between the resistant lines and the susceptible parent (CDC Teal) resulted in $F_1$ plants that survived application of imazamox (FIG. 1), indicating that resistance to imazamox is a nuclear and not a cytoplasmic trait. With the exception of cross 15A×Teal, the $F_1$ plants resulting from each of the resistant lines crossed with CDC Teal displayed an intermediate reaction (FIG. 1). Since the $F_1$ plants were phenotypically intermediate between the two parents, it was concluded that resistance to imazamox in these lines was a partially dominant trait (FIG. 1). Genetic analysis of resistance to imidazolinones and sulfonylureas in *Arabidopsis thaliana* (Haughn and Somerville, 1986 Mol. Gen. Genet. 204:430-434) *Zea mays* (Newhouse et al., 1991 Theor. Appl. Genet. 83:65-70), *Brassica napus* (Swanson et al., 1989 Theor. Appl. Gen. 78:525-530), and *Glycine max* (Sebastian et al., 1989 Crop Sci. 29:1403-1408) also indicated the presence of a single, partially dominant nuclear gene.

Fourteen $F_1$ plants resulting from the 15A×Teal cross were rated as resistant (FIG. 1). Evaluation of $F_2$ populations from this cross indicated that two independently segregating loci were involved in conferring resistance in this genotype (FIG. 2). Since the $F_1$ would carry two heterozygous resistant loci, one would expect that a resistant reaction would be observed. If each of these loci alone would confer partial dominance, additively, two heterozygous loci would produce a resistant reaction. Swanson et al. (1989) combined two semi-dominant imidazolinone resistance alleles from *Brassica napus*, representing two unlinked genes, to produce a $F_1$ hybrid that was superior in imidazolinone resistance than either of the heterozygous lines alone. The authors concluded that resistance mechanisms are additive, and a higher level of resistance is observed in lines carrying more than one resistance allele.

An analysis of cytoplasmic inheritance was conducted in the $F_2$ generation by testing homogeneity of deviations from segregation ratios between the two reciprocal $F_2$ populations. Chi-square analysis revealed no significant deviations between reciprocal populations, confirming the absence of cytoplasmic inheritance (FIG. 2). Since cytoplasmic inheritance was absent, data from the two reciprocal populations was combined and a total chi-square on pooled $F_2$ data was calculated (FIG. 2).

With the exception of Teal×15A, all $F_2$ populations resulting from resistant×susceptible crosses gave a good fit to a 3:1 resistant susceptible ratio indicating segregation of a single major gene for resistance to imazamox (FIG. 2). When $F_1$ plants were crossed to the susceptible parent, resulting $BCF_1$ populations gave a good fit to a 1:1 resistant: susceptible ratio, confirming the single locus hypothesis (FIG. 2). The $F_2$ population data from the cross 15A×Teal fit a 15:1 resistant:susceptible ratio (P=0.08), indicating segregation of two independent, complementary genes (FIG. 2). The $BCF_1$ population gave good fit to a 3:1 resistant: susceptible ratio with a chi-square P value of 0.35, confirming the results of the $F_2$ (FIG. 2).

Since it is speculated from $F_2$ data that resistance in lines 1A, 9A, 10A, 11A, and 16A are controlled by a single major gene, $F_{2:3}$ families should segregate and fit a 1:2:1 homozygous resistance:segregating:homozygous susceptible family ratio. Evaluation of $F_{2:3}$ families indicated that crosses Teal×1A, Teal×9A, Teal×10A, Teal×11A, and Teal×16A all fit a 1:2:1 resistant:segregating:susceptible $F_{2:3}$ family ratio with chi-square P values of 0.64, 0.66, 0.52, 0.40, and 0.94, respectively (FIG. 3). These results confirm the results of the $F_2$ and $BCF_1$ data that resistance in lines 1A, 10A, 9A, 11A, and resistance in 16A is controlled by a single major gene. This pattern of inheritance is consistent with other findings that have reported the genetic control of resistance to AHAS inhibitor herbicides. To date, nearly all plant mutations conferring resistance to imidazolinones show that a single, partially dominant gene controls the resistance trait. In *Triticum aestivum, Zea mays, Glycine max, Arabidopsis thaliana*, and *Nicotiana tabacum*, resistance to AHAS inhibitors is inherited as a single partially dominant nuclear gene (Newhouse et al. 1991; Newhouse et al. 1992; Chaleff and Ray, 1984 Science 223:1148-1151; Sathasivan et al., 1991 Plant Physiol. 97:1044-1050). Plant resistance to AHAS inhibitor herbicides occurs mostly because of a single point mutation to the gene encoding the AHAS enzyme (Harms et al. 1992, Mol. Gen. Genet. 233:427-435; Winder and Spalding, 1988 Mol. Gen. Genet. 238:394-399).

The $F_2$ data resulting from the cross Teal×15A provided a good fit to a 15:1 resistant:susceptible ratio, suggesting segregation of two, independently segregating loci (FIG. 2). If this is the case, $F_{2:3}$ families should segregate and fit a 7:8:1 resistant:segregating:susceptible $F_{2:3}$ family ratio. $F_{2:3}$ families from the cross 15A×Teal did fit the expected 7:8:1 ratio (FIG. 3), confirming the results of the $F_2$ and $BCF_1$ populations that resistance in 15A is conferred by two, independent loci. To the inventor's knowledge, this is the first reported instance were two independently segregating imidazolinone resistant alleles were identified in a single line following seed mutagenesis.

Example 4

Results Regarding Allelism of IMI Genes

To determine the allelic relationships of resistance genes, all possible intercrosses between resistant lines were evaluated. No susceptible plants were observed in the $F_2$ populations resulting from the inter-crosses between lines SWP965001, 1A, 9A, 10A, 15A, and 16A (FIG. 4). Since these populations were not segregating, the resistance genes in these lines are either alleles at the FS-4 locus, or are very tightly linked. Since these populations were not segregating in the $F_2$ generation, $F_{2:3}$ families from these crosses were not evaluated.

All inter-crosses involving line 11A did segregate in the $F_2$ generation, indicating the presence of a unique resistance gene in 11A (FIG. 4). If two independently segregating resistance genes are present as the result of crossing two lines, each carrying a single resistance gene, a 15:1 resistant: susceptible ratio would be expected in the $F_2$ generation. In the $F_2$ generation, crosses SWP965001.times.11A, 1A.times.11A, 10A.times.11A, and 16A.times.11A fit the expected 15:1 resistant:susceptible ratio suggesting independent segregation of two major resistance genes (FIG. 4). $F_{2:3}$ family ratios from these crosses also gave a good fit to a 7:8:1 resistant:segregating:susceptible ratio, confirming the results obtained in the $F_2$ generation (FIG. 5). Cross 11A×9A did produce a segregating $F_2$ population, but the ratio did not fit a 15:1 segregation ratio due to an excess of susceptible segregants. Various other two gene hypotheses were tested, but all were found to be highly significant (Data not shown). Evaluation of $F_{2:3}$ families from this cross, however did give good fit to a 7:8:1 segregation ratio, indicating segregation of two independent genes (FIG. 5). These results confirm that the resistance gene in 11A is unique from those in lines SWP96001, 1A, 9A, 10A, and 16A.

Cross 11A×15A did produce a segregating $F_2$ population. Since 15A is carrying two resistance genes, one allelic to FS-4, a segregating $F_2$ population in cross 11A×15A would indicate the presence of three segregating genes. Segregating generations resulting from cross 15A×11A were tested for segregation of three independent loci. $F_2$ plants did fit the expected 63:1 resistant:susceptible ratio, indicating the segregation of three independent loci (FIG. 4). These results suggest that the second mutation in 15A is not allelic to the resistance gene in 11A. $F_{2:3}$ families were not screened as over 330 plants within each family would have to be screened in order to ensure an adequate power of test (Hanson, 1959 Agron. J. 51:711-716).

Three independent resistance loci have been identified, each with an allele conferring resistance to imazamox. Recommended rules for gene locus and allele symbolization have been published (McIntosh et al., 1998 Catalogue of Gene Symbols. Volume 5, Proceedings of the 9$^{th}$ International Wheat Genetics Symposium. Saskatoon, Saskatchewan). Non-allelic gene loci of an enzyme that catalyze the same reaction should be given the same symbol, corresponding to the trivial name of the enzyme. The trivial name for AHAS is ALS. Absent data to assign the loci to specific chromosomes and genomes, they should be designated in sequential series. The designation of the phenotype observed when changes occur in the gene resulting in a new allele should reflect that phenotype. Thus, it is proposed that the FS-4 imidazolinone resistance allele be designated as Imi1 and the locus it is at designated as Als1. Imi stands for imidazolinone resistance. This designation indicates that the gene is a dominant trait and it is the first allele identified. Segregating $F_2$ and $F_{2:3}$ population data suggests that 15A and 11A carry two new independent resistance alleles at different loci (FIGS. 2 and 3). The designations for these alleles are Imi2 for the 11A mutation at the Als2 locus and Imi3 for the second 15A mutation at the Als3 locus.

Identified herein are three independently segregating alleles conferring resistance to imazamox, namely Imi1 (1A, 9A, 10A, 15A and 16A), Imi2 (11A), and Imi3 (15A). It is proposed that each of the three identified alleles are associated with a different structural gene coding for herbicide-insensitive forms of AHAS. Since wheat is a hexaploid, multiple AHAS loci would be expected. Other polyploid species have been found to have more than one copy of AHAS. In *Nicotiana tabacum*, an allotetraploid, two AHAS genes have been identified and characterized (Mazur et al. 1987). Chaleff and Ray (1984) identified two independently segregating sulfonylurea resistance alleles in *Nicotiana tabacum*, each coding for an altered form of AHAS. *Zea mays* possesses two constitutively expressed identical AHAS genes (Fang et al., 1992 Plant Mol. Biol. 18:1185-1187). In allotetraploid *Brassica napus* and *Gossypium hirsutum*, an AHAS multi-gene family consisting of five and six members, respectively, is present (Rutledge et al., 1991 Mol. Gen. Genet. 229:31-40; Grula et al., 1995 Plant Mol. Biol. 28:837-846). Higher levels of resistance to herbicides have been observed in polyploid species when multiple resistance alleles are present. Swanson et al. (1989 Theor. Appl. Gen. 78:525-530) combined two unique imidazolinone resistance alleles from two homozygous *Brassica napus* lines resulting in progeny with a higher level of resistance than either homozygous line alone. Creason and Chaleff (1988 Theor. Appl. Genet. 76:177-182) identified *Nicotiana tabacum* plants homozygous for two mutations that conferred resistance to sulfonylureas. Plants homozygous for both mutations were five-fold more resistant to foliar applications of chlorsulfuron than were plants homozygous for each single mutation. The present invention proposes producing increased levels of resistance to an imidazolinone herbicide in wheat by combining any two or all three resistance alleles.

Example 5

Tolerance to Imidazolinone Herbicides in Teal11A, Teal15A and Teal11A/15A Hybrid The increased tolerance exhibited by Teal 11A and Teal 15A to 20 grams per hectare of imazamox has been exemplified in previous examples by the ability to distinguish tolerant from susceptible parental and segregant plants in inheritance studies. Teal 11A has been shown to confer similar levels of tolerance to imidazolinone herbicides to that conferred by the FS4 mutation in Fidel in various greenhouse and field comparisons. The similarity in tolerance is also reflected in comparing the in vitro activity of AHAS extracted from tolerant plants. This is possible because the tolerance in Teal 11A, Teal 15A, and FS4 is due to a mutation in the AHAS enzyme rendering it resistant to inhibition by imidazolinone herbicides. FIG. 6 indicates that the activity of AHAS enzyme extracted from Teal 11A and BW755, a line containing FS4, changes similarly as the rate of imazamox increases, and both have a higher percentage of active (resistant) enzyme at the highest concentration of imazamox than does the wild type check, Teal.

The presence of two IMI nucleic acids in Teal 15A provides increased tolerance to imidazolinone herbicides compared to a line such as BW755 carrying only one IMI nucleic acid. This increased tolerance is reflected both in less injury at higher herbicide rates, but in having more uninhibited AHAS enzyme activity. FIG. 7 illustrates that a 10× rate of imazamox (200 g/ha), all treated one gene plants were injured, while no two gene plants were injured. At all concentrations of imazamox in an in vitro assay of AHAS activity (FIG. 6), but particularly at the highest concentrations, Teal ISA had a higher percentage of active (resistant) enzyme than did either of the single gene lines, Teal11A and BW755.

Combining three non-allelic genes each conferring tolerance to imidazolinone herbicides results in greater tolerance than with only two non-allelic genes (FIG. 7). At a 30× rate, or 600 g/ha of imazamox, over half of plants sustained no injury in a still-segregating selfed population of Teal15A crossed with Teal11A, while all plants of the homozygous population of Teal15A sustained injury.

We claim:

1. A wheat plant comprising a wheat Imi2 and wheat Imi1 nucleic acid, wherein the plant was obtained by a process comprising crossing a wheat plant of line TealIMI 11A, a representative sample of seed of the line having been deposited with ATCC under Patent Deposit Designation Number PTA-3953, with another *Triticum* line, wherein the produced plant comprises:
   a) said Imi2 nucleic acid selected from the group consisting of:
      i) polynucleotides comprising SEQ ID NO:3; and
      ii) polynucleotides encoding polypeptides comprising SEQ ID NO:4;
   b) said Imi1 nucleic acid encoding an IMI polypeptide comprising a serine to asparagine substitution in Domain E of said IMI polypeptide; and
said plant exhibiting increased tolerance to an imidazolinone herbicide as compared to that of a corresponding wild-type plant.

2. The wheat plant of claim 1, wherein said Imi2 nucleic acid is identical to the Imi2 nucleic acid of a plant of line Teal 11A.

3. The wheat plant of claim 1, wherein said Imi2 nucleic acid comprises polynucleotides encoding an IMI2 polypeptide identical to the IMI2 polypeptide of a plant of line Teal 11A.

4. The wheat plant of claim 1, wherein said wheat plant exhibits tolerance to 200 g ai/ha imazamox.

5. The wheat plant of claim 1, wherein said wheat plant exhibits tolerance to 600 g ai/ha imazamox.

6. The wheat plant of claim 1, wherein the IMI polypeptide expressed from said Imi2 and Imi1 nucleic acids each contribute imidazolinone-tolerant AHAS activity to the plant.

7. A seed of the wheat plant of claim 1, wherein said seed comprises said Imi2 and said Imi1 nucleic acids.

8. The wheat plant of claim 1, wherein said Imi1 nucleic acid is selected from the group consisting of:
   c) polynucleotides comprising SEQ ID NO:19; and
   d) polynucleotides encoding polypeptides comprising SEQ ID NO:20.

9. The wheat plant of claim 1, wherein said Imi1 nucleic acid comprises SEQ ID NO:19.

10. The wheat plant of claim 1, wherein said Imi1 nucleic acid comprises polynucleotides encoding SEQ ID NO:20.

11. The wheat plant of claim 1, wherein said other *Triticum* line is FS4 or FS2.

12. The wheat plant of claim 1, wherein said imidazolinone herbicide comprises at least one of: imazethapyr, imazapic, imazamox, imazaquin, imazethabenz, or imazapyr.

13. The wheat plant of claim 1, wherein said imidazolinone herbicide comprises imazethapyr.

14. The wheat plant of claim 1, wherein said imidazolinone herbicide comprises imazamox.

15. A plant part of the plant of claim 1, wherein the plant part comprises the Imi2 and the Imi1 nucleic acid.

16. The seed of claim 7, wherein the seed further comprises a seed treatment.

17. The seed of claim 16, wherein said seed treatment comprises an imidazolinone herbicide.

18. The seed of claim 17, wherein said imidazolinone herbicide comprises at least one of: imazapyr, imazethapyr, imazapic, imazamox, imazaquin, or imazethabenz.

19. A method for controlling weeds within the vicinity of a wheat plant, comprising:
   (a) providing the treated seed of claim 16; and
   (b) growing a wheat plant from said seed;
thereby controlling the weeds in the vicinity thereof.

20. A method for controlling weeds within the vicinity of a wheat plant, comprising:
   (a) growing the wheat plant of claim 1; and
   (b) contacting said plant and weeds in the vicinity thereof with an effective amount of an AHAS-inhibiting herbicide to which the plant is tolerant;
thereby controlling the weeds.

21. The method of claim 20, wherein said AHAS-inhibiting herbicide comprises an imidazolinone herbicide.

22. The method of claim 21, wherein said imidazolinone herbicide comprises at least one of: imazapyr, imazethapyr, imazapic, imazamox, imazaquin, or imazethabenz.

* * * * *

SEQUENCE LISTING

```
<160> NUMBER OF SEQ ID NOS: 35

<210> SEQ ID NO 1
<211> LENGTH: 1675
<212> TYPE: DNA
<213> ORGANISM: Triticum aestivum
<220> FEATURE:
<221> NAME/KEY: CDS
<222> LOCATION: (2)..(1672)
<220> FEATURE:
<221> NAME/KEY: modified_base
<222> LOCATION: (764)
<223> OTHER INFORMATION: unknown nucleotide
<220> FEATURE:
<221> NAME/KEY: modified_base
<222> LOCATION: (1003)
<223> OTHER INFORMATION: unknown nucleotide
<220> FEATURE:
<221> NAME/KEY: modified_base
<222> LOCATION: (1006)
<223> OTHER INFORMATION: unknown nucleotide

<400> SEQUENCE: 1 c gac gtc ttc gcc tac ccc ggc ggc gcc tcc atg gag atc cac cag gcg    49
```

```
      Asp Val Phe Ala Tyr Pro Gly Gly Ala Ser Met Glu Ile His Gln Ala
      1               5                   10                  15 ctg acg cgc tcg ccc gtc atc acc aac cac ctc ttc cgc cac gag cag        97
Leu Thr Arg Ser Pro Val Ile Thr Asn His Leu Phe Arg His Glu Gln
             20                  25                  30 ggg gag gcg ttc gcg gcg tcc ggc tac gcc cgc gcg tcc ggc cgc gtc       145
Gly Glu Ala Phe Ala Ala Ser Gly Tyr Ala Arg Ala Ser Gly Arg Val
             35                  40                  45 ggc gtc tgc gtc gcc acc tcc ggc ccg ggg gcc acc aac ctc gtc tcc       193
Gly Val Cys Val Ala Thr Ser Gly Pro Gly Ala Thr Asn Leu Val Ser
     50                  55                  60 gcg ctc gcc gac gcc ctc ctc gac tcc atc ccc atg gtc gcc atc acg       241
Ala Leu Ala Asp Ala Leu Leu Asp Ser Ile Pro Met Val Ala Ile Thr
 65                  70                  75                  80 ggc cag gtc ccc cgc cgc atg atc ggc acg gac gcg ttc cag gag acg       289
Gly Gln Val Pro Arg Arg Met Ile Gly Thr Asp Ala Phe Gln Glu Thr
                 85                  90                  95 ccc ata gtg gag gtc acg cgc tcc atc acc aag cac aac tac ctg gtc       337
Pro Ile Val Glu Val Thr Arg Ser Ile Thr Lys His Asn Tyr Leu Val
            100                 105                 110 ctt gac gtg gag gat atc ccc cgc gtc atc cag gaa gcc ttc ttc ctt       385
Leu Asp Val Glu Asp Ile Pro Arg Val Ile Gln Glu Ala Phe Phe Leu
            115                 120                 125 gca tcc tct ggc cgc ccg ggg ccg gtg cta gtt gat atc ccc aag gac       433
Ala Ser Ser Gly Arg Pro Gly Pro Val Leu Val Asp Ile Pro Lys Asp
        130                 135                 140 atc cag cag cag atg gct gtg ccc gtc tgg gac act cca atg agt ttg       481
Ile Gln Gln Gln Met Ala Val Pro Val Trp Asp Thr Pro Met Ser Leu
145                 150                 155                 160 cca ggg tac atc gcc cgc ctg ccc aag cca cca tct act gaa tcg ctt       529
Pro Gly Tyr Ile Ala Arg Leu Pro Lys Pro Pro Ser Thr Glu Ser Leu
                165                 170                 175 gag cag gtc ctg cgt ctg gtt ggc gag tca cgg cgc cca att ctg tat       577
Glu Gln Val Leu Arg Leu Val Gly Glu Ser Arg Arg Pro Ile Leu Tyr
            180                 185                 190 gtt ggt ggt ggc tgc gct gcg tct ggc gag gag ttg cgc cgc ttt gtt       625
Val Gly Gly Gly Cys Ala Ala Ser Gly Glu Glu Leu Arg Arg Phe Val
            195                 200                 205 gag ctt act ggg att cca gtt aca act act ctg atg ggc ctt ggc aac       673
Glu Leu Thr Gly Ile Pro Val Thr Thr Thr Leu Met Gly Leu Gly Asn
        210                 215                 220 ttc ccc agc gac gac cca ctg tct ctg cgc atg ctt ggg atg cat ggc       721
Phe Pro Ser Asp Asp Pro Leu Ser Leu Arg Met Leu Gly Met His Gly
225                 230                 235                 240 act gtg tat gca aat tat gca gta gat aag gct gac ctg ttg ntc gca       769
Thr Val Tyr Ala Asn Tyr Ala Val Asp Lys Ala Asp Leu Leu Ile Ala
                245                 250                 255 ttt ggt gtg cgg ttt gat gat cgt gtg act ggg aaa atc gag gct ttt       817
Phe Gly Val Arg Phe Asp Asp Arg Val Thr Gly Lys Ile Glu Ala Phe
            260                 265                 270 gca agc agg tcc aag att gng cac att gac att gac cca gct gag att       865
Ala Ser Arg Ser Lys Ile Glu His Ile Asp Ile Asp Pro Ala Glu Ile
            275                 280                 285 ggc aag aac aag cag cca cat gtc tcc att tgt gca gat gtt aan ctt       913
Gly Lys Asn Lys Gln Pro His Val Ser Ile Cys Ala Asp Val Lys Leu
        290                 295                 300 gct tta cag ggg ttg aat gat cta tta aat ggg agc aaa gca caa cag       961
Ala Leu Gln Gly Leu Asn Asp Leu Leu Asn Gly Ser Lys Ala Gln Gln
305                 310                 315                 320
```

```
ggt ctg gat ttt ggt cca tgg cac aag gag ttg gat cag can aan agg      1009
Gly Leu Asp Phe Gly Pro Trp His Lys Glu Leu Asp Gln Gln Xaa Arg
                325                 330                 335 gag ttt cct cta gga ttc aag act ttt ggc gag gcc atc ccg ccg caa      1057
Glu Phe Pro Leu Gly Phe Lys Thr Phe Gly Glu Ala Ile Pro Pro Gln
            340                 345                 350 tat gct atc cag gta ctg gat gag ctg aca aaa ggg gag gcg atc att      1105
Tyr Ala Ile Gln Val Leu Asp Glu Leu Thr Lys Gly Glu Ala Ile Ile
        355                 360                 365 gcc act ggt gtt ggg cag cac cag atg tgg gcg gct cag tat tac act      1153
Ala Thr Gly Val Gly Gln His Gln Met Trp Ala Ala Gln Tyr Tyr Thr
    370                 375                 380 tac aag cgg cca cgg cag tgg ctg tct tcg tct ggt ttg ggg gca atg      1201
Tyr Lys Arg Pro Arg Gln Trp Leu Ser Ser Ser Gly Leu Gly Ala Met
385                 390                 395                 400 gga ttt ggg tta cca gct gca gct ggc gct gct gtg gcc aac cca ggt      1249
Gly Phe Gly Leu Pro Ala Ala Ala Gly Ala Ala Val Ala Asn Pro Gly
                405                 410                 415 gtt aca gtt gtt gac att gat ggt gat ggt agt ttc ctc atg aac att      1297
Val Thr Val Val Asp Ile Asp Gly Asp Gly Ser Phe Leu Met Asn Ile
            420                 425                 430 cag gag ttg gcg ttg atc cgc att gag aac ctc cca gtg aag gtg atg      1345
Gln Glu Leu Ala Leu Ile Arg Ile Glu Asn Leu Pro Val Lys Val Met
        435                 440                 445 ata ttg aac aac cag cat ctg gga atg gtg gtg cag tgg gag gat agg      1393
Ile Leu Asn Asn Gln His Leu Gly Met Val Val Gln Trp Glu Asp Arg
    450                 455                 460 ttt tac aag gcc aat cgg gcg cac aca tac ctt ggc aac cca gaa aat      1441
Phe Tyr Lys Ala Asn Arg Ala His Thr Tyr Leu Gly Asn Pro Glu Asn
465                 470                 475                 480 gag agt gag ata tat cca gat ttt gtg acg att gct aaa gga ttc aac      1489
Glu Ser Glu Ile Tyr Pro Asp Phe Val Thr Ile Ala Lys Gly Phe Asn
                485                 490                 495 gtt cca gca gtt cga gtg acg aag aag agc gaa gtc act gca gca atc      1537
Val Pro Ala Val Arg Val Thr Lys Lys Ser Glu Val Thr Ala Ala Ile
            500                 505                 510 aag aag atg ctt gag acc cca ggg cca tac ttg ttg gat atc ata gtc      1585
Lys Lys Met Leu Glu Thr Pro Gly Pro Tyr Leu Leu Asp Ile Ile Val
        515                 520                 525 ccg cat cag gag cac gtg ctg cct atg atc cca aac ggt ggt gct ttc      1633
Pro His Gln Glu His Val Leu Pro Met Ile Pro Asn Gly Gly Ala Phe
    530                 535                 540 aag gac atg atc atg gag ggt gat ggc agg acc tcg tac tga              1675
Lys Asp Met Ile Met Glu Gly Asp Gly Arg Thr Ser Tyr
545                 550                 555

<210> SEQ ID NO 2
<211> LENGTH: 557
<212> TYPE: PRT
<213> ORGANISM: Triticum aestivum

<400> SEQUENCE: 2

Asp Val Phe Ala Tyr Pro Gly Gly Ala Ser Met Glu Ile His Gln Ala
  1               5                  10                  15

Leu Thr Arg Ser Pro Val Ile Thr Asn His Leu Phe Arg His Glu Gln
             20                  25                  30

Gly Glu Ala Phe Ala Ala Ser Gly Tyr Ala Arg Ala Ser Gly Arg Val
         35                  40                  45

Gly Val Cys Val Ala Thr Ser Gly Pro Gly Ala Thr Asn Leu Val Ser
     50                  55                  60
```

```
Ala Leu Ala Asp Ala Leu Leu Asp Ser Ile Pro Met Val Ala Ile Thr
 65                  70                  75                  80

Gly Gln Val Pro Arg Met Ile Gly Thr Asp Ala Phe Gln Glu Thr
                 85                  90                  95

Pro Ile Val Glu Val Thr Arg Ser Ile Thr Lys His Asn Tyr Leu Val
                100                 105                 110

Leu Asp Val Glu Asp Ile Pro Arg Val Ile Gln Glu Ala Phe Phe Leu
                115                 120                 125

Ala Ser Ser Gly Arg Pro Gly Pro Val Leu Val Asp Ile Pro Lys Asp
                130                 135                 140

Ile Gln Gln Gln Met Ala Val Pro Val Trp Asp Thr Pro Met Ser Leu
145                 150                 155                 160

Pro Gly Tyr Ile Ala Arg Leu Pro Lys Pro Pro Ser Thr Glu Ser Leu
                165                 170                 175

Glu Gln Val Leu Arg Leu Val Gly Glu Ser Arg Arg Pro Ile Leu Tyr
                180                 185                 190

Val Gly Gly Gly Cys Ala Ala Ser Gly Glu Glu Leu Arg Arg Phe Val
                195                 200                 205

Glu Leu Thr Gly Ile Pro Val Thr Thr Thr Leu Met Gly Leu Gly Asn
210                 215                 220

Phe Pro Ser Asp Asp Pro Leu Ser Leu Arg Met Leu Gly Met His Gly
225                 230                 235                 240

Thr Val Tyr Ala Asn Tyr Ala Val Asp Lys Ala Asp Leu Leu Ile Ala
                245                 250                 255

Phe Gly Val Arg Phe Asp Asp Arg Val Thr Gly Lys Ile Glu Ala Phe
                260                 265                 270

Ala Ser Arg Ser Lys Ile Glu His Ile Asp Ile Asp Pro Ala Glu Ile
                275                 280                 285

Gly Lys Asn Lys Gln Pro His Val Ser Ile Cys Ala Asp Val Lys Leu
                290                 295                 300

Ala Leu Gln Gly Leu Asn Asp Leu Leu Asn Gly Ser Lys Ala Gln Gln
305                 310                 315                 320

Gly Leu Asp Phe Gly Pro Trp His Lys Glu Leu Asp Gln Gln Lys Arg
                325                 330                 335

Glu Phe Pro Leu Gly Phe Lys Thr Phe Gly Glu Ala Ile Pro Pro Gln
                340                 345                 350

Tyr Ala Ile Gln Val Leu Asp Glu Leu Thr Lys Gly Glu Ala Ile Ile
                355                 360                 365

Ala Thr Gly Val Gly Gln His Gln Met Trp Ala Ala Gln Tyr Tyr Thr
                370                 375                 380

Tyr Lys Arg Pro Arg Gln Trp Leu Ser Ser Ser Gly Leu Gly Ala Met
385                 390                 395                 400

Gly Phe Gly Leu Pro Ala Ala Gly Ala Ala Val Ala Asn Pro Gly
                405                 410                 415

Val Thr Val Val Asp Ile Asp Gly Asp Gly Ser Phe Leu Met Asn Ile
                420                 425                 430

Gln Glu Leu Ala Leu Ile Arg Ile Glu Asn Leu Pro Val Lys Val Met
                435                 440                 445

Ile Leu Asn Asn Gln His Leu Gly Met Val Val Gln Trp Glu Asp Arg
                450                 455                 460

Phe Tyr Lys Ala Asn Arg Ala His Thr Tyr Leu Gly Asn Pro Glu Asn
465                 470                 475                 480
```

```
Glu Ser Glu Ile Tyr Pro Asp Phe Val Thr Ile Ala Lys Gly Phe Asn
                485                 490                 495

Val Pro Ala Val Arg Val Thr Lys Lys Ser Glu Val Thr Ala Ala Ile
            500                 505                 510

Lys Lys Met Leu Glu Thr Pro Gly Pro Tyr Leu Leu Asp Ile Ile Val
        515                 520                 525

Pro His Gln Glu His Val Leu Pro Met Ile Pro Asn Gly Gly Ala Phe
    530                 535                 540

Lys Asp Met Ile Met Glu Gly Asp Gly Arg Thr Ser Tyr
545                 550                 555

<210> SEQ ID NO 3
<211> LENGTH: 1672
<212> TYPE: DNA
<213> ORGANISM: Triticum aestivum
<220> FEATURE:
<221> NAME/KEY: CDS
<222> LOCATION: (2)..(1669)

<400> SEQUENCE: 3 c gac gtc ttc gcc tac cct ggc ggc gcg tcc atg gag atc cac cag gcg        49
  Asp Val Phe Ala Tyr Pro Gly Gly Ala Ser Met Glu Ile His Gln Ala
  1               5                  10                  15 ctg acg cgc tcg cca gtc atc acc aac cac ctc ttc cgc cac gag cag        97
Leu Thr Arg Ser Pro Val Ile Thr Asn His Leu Phe Arg His Glu Gln
                20                  25                  30 ggg gag gcg ttc gcg gcg tcc ggg tac gcc cgc gcg tcc ggc cgc gtc       145
Gly Glu Ala Phe Ala Ala Ser Gly Tyr Ala Arg Ala Ser Gly Arg Val
            35                  40                  45 ggc gtc tgc gtc gcc acc tcc ggc ccg ggg gcc acc aac ctc gtc tcc       193
Gly Val Cys Val Ala Thr Ser Gly Pro Gly Ala Thr Asn Leu Val Ser
        50                  55                  60 gcg ctc gcc gac gct ctc ctc gac tcc atc ccc atg gtc gcc atc acg       241
Ala Leu Ala Asp Ala Leu Leu Asp Ser Ile Pro Met Val Ala Ile Thr
    65                  70                  75                  80 ggc cag gtc ccc cgc cgc atg atc ggc acg gat gcg ttc cag gag acg       289
Gly Gln Val Pro Arg Arg Met Ile Gly Thr Asp Ala Phe Gln Glu Thr
                85                  90                  95 ccc atc gtg gag gtc acg cgc tcc atc acc aag cac aac tac ctg gtc       337
Pro Ile Val Glu Val Thr Arg Ser Ile Thr Lys His Asn Tyr Leu Val
            100                 105                 110 ctt gac gtg gag gat atc ccc cgc gtc atc cag gaa gcc ttc ttc ctc       385
Leu Asp Val Glu Asp Ile Pro Arg Val Ile Gln Glu Ala Phe Phe Leu
        115                 120                 125 gca tcc tct ggc cgc ccg ggg ccg gtg ctg gtt gat atc ccc aag gac       433
Ala Ser Ser Gly Arg Pro Gly Pro Val Leu Val Asp Ile Pro Lys Asp
    130                 135                 140 atc cag cag cag atg gct gtg cct gtc tgg gac acg ccg atg agt ttg       481
Ile Gln Gln Gln Met Ala Val Pro Val Trp Asp Thr Pro Met Ser Leu
145                 150                 155                 160 cca ggg tac atc gcc cgc ctg ccc aag cca cca tct act gaa tcg ctt       529
Pro Gly Tyr Ile Ala Arg Leu Pro Lys Pro Pro Ser Thr Glu Ser Leu
                165                 170                 175 gag cag gtc ctg cgt ctg gtt ggc gag tca cgg cgc cca att ctg tat       577
Glu Gln Val Leu Arg Leu Val Gly Glu Ser Arg Arg Pro Ile Leu Tyr
            180                 185                 190 gtt ggt ggt ggc tgc gct gca tct ggt gag gag ttg cgc cgc ttt gtt       625
Val Gly Gly Gly Cys Ala Ala Ser Gly Glu Glu Leu Arg Arg Phe Val
        195                 200                 205 gag ctc act ggg att cca gtt aca act act ctt atg ggc ctt ggc aac       673
```

```
                Glu Leu Thr Gly Ile Pro Val Thr Thr Thr Leu Met Gly Leu Gly Asn
                    210                 215                 220 ttc ccc agt gac gac cca ctg tct ctg cgc atg ctg ggg atg cat ggc            721
Phe Pro Ser Asp Asp Pro Leu Ser Leu Arg Met Leu Gly Met His Gly
225                 230                 235                 240 act gtg tat gca aat tat gca gta gat aag gct gac ctg ttg ctt gca            769
Thr Val Tyr Ala Asn Tyr Ala Val Asp Lys Ala Asp Leu Leu Leu Ala
                245                 250                 255 ttt ggt gtg cgg ttt gat gat cgt gtg acc ggg aaa atc gag gct ttt            817
Phe Gly Val Arg Phe Asp Asp Arg Val Thr Gly Lys Ile Glu Ala Phe
        260                 265                 270 gca agc agg tcc aag att gtg cac att gac att gac cca gct gag att            865
Ala Ser Arg Ser Lys Ile Val His Ile Asp Ile Asp Pro Ala Glu Ile
275                 280                 285 ggc aag aac aag cag cca cat gtc tcc att tgt gca gat gtt aag ctt            913
Gly Lys Asn Lys Gln Pro His Val Ser Ile Cys Ala Asp Val Lys Leu
            290                 295                 300 gct tta cag ggg ttg aat gct cta tta aat ggg agc aaa gca caa cag            961
Ala Leu Gln Gly Leu Asn Ala Leu Leu Asn Gly Ser Lys Ala Gln Gln
305                 310                 315                 320 ggt ctg gat ttt ggt cca tgg cac aag gag ttg gat cag cag aag agg           1009
Gly Leu Asp Phe Gly Pro Trp His Lys Glu Leu Asp Gln Gln Lys Arg
                325                 330                 335 gag ttt cct cta gga ttc aag act ttt ggt gag gcc atc ccg ccg caa           1057
Glu Phe Pro Leu Gly Phe Lys Thr Phe Gly Glu Ala Ile Pro Pro Gln
            340                 345                 350 tat gct atc cag gta ctg gat gag ctg aca aaa ggg gag gcg atc att           1105
Tyr Ala Ile Gln Val Leu Asp Glu Leu Thr Lys Gly Glu Ala Ile Ile
        355                 360                 365 gcc acc ggt gtt ggg cag cat cag atg tgg gcg gct cag tat tac act           1153
Ala Thr Gly Val Gly Gln His Gln Met Trp Ala Ala Gln Tyr Tyr Thr
370                 375                 380 tac aag cgg cca cgg cag tgg ctg tct tca tcc ggt ttg ggt gca atg           1201
Tyr Lys Arg Pro Arg Gln Trp Leu Ser Ser Ser Gly Leu Gly Ala Met
385                 390                 395                 400 gga ttt ggg ttg cca gct gca gct ggc gct gct gtg gcc aac cca ggt           1249
Gly Phe Gly Leu Pro Ala Ala Ala Gly Ala Ala Val Ala Asn Pro Gly
                405                 410                 415 gtt aca gtt gtt gac att gat ggg gat ggt agt ttc ctc atg aac att           1297
Val Thr Val Val Asp Ile Asp Gly Asp Gly Ser Phe Leu Met Asn Ile
            420                 425                 430 cag gag ttg gcg ttg atc cgt att gag aac ctc cca gtg aag gtg atg           1345
Gln Glu Leu Ala Leu Ile Arg Ile Glu Asn Leu Pro Val Lys Val Met
        435                 440                 445 ata ttg aac aac cag cat ctg gga atg gtg gtg cag tgg gag gat agg           1393
Ile Leu Asn Asn Gln His Leu Gly Met Val Val Gln Trp Glu Asp Arg
450                 455                 460 ttt tac aag gcc aac cgg gcg cac aca tac ctt ggc aac cca gaa aat           1441
Phe Tyr Lys Ala Asn Arg Ala His Thr Tyr Leu Gly Asn Pro Glu Asn
465                 470                 475                 480 gag agt gag ata tat cca gat ttt gtg acg att gct aaa gga ttc aac           1489
Glu Ser Glu Ile Tyr Pro Asp Phe Val Thr Ile Ala Lys Gly Phe Asn
                485                 490                 495 gtt ccg gca gtt cgt gtg acg aag aag agc gaa gtc act gca gca atc           1537
Val Pro Ala Val Arg Val Thr Lys Lys Ser Glu Val Thr Ala Ala Ile
            500                 505                 510 aag aag atg ctt gag acc cca ggg cca tac ttg ttg gat atc att gtc           1585
Lys Lys Met Leu Glu Thr Pro Gly Pro Tyr Leu Leu Asp Ile Ile Val
        515                 520                 525
```

```
ccg cat cag gag cac gtg ctg cct atg atc cca aac ggt ggt gct ttt      1633
Pro His Gln Glu His Val Leu Pro Met Ile Pro Asn Gly Gly Ala Phe
    530             535             540 aag gac atg atc atg gag ggt gat ggc agg acc tcg tac                   1672
Lys Asp Met Ile Met Glu Gly Asp Gly Arg Thr Ser
545             550             555
```

<210> SEQ ID NO 4
<211> LENGTH: 556
<212> TYPE: PRT
<213> ORGANISM: Triticum aestivum

<400> SEQUENCE: 4

```
Asp Val Phe Ala Tyr Pro Gly Gly Ala Ser Met Glu Ile His Gln Ala
1               5                   10                  15

Leu Thr Arg Ser Pro Val Ile Thr Asn His Leu Phe Arg His Glu Gln
            20                  25                  30

Gly Glu Ala Phe Ala Ala Ser Gly Tyr Ala Arg Ala Ser Gly Arg Val
        35                  40                  45

Gly Val Cys Val Ala Thr Ser Gly Pro Gly Ala Thr Asn Leu Val Ser
    50                  55                  60

Ala Leu Ala Asp Ala Leu Leu Asp Ser Ile Pro Met Val Ala Ile Thr
65                  70                  75                  80

Gly Gln Val Pro Arg Arg Met Ile Gly Thr Asp Ala Phe Gln Glu Thr
                85                  90                  95

Pro Ile Val Glu Val Thr Arg Ser Ile Thr Lys His Asn Tyr Leu Val
            100                 105                 110

Leu Asp Val Glu Asp Ile Pro Arg Val Ile Gln Glu Ala Phe Phe Leu
        115                 120                 125

Ala Ser Ser Gly Arg Pro Gly Pro Val Leu Val Asp Ile Pro Lys Asp
    130                 135                 140

Ile Gln Gln Gln Met Ala Val Pro Val Trp Asp Thr Pro Met Ser Leu
145                 150                 155                 160

Pro Gly Tyr Ile Ala Arg Leu Pro Lys Pro Pro Ser Thr Glu Ser Leu
                165                 170                 175

Glu Gln Val Leu Arg Leu Val Gly Glu Ser Arg Arg Pro Ile Leu Tyr
            180                 185                 190

Val Gly Gly Gly Cys Ala Ala Ser Gly Glu Glu Leu Arg Arg Phe Val
        195                 200                 205

Glu Leu Thr Gly Ile Pro Val Thr Thr Thr Leu Met Gly Leu Gly Asn
    210                 215                 220

Phe Pro Ser Asp Asp Pro Leu Ser Leu Arg Met Leu Gly Met His Gly
225                 230                 235                 240

Thr Val Tyr Ala Asn Tyr Ala Val Asp Lys Ala Asp Leu Leu Leu Ala
                245                 250                 255

Phe Gly Val Arg Phe Asp Asp Arg Val Thr Gly Lys Ile Glu Ala Phe
            260                 265                 270

Ala Ser Arg Ser Lys Ile Val His Ile Asp Ile Asp Pro Ala Glu Ile
        275                 280                 285

Gly Lys Asn Lys Gln Pro His Val Ser Ile Cys Ala Asp Val Lys Leu
    290                 295                 300

Ala Leu Gln Gly Leu Asn Ala Leu Leu Asn Gly Ser Lys Ala Gln Gln
305                 310                 315                 320

Gly Leu Asp Phe Gly Pro Trp His Lys Glu Leu Asp Gln Gln Lys Arg
                325                 330                 335
```

Glu Phe Pro Leu Gly Phe Lys Thr Phe Gly Glu Ala Ile Pro Pro Gln
                340                 345                 350

Tyr Ala Ile Gln Val Leu Asp Glu Leu Thr Lys Gly Glu Ala Ile Ile
            355                 360                 365

Ala Thr Gly Val Gly Gln His Gln Met Trp Ala Ala Gln Tyr Tyr Thr
        370                 375                 380

Tyr Lys Arg Pro Arg Gln Trp Leu Ser Ser Gly Leu Gly Ala Met
385                 390                 395                 400

Gly Phe Gly Leu Pro Ala Ala Gly Ala Ala Val Ala Asn Pro Gly
                405                 410                 415

Val Thr Val Val Asp Ile Asp Gly Asp Gly Ser Phe Leu Met Asn Ile
            420                 425                 430

Gln Glu Leu Ala Leu Ile Arg Ile Glu Asn Leu Pro Val Lys Val Met
        435                 440                 445

Ile Leu Asn Asn Gln His Leu Gly Met Val Val Gln Trp Glu Asp Arg
    450                 455                 460

Phe Tyr Lys Ala Asn Arg Ala His Thr Tyr Leu Gly Asn Pro Glu Asn
465                 470                 475                 480

Glu Ser Glu Ile Tyr Pro Asp Phe Val Thr Ile Ala Lys Gly Phe Asn
                485                 490                 495

Val Pro Ala Val Arg Val Thr Lys Lys Ser Glu Val Thr Ala Ala Ile
            500                 505                 510

Lys Lys Met Leu Glu Thr Pro Gly Pro Tyr Leu Leu Asp Ile Ile Val
        515                 520                 525

Pro His Gln Glu His Val Leu Pro Met Ile Pro Asn Gly Gly Ala Phe
    530                 535                 540

Lys Asp Met Ile Met Glu Gly Asp Gly Arg Thr Ser
545                 550                 555

<210> SEQ ID NO 5
<211> LENGTH: 1524
<212> TYPE: DNA
<213> ORGANISM: Triticum aestivum

<400> SEQUENCE: 5
gtctgcgtcg ccacctccgg cccgggggcc accaacctcg tctccgcgct cgccgacgcc        60
ctcctcgact ccatcccat ggtcgccatc acgggccagg tccccgccg catgatcggc         120 acggacgcgt tccaggagac gcccatagtg gaggtcacgc gctccatcac caagcacaac       180
tacctggtcc ttgacgtgga ggatatcccc cgcgtcatcc aggaagcctt cttccttgca       240
tcctctggcc gcccggggcc ggtgctagtt gatatcccca aggacatcca gcagcagatg       300
gctgtgcccg tctgggacac tccaatgagt ttgccagggt cacatcgcccg cctgcccaag       360 ccaccatcta ctgaatcgct tgagcaggtc ctgcgtctgg ttggcgagtc acggcgccca       420
attctgtatg ttggtggtgg ctgcgctgcg tctggcgagg agttgcgccg ctttgttgag       480
cttactggga ttccagttac aactactctg atgggccttg caacttccc cagcgacgac        540 ccactgtctc tgcgcatgct tgggatgcat ggcactgtgt atgcaaatta tgcagtagat       600
aaggctgacc tgttgctcgc atttggtgtg cggtttgatg atcgtgtgac tgggaaaatc       660
gaggcttttg caagcaggtc caagattgtg cacattgaca ttgacccagc tgagattggc       720
aagaacaagc agccacatgt ctccatttgt gcagatgtta agcttgcttt acaggggttg       780
aatgatctat taaatgggag caaagcacaa caggtctgg attttggtcc atggcacaag       840
gagttggatc agcagaagag ggagtttcct ctaggattca agacttttgg cgaggccatc       900

```
ccgccgcaat atgctatcca ggtactggat gagctgacaa aaggggaggc gatcattgcc      960
actggtgttg ggcagcacca gatgtgggcg gctcagtatt acacttacaa gcggccacgg     1020
cagtggctgt cttcgtctgg tttgggggca atgggatttg ggttaccagc tgcagctggc     1080
gctgctgtgg ccaacccagg tgttacagtt gttgacattg atggtgatgg tagtttcctc     1140
atgaacattc aggagttggc gttgatccgc attgagaacc tcccagtgaa ggtgatgata     1200
ttgaacaacc agcatctggg aatggtggtg cagtgggagg ataggtttta caaggccaat     1260
cgggcgcaca catccttgg caacccagaa aatgagagtg agatatatcc agattttgtg      1320
acgattgcta aaggattcaa cgttccagca gttcgagtga cgaagaagag cgaagtcact     1380
gcagcaatca agaagatgct tgagacccca gggccatact tgttggatat catagtcccg     1440
catcaggagc acgtgctgcc tatgatccca agcggtggtg ctttcaagga catgatcatg     1500
gagggtgatg gcaggacctc gtac                                            1524

<210> SEQ ID NO 6
<211> LENGTH: 1524
<212> TYPE: DNA
<213> ORGANISM: Triticum aestivum

<400> SEQUENCE: 6
gtctgcgtcg ccacctccgg cccgggggcc accaacctcg tctccgcgct cgccgacgct       60
ctcctcgact ccatccccat ggtcgccatc acgggccagg tcccccgccg catgatcggc      120
acggatgcgt tccaggagac gcccatcgtg gaggtcacgc gctccatcac caagcacaac      180
tacctggtcc ttgacgtgga ggatatcccc cgcgtcatcc aggaagcctt cttcctcgca      240
tcctctggcc gccgggggcc ggtgctggtt gatatcccca aggacatcca gcagcagatg      300
gctgtgcctg tctgggacac gccgatgagt ttgccagggt acatcgcccg cctgcccaag      360
ccaccatcta ctgaatcgct tgagcaggtc ctgcgtctgg ttggcgagtc acggcgccca      420
attctgtatg ttggtggtgg ctgcgctgca tctggtgagg agttgcgccg ctttgttgag      480
ctcactggga ttccagttac aactactctt atgggccttg gcaacttccc cagtgacgac      540
ccactgtctc tgcgcatgct ggggatgcat ggcactgtgt atgcaaatta tgcagtagat      600
aaggctgacc tgttgcttgc atttggtgtg cggtttgatg atcgtgtgac cgggaaaatc      660
gaggcttttg caagcaggtc caagattgtg cacattgaca ttgacccagc tgagattggc      720
aagaacaagc agccacatgt ctccatttgt gcagatgtta agcttgcttt acaggggttg      780
aatgctctat taaatgggag caaagcacaa cagggtctgg attttggtcc atggcacaag      840
gagttggatc agcagaagag ggagtttcct ctaggattca agacttttgg tgaggccatc      900
ccgccgcaat atgctatcca ggtactggat gagctgacaa aaggggaggc gatcattgcc      960
accggtgttg ggcagcatca gatgtgggcg gctcagtatt acacttacaa gcggccacgg     1020
cagtggctgt cttcatccgg tttgggtgca atgggatttg ggttgccagc tgcagctggc     1080
gctgctgtgg ccaacccagg tgttacagtt gttgacattg atggggatgg tagtttcctc     1140
atgaacattc aggagttggc gttgatccgt attgagaacc tcccagtgaa ggtgatgata     1200
ttgaacaacc agcatctggg aatggtggtg cagtgggagg ataggtttta caaggccaac     1260
cgggcgcaca catccttgg caacccagaa aatgagagtg agatatatcc agattttgtg      1320
acgattgcta aaggattcaa cgttccggca gttcgtgtga cgaagaagag cgaagtcact     1380
gcagcaatca agaagatgct tgagacccca gggccatact tgttggatat cattgtcccg     1440
```

```
catcaggagc acgtgctgcc tatgatccca agcggtggtg cttttaagga catgatcatg    1500
gagggtgatg gcaggacctc gtac                                           1524

<210> SEQ ID NO 7
<211> LENGTH: 1524
<212> TYPE: DNA
<213> ORGANISM: Triticum aestivum

<400> SEQUENCE: 7
gtctgcgtcg ccacctccgg cccgggggcc accaacctcg tctccgcgct cgctgacgcc      60
ctcctcgact ccatccccat ggtcgccatc acgggccagg tccccgccg catgatcggc      120 acggacgcgt tccaggagac gcccatagtg gaggtcacgc gctccatcac caagcacaac     180
tacctggtcc ttgacgtgga ggatatcccc cgcgtcatcc aggaagcctt cttcctcgcg    240
tcctctggcc gcccggggcc ggtgctggtt gatatcccca aggatatcca gcagcagatg    300
gccgtgccta tctgggacac gccgatgagt ttgccagggt acatcgcccg cctgcccaag    360
ccaccatcta ctgaatcgct tgagcaggtc ctgcgtctgg ttggcgagtc acggcgccca    420
attctgtatg ttggtggtgg ctgcgctgca tccggcgagg agttgcgccg ctttgttgag    480
ctcactggga ttccggttac aactactctg atgggccttg caacttccc cagcgacgac     540 ccactgtctc tgcgcatgct tgggatgcat ggcactgtgt atgcaaatta tgcagtcgat    600
aaggctgacc tgttgcttgc atttggtgtg cggtttgatg atcgcgtgac tgggaaaatc    660
gaggcctttg caagcaggtc caagattgtg cacattgaca ttgacccagc tgagattggc    720
aagaacaagc agccacatgt ctccatttgt gcagatgtta agcttgcttt acaggggttg    780
aatgctctat taaatgggag caaagcacaa cagggtctgg attttggtcc atggcacaag    840
gagttggatc agcagaagag ggagtttcct ctaggattca agacttttgg cgaggccatc    900
ccgccgcaat atgctatcca ggtactggat gagctgacaa aggggaggc gatcattgct    960 actggtgttg gcagcacca gatgtgggcg gctcagtatt acacttacaa gcggccacgg    1020
cagtggctgt cttcgtctgg tttgggggca atgggatttg ggttaccagc tgcagctggc   1080
gctgctgtgg ccaacccagg tgttacagtt gttgacattg atggagatgg tagtttcctc   1140
atgaacattc aggagttggc attgatccgt attgagaacc tccctgtgaa ggtgatgata   1200
ttgaacaacc agcatctggg aatggtggtg caatgggagg ataggttta caaggccaat   1260 cgggcgcaca catacctggg caacccagaa atgagagtg agatatatcc agattttgtg   1320
acgattgcta aaggattcaa cgttccggca gttcgtgtga cgaagaagag cgaagtcact   1380
gcagcaatca agaagatgct tgagaccccca gggccatact tgttggatat catcgtcccg   1440
catcaggagc acgtgctgcc tatgatccca agcggtggtg cttctcaagga catgatcatg   1500 gagggtgatg gcaggacctc gtac                                           1524

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 8

Ala Ile Thr Gly Gln Val Pro Arg Arg Met Ile Gly Thr
 1               5                   10
```

```
<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 9

Gln Trp Glu Asp
  1

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 10

Val Phe Ala Tyr Pro Gly Gly Ala Ser Met Glu Ile His Gln Ala Leu
  1               5                  10                  15

Thr Arg Ser

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 11

Ala Phe Gln Glu Thr Pro
  1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 12

Ile Pro Ser Gly Gly
  1               5

<210> SEQ ID NO 13
<211> LENGTH: 1935
<212> TYPE: DNA
<213> ORGANISM: Oryza sp.
<220> FEATURE:
<221> NAME/KEY: CDS
<222> LOCATION: (1)..(1932)

<400> SEQUENCE: 13 atg gct acg acc gcc gcg gcc gcg gcc gcc gcc ctg tcc gcc gcc gcg      48
Met Ala Thr Thr Ala Ala Ala Ala Ala Ala Ala Leu Ser Ala Ala Ala
  1               5                  10                  15 acg gcc aag acc ggc cgt aag aac cac cag cga cac cac gtc ctt ccc      96
Thr Ala Lys Thr Gly Arg Lys Asn His Gln Arg His His Val Leu Pro
                 20                  25                  30 gct cga ggc cgg gtg ggg gcg gcg gcg gtc agg tgc tcg gcg gtg tcc     144
Ala Arg Gly Arg Val Gly Ala Ala Ala Val Arg Cys Ser Ala Val Ser
             35                  40                  45
```

-continued

| | | |
|---|---|---|
| ccg gtc acc ccg ccg tcc ccg gcg ccg ccg gcc acg ccg ctc cgg ccg<br>Pro Val Thr Pro Pro Ser Pro Ala Pro Pro Ala Thr Pro Leu Arg Pro<br>50                        55                        60 | 192 |
| tgg ggg ccg gcc gag ccc cgc aag ggc gcg gac atc ctc gtg gag gcg<br>Trp Gly Pro Ala Glu Pro Arg Lys Gly Ala Asp Ile Leu Val Glu Ala<br>65                        70                        75                        80 | 240 |
| ctg gag cgg tgc ggc gtc agc gac gtg ttc gcc tac ccg ggc ggc gcg<br>Leu Glu Arg Cys Gly Val Ser Asp Val Phe Ala Tyr Pro Gly Gly Ala<br>                      85                        90                        95 | 288 |
| tcc atg gag atc cac cag gcg ctg acg cgc tcc ccg gtc atc acc aac<br>Ser Met Glu Ile His Gln Ala Leu Thr Arg Ser Pro Val Ile Thr Asn<br>                 100                      105                      110 | 336 |
| cac ctc ttc cgc cac gag cag ggc gag gcg ttc gcg gcg tcc ggg tac<br>His Leu Phe Arg His Glu Gln Gly Glu Ala Phe Ala Ala Ser Gly Tyr<br>          115                      120                      125 | 384 |
| gcg cgc gcg tcc ggc cgc gtc ggg gtc tgc gtc gcc acc tcc ggc ccc<br>Ala Arg Ala Ser Gly Arg Val Gly Val Cys Val Ala Thr Ser Gly Pro<br>130                        135                        140 | 432 |
| ggg gca acc aac ctc gtg tcc gcg ctc gcc gac gcg ctg ctc gac tcc<br>Gly Ala Thr Asn Leu Val Ser Ala Leu Ala Asp Ala Leu Leu Asp Ser<br>145                        150                        155                      160 | 480 |
| gtc ccg atg gtc gcc atc acg ggc cag gtc ccc cgc cgc atg atc ggc<br>Val Pro Met Val Ala Ile Thr Gly Gln Val Pro Arg Arg Met Ile Gly<br>                        165                      170                      175 | 528 |
| acc gac gcc ttc cag gag acg ccc ata gtc gag gtc acc cgc tcc atc<br>Thr Asp Ala Phe Gln Glu Thr Pro Ile Val Glu Val Thr Arg Ser Ile<br>                 180                      185                      190 | 576 |
| acc aag cac aat tac ctt gtc ctt gat gtg gag gac atc ccc cgc gtc<br>Thr Lys His Asn Tyr Leu Val Leu Asp Val Glu Asp Ile Pro Arg Val<br>          195                      200                      205 | 624 |
| ata cag gaa gcc ttc ttc ctc gcg tcc tcg ggc cgt cct ggc ccg gtg<br>Ile Gln Glu Ala Phe Phe Leu Ala Ser Ser Gly Arg Pro Gly Pro Val<br>210                        215                        220 | 672 |
| ctg gtc gac atc ccc aag gac atc cag cag cag atg gcc gtg ccg gtc<br>Leu Val Asp Ile Pro Lys Asp Ile Gln Gln Gln Met Ala Val Pro Val<br>225                        230                        235                      240 | 720 |
| tgg gac acc tcg atg aat cta cca ggg tac atc gca cgc ctg ccc aag<br>Trp Asp Thr Ser Met Asn Leu Pro Gly Tyr Ile Ala Arg Leu Pro Lys<br>                 245                      250                      255 | 768 |
| cca ccc gcg aca gaa ttg ctt gag cag gtc ttg cgt ctg gtt ggc gag<br>Pro Pro Ala Thr Glu Leu Leu Glu Gln Val Leu Arg Leu Val Gly Glu<br>                 260                      265                      270 | 816 |
| tca cgg cgc ccg att ctc tat gtc ggt ggt ggc tgc tct gca tct ggt<br>Ser Arg Arg Pro Ile Leu Tyr Val Gly Gly Gly Cys Ser Ala Ser Gly<br>          275                      280                      285 | 864 |
| gac gaa ttg cgc tgg ttt gtt gag ctg act ggt atc cca gtt aca acc<br>Asp Glu Leu Arg Trp Phe Val Glu Leu Thr Gly Ile Pro Val Thr Thr<br>290                        295                        300 | 912 |
| act ctg atg ggc ctc ggc aat ttc ccc agt gac gac ccg ttg tcc ctg<br>Thr Leu Met Gly Leu Gly Asn Phe Pro Ser Asp Asp Pro Leu Ser Leu<br>305                        310                        315                      320 | 960 |
| cgc atg ctt ggg atg cat ggc acg gtg tac gca aat tat gcc gtg gat<br>Arg Met Leu Gly Met His Gly Thr Val Tyr Ala Asn Tyr Ala Val Asp<br>                 325                      330                      335 | 1008 |
| aag gct gac ctg ttg ctt gcg ttt ggt gtg cgg ttt gat gat cgt gtg<br>Lys Ala Asp Leu Leu Leu Ala Phe Gly Val Arg Phe Asp Asp Arg Val<br>          340                      345                      350 | 1056 |
| aca ggg aaa att gag gct ttt gca agc agg gcc aag att gtg cac att<br>Thr Gly Lys Ile Glu Ala Phe Ala Ser Arg Ala Lys Ile Val His Ile | 1104 |

```
                355                 360                 365
gac att gat cca gca gag att gga aag aac aag caa cca cat gtg tca        1152
Asp Ile Asp Pro Ala Glu Ile Gly Lys Asn Lys Gln Pro His Val Ser
370                 375                 380 att tgc gca gat gtt aag ctt gct tta cag ggc ttg aat gct ctg cta        1200
Ile Cys Ala Asp Val Lys Leu Ala Leu Gln Gly Leu Asn Ala Leu Leu
385                 390                 395                 400 caa cag agc aca aca aag aca agt tct gat ttt agt gca tgg cac aat        1248
Gln Gln Ser Thr Thr Lys Thr Ser Ser Asp Phe Ser Ala Trp His Asn
            405                 410                 415 gag ttg gac cag cag aag agg gag ttt cct ctg ggg tac aaa act ttt        1296
Glu Leu Asp Gln Gln Lys Arg Glu Phe Pro Leu Gly Tyr Lys Thr Phe
        420                 425                 430 ggt gaa gag atc cca ccg caa tat gcc att cag gtg ctg gat gag ctg        1344
Gly Glu Glu Ile Pro Pro Gln Tyr Ala Ile Gln Val Leu Asp Glu Leu
    435                 440                 445 acg aaa ggt gag gca atc atc gct act ggt gtt ggg cag cac cag atg        1392
Thr Lys Gly Glu Ala Ile Ile Ala Thr Gly Val Gly Gln His Gln Met
450                 455                 460 tgg gcg gca caa tat tac acc tac aag cgg cca cgg cag tgg ctg tct        1440
Trp Ala Ala Gln Tyr Tyr Thr Tyr Lys Arg Pro Arg Gln Trp Leu Ser
465                 470                 475                 480 tcg gct ggt ctg ggc gca atg gga ttt ggg ctg cct gct gca gct ggt        1488
Ser Ala Gly Leu Gly Ala Met Gly Phe Gly Leu Pro Ala Ala Ala Gly
            485                 490                 495 gct tct gtg gct aac cca ggt gtc aca gtt gtt gat att gat ggg gat        1536
Ala Ser Val Ala Asn Pro Gly Val Thr Val Val Asp Ile Asp Gly Asp
        500                 505                 510 ggt agc ttc ctc atg aac att cag gag ctg gca ttg atc cgc att gag        1584
Gly Ser Phe Leu Met Asn Ile Gln Glu Leu Ala Leu Ile Arg Ile Glu
    515                 520                 525 aac ctc cct gtg aag gtg atg gtg ttg aac aac caa cat ttg ggt atg        1632
Asn Leu Pro Val Lys Val Met Val Leu Asn Asn Gln His Leu Gly Met
530                 535                 540 gtg gtg caa tgg gag gat agg ttt tac aag gcg aat agg gcg cat aca        1680
Val Val Gln Trp Glu Asp Arg Phe Tyr Lys Ala Asn Arg Ala His Thr
545                 550                 555                 560 tac ttg ggc aac ccg gaa tgt gag agc gag ata tat cca gat ttt gtg        1728
Tyr Leu Gly Asn Pro Glu Cys Glu Ser Glu Ile Tyr Pro Asp Phe Val
            565                 570                 575 act att gct aag ggg ttc aat att cct gca gtc cgt gta aca aag aag        1776
Thr Ile Ala Lys Gly Phe Asn Ile Pro Ala Val Arg Val Thr Lys Lys
        580                 585                 590 agt gaa gtc cgt gcc gcc atc aag aag atg ctc gag act cca ggg cca        1824
Ser Glu Val Arg Ala Ala Ile Lys Lys Met Leu Glu Thr Pro Gly Pro
    595                 600                 605 tac ttg ttg gat atc atc gtc ccg cac cag gag cat gtg ctg cct atg        1872
Tyr Leu Leu Asp Ile Ile Val Pro His Gln Glu His Val Leu Pro Met
610                 615                 620 atc cca agt ggg ggc gca ttc aag gac atg atc ctg gat ggt gat ggc        1920
Ile Pro Ser Gly Gly Ala Phe Lys Asp Met Ile Leu Asp Gly Asp Gly
625                 630                 635                 640 agg act gtg tat taa                                                    1935
Arg Thr Val Tyr <210> SEQ ID NO 14
<211> LENGTH: 644
<212> TYPE: PRT
<213> ORGANISM: Oryza sp.
```

<400> SEQUENCE: 14

```
Met Ala Thr Thr Ala Ala Ala Ala Ala Leu Ser Ala Ala Ala
1               5                   10                  15

Thr Ala Lys Thr Gly Arg Lys Asn His Gln Arg His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
                100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
        130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
            245                 250                 255

Pro Pro Ala Thr Glu Leu Leu Glu Gln Val Leu Arg Leu Val Gly Glu
        260                 265                 270

Ser Arg Arg Pro Ile Leu Tyr Val Gly Gly Gly Cys Ser Ala Ser Gly
    275                 280                 285

Asp Glu Leu Arg Trp Phe Val Glu Leu Thr Gly Ile Pro Val Thr Thr
290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
            325                 330                 335

Lys Ala Asp Leu Leu Leu Ala Phe Gly Val Arg Phe Asp Asp Arg Val
        340                 345                 350

Thr Gly Lys Ile Glu Ala Phe Ala Ser Arg Ala Lys Ile Val His Ile
    355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
            405                 410                 415
```

| | | | | | | | | | | | | |
|---|---|---|---|---|---|---|---|---|---|---|---|---|
|Glu|Leu|Asp|Gln|Gln|Lys|Arg|Glu|Phe|Pro|Leu|Gly|Tyr|Lys|Thr|Phe|
| |420| | | | |425| | | | |430| |

Glu Leu Asp Gln Gln Lys Arg Glu Phe Pro Leu Gly Tyr Lys Thr Phe
　　　420　　　　　　　　425　　　　　　　　430

Gly Glu Glu Ile Pro Pro Gln Tyr Ala Ile Gln Val Leu Asp Glu Leu
　　　　　435　　　　　　　　440　　　　　　　　445

Thr Lys Gly Glu Ala Ile Ile Ala Thr Gly Val Gly Gln His Gln Met
450　　　　　　　　455　　　　　　　　460

Trp Ala Ala Gln Tyr Tyr Thr Tyr Lys Arg Pro Arg Gln Trp Leu Ser
465　　　　　　　　470　　　　　　　　475　　　　　　　　480

Ser Ala Gly Leu Gly Ala Met Gly Phe Gly Leu Pro Ala Ala Ala Gly
　　　　　　　　485　　　　　　　　490　　　　　　　　495

Ala Ser Val Ala Asn Pro Gly Val Thr Val Asp Ile Asp Gly Asp
　　　　　500　　　　　　　　505　　　　　　　　510

Gly Ser Phe Leu Met Asn Ile Gln Glu Leu Ala Leu Ile Arg Ile Glu
　　　　　515　　　　　　　　520　　　　　　　　525

Asn Leu Pro Val Lys Val Met Val Leu Asn Asn Gln His Leu Gly Met
　　530　　　　　　　　535　　　　　　　　540

Val Val Gln Trp Glu Asp Arg Phe Tyr Lys Ala Asn Arg Ala His Thr
545　　　　　　　　550　　　　　　　　555　　　　　　　　560

Tyr Leu Gly Asn Pro Glu Cys Glu Ser Glu Ile Tyr Pro Asp Phe Val
　　　　　565　　　　　　　　570　　　　　　　　575

Thr Ile Ala Lys Gly Phe Asn Ile Pro Ala Val Arg Val Thr Lys Lys
　　　　　580　　　　　　　　585　　　　　　　　590

Ser Glu Val Arg Ala Ala Ile Lys Lys Met Leu Glu Thr Pro Gly Pro
　　　　　595　　　　　　　　600　　　　　　　　605

Tyr Leu Leu Asp Ile Ile Val Pro His Gln Glu His Val Leu Pro Met
　　　610　　　　　　　　615　　　　　　　　620

Ile Pro Ser Gly Gly Ala Phe Lys Asp Met Ile Leu Asp Gly Asp Gly
625　　　　　　　　630　　　　　　　　635　　　　　　　　640

Arg Thr Val Tyr

<210> SEQ ID NO 15
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (681)
<223> OTHER INFORMATION: unknown nucleotide

<400> SEQUENCE: 15

```
gtc gac gtc ttc gcc tac ccc ggc ggc gcc tcc atg gag atc cac cag     48
Val Asp Val Phe Ala Tyr Pro Gly Gly Ala Ser Met Glu Ile His Gln
 1               5                  10                  15 gcg ctg acg cgc tcg ccc gtc atc acc aac cac ctc ttc cgc cac gag     96
Ala Leu Thr Arg Ser Pro Val Ile Thr Asn His Leu Phe Arg His Glu
             20                  25                  30 cag ggg gag gcg ttc gcg gcg tcc ggc tac gcc cgc gcg tcc ggc cgc    144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc    192
Val Gly Val Cys Val Ala Thr Ser Gly Pro Gly Ala Thr Asn Leu Val
     50                  55                  60 tcc gcg ctc gcc gac gcc ctc ctc gac tcc atc ccc atg gtc gcc atc    240
Ser Ala Leu Ala Asp Ala Leu Leu Asp Ser Ile Pro Met Val Ala Ile
 65                  70                  75                  80
```

```
acg ggc cag gtc ccc cgc cgc atg atc ggc acg gac gcg ttc cag gag        288
Thr Gly Gln Val Pro Arg Arg Met Ile Gly Thr Asp Ala Phe Gln Glu
                85                  90                  95 acg ccc ata gtg gag gtc acg cgc tcc atc acc aag cac aac tac ctg        336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc        384
Val Leu Asp Val Glu Asp Ile Pro Arg Val Ile Gln Glu Ala Phe Phe
        115                 120                 125 ctt gca tcc tct ggc cgc ccg ggg ccg gtg cta gtt gat atc ccc aag        432
Leu Ala Ser Ser Gly Arg Pro Gly Pro Val Leu Val Asp Ile Pro Lys
    130                 135                 140 gac atc cag cag cag atg gct gtg ccc gtc tgg gac act cca atg agt        480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg        528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg        576
Leu Glu Gln Val Leu Arg Leu Val Gly Glu Ser Arg Arg Pro Ile Leu
            180                 185                 190 tat gtt ggt ggt ggc tgc gct gcg tct ggc gag gag ttg cgc cgc ttt        624
Tyr Val Gly Gly Gly Cys Ala Ala Ser Gly Glu Glu Leu Arg Arg Phe
        195                 200                 205 gtt gag ctt act ggg att cca gtt aca act act ctg atg ggc ctt ggc        672
Val Glu Leu Thr Gly Ile Pro Val Thr Thr Thr Leu Met Gly Leu Gly
    210                 215                 220 aac ttc ccn agc gac gac cca ctg tct ctg cgc atg ctt ggg atg cat        720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ctc        768
Gly Thr Val Tyr Ala Asn Tyr Ala Val Asp Lys Ala Asp Leu Leu Leu
                245                 250                 255 gca ttt ggt gtg cgg ttt gat gat cgt gtg act ggg aaa atc gag gct        816
Ala Phe Gly Val Arg Phe Asp Asp Arg Val Thr Gly Lys Ile Glu Ala
            260                 265                 270 ttt gca agc agg tcc aag att gtg cac att gac att gac cca gct gag        864
Phe Ala Ser Arg Ser Lys Ile Val His Ile Asp Ile Asp Pro Ala Glu
        275                 280                 285 att ggc aag aac aag cag cca cat gtc tcc att tgt gca gat gtt aag        912
Ile Gly Lys Asn Lys Gln Pro His Val Ser Ile Cys Ala Asp Val Lys
    290                 295                 300 ctt gct tta cag ggg ttg aat gat cta tta aat ggg agc aaa gca caa        960
Leu Ala Leu Gln Gly Leu Asn Asp Leu Leu Asn Gly Ser Lys Ala Gln
305                 310                 315                 320 cag ggt ctg gat ttt ggt cca tgg cac aag gag ttg gat cag cag aag       1008
Gln Gly Leu Asp Phe Gly Pro Trp His Lys Glu Leu Asp Gln Gln Lys
                325                 330                 335 agg gag ttt cct cta gga ttc aag act ttt ggc gag gcc atc ccg ccg       1056
Arg Glu Phe Pro Leu Gly Phe Lys Thr Phe Gly Glu Ala Ile Pro Pro
            340                 345                 350 caa tat gct atc cag gta ctg gat gag ctg aca aaa ggg gag gcg atc       1104
Gln Tyr Ala Ile Gln Val Leu Asp Glu Leu Thr Lys Gly Glu Ala Ile
        355                 360                 365 att gcc act ggt gtt ggg cag cac cag atg tgg gcg gct cag tat tac       1152
Ile Ala Thr Gly Val Gly Gln His Gln Met Trp Ala Ala Gln Tyr Tyr
    370                 375                 380 act tac aag cgg cca cgg cag tgg ctg tct tcg tct ggt ttg ggg gca       1200
Thr Tyr Lys Arg Pro Arg Gln Trp Leu Ser Ser Ser Gly Leu Gly Ala
```

```
                     385                 390                 395                 400
atg gga ttt ggg tta cca gct gca gct ggc gct gct gtg gcc aac cca         1248
Met Gly Phe Gly Leu Pro Ala Ala Ala Gly Ala Ala Val Ala Asn Pro
                405                 410                 415 ggt gtt aca gtt gtt gac att gat ggt gat ggt agt ttc ctc atg aac         1296
Gly Val Thr Val Val Asp Ile Asp Gly Asp Gly Ser Phe Leu Met Asn
            420                 425                 430 att cag gag ttg gcg ttg atc cgc att gag aac ctc cca gtg aag gtg         1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat         1392
Met Ile Leu Asn Asn Gln His Leu Gly Met Val Val Gln Trp Glu Asp
    450                 455                 460 agg ttt tac aag gcc aat cgg gcg cac aca tac ctt ggc aac cca gaa         1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc         1488
Asn Glu Ser Glu Ile Tyr Pro Asp Phe Val Thr Ile Ala Lys Gly Phe
                485                 490                 495 aac gtt cca gca gtt cga gtg acg aag aag agc gaa gtc act gca gca         1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc ata         1584
Ile Lys Lys Met Leu Glu Thr Pro Gly Pro Tyr Leu Leu Asp Ile Ile
        515                 520                 525 gtc ccg cat cag gag cac gtg ctg cct atg atc cca agc ggt ggt gct         1632
Val Pro His Gln Glu His Val Leu Pro Met Ile Pro Ser Gly Gly Ala
    530                 535                 540 ttc aag gac atg atc atg gag ggt gat ggc agg acc tcg tac                 1674
Phe Lys Asp Met Ile Met Glu Gly Asp Gly Arg Thr Ser Tyr
545                 550                 555

<210> SEQ ID NO 16
<211> LENGTH: 557
<212> TYPE: PRT
<213> ORGANISM: Triticum aestivum

<400> SEQUENCE: 16

Val Asp Val Phe Ala Tyr Pro Gly Gly Ala Ser Met Glu Ile His Gln
 1               5                  10                  15

Ala Leu Thr Arg Ser Pro Val Ile Thr Asn His Leu Phe Arg His Glu
            20                  25                  30

Gln Gly Glu Ala Phe Ala Ala Ser Gly Tyr Ala Arg Ala Ser Gly Arg
        35                  40                  45

Val Gly Val Cys Val Ala Thr Ser Gly Pro Gly Ala Thr Asn Leu Val
    50                  55                  60

Ser Ala Leu Ala Asp Ala Leu Leu Asp Ser Ile Pro Met Val Ala Ile
65                  70                  75                  80

Thr Gly Gln Val Pro Arg Arg Met Ile Gly Thr Asp Ala Phe Gln Glu
                85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160
```

Leu Pro Gly Tyr Ile Ala Arg Leu Pro Lys Pro Pro Ser Thr Glu Ser
            165                 170                 175

Leu Glu Gln Val Leu Arg Leu Val Gly Glu Ser Arg Arg Pro Ile Leu
        180                 185                 190

Tyr Val Gly Gly Gly Cys Ala Ala Ser Gly Glu Glu Leu Arg Arg Phe
            195                 200                 205

Val Glu Leu Thr Gly Ile Pro Val Thr Thr Leu Met Gly Leu Gly
        210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Leu
            245                 250                 255

Ala Phe Gly Val Arg Phe Asp Asp Arg Val Thr Gly Lys Ile Glu Ala
            260                 265                 270

Phe Ala Ser Arg Ser Lys Ile Val His Ile Asp Ile Asp Pro Ala Glu
        275                 280                 285

Ile Gly Lys Asn Lys Gln Pro His Val Ser Ile Cys Ala Asp Val Lys
        290                 295                 300

Leu Ala Leu Gln Gly Leu Asn Asp Leu Leu Asn Gly Ser Lys Ala Gln
305                 310                 315                 320

Gln Gly Leu Asp Phe Gly Pro Trp His Lys Glu Leu Asp Gln Gln Lys
            325                 330                 335

Arg Glu Phe Pro Leu Gly Phe Lys Thr Phe Gly Glu Ala Ile Pro Pro
            340                 345                 350

Gln Tyr Ala Ile Gln Val Leu Asp Glu Leu Thr Lys Gly Glu Ala Ile
        355                 360                 365

Ile Ala Thr Gly Val Gly Gln His Gln Met Trp Ala Ala Gln Tyr Tyr
        370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Gly Ala Ala Val Ala Asn Pro
            405                 410                 415

Gly Val Thr Val Val Asp Ile Asp Gly Asp Gly Ser Phe Leu Met Asn
        420                 425                 430

Ile Gln Glu Leu Ala Leu Ile Arg Ile Glu Asn Leu Pro Val Lys Val
        435                 440                 445

Met Ile Leu Asn Asn Gln His Leu Gly Met Val Val Gln Trp Glu Asp
450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
            485                 490                 495

Asn Val Pro Ala Val Arg Val Thr Lys Lys Ser Glu Val Thr Ala Ala
        500                 505                 510

Ile Lys Lys Met Leu Glu Thr Pro Gly Pro Tyr Leu Leu Asp Ile Ile
        515                 520                 525

Val Pro His Gln Glu His Val Leu Pro Met Ile Pro Ser Gly Gly Ala
        530                 535                 540

Phe Lys Asp Met Ile Met Glu Gly Asp Gly Arg Thr Ser
545                 550                 555

<210> SEQ ID NO 17
<211> LENGTH: 1674

```
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (718)..(719)
<223> OTHER INFORMATION: unknown nucleotide

<400> SEQUENCE: 17 gtc gac gtc ttc gcc tac ccc ggc ggc gcc tcc atg gag atc cac cag      48
Val Asp Val Phe Ala Tyr Pro Gly Gly Ala Ser Met Glu Ile His Gln
 1               5                  10                  15 gcg ctg acg cgc tcg ccc gtc atc acc aac cac ctc ttc cgc cac gag      96
Ala Leu Thr Arg Ser Pro Val Ile Thr Asn His Leu Phe Arg His Glu
             20                  25                  30 cag ggg gag gcg ttc gcg gcg tcc ggc tac gcc cgc gcg tcc ggc cgc     144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc     192
Val Gly Val Cys Val Ala Thr Ser Gly Pro Gly Ala Thr Asn Leu Val
     50                  55                  60 tcc gcg ctc gcc gac gcc ctc ctc gac tcc atc ccc atg gtc gcc atc     240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gac gcg ttc cag gag     288
Thr Gly Gln Val Pro Arg Arg Met Ile Gly Thr Asp Ala Phe Gln Glu
                 85                  90                  95 acg ccc ata gtg gag gtc acg cgc tcc atc acc aag cac aac tac ctg     336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc     384
Val Leu Asp Val Glu Asp Ile Pro Arg Val Ile Gln Glu Ala Phe Phe
        115                 120                 125 ctt gca tcc tct ggc cgc ccg ggg ccg gtg cta gtt gat atc ccc aag     432
Leu Ala Ser Ser Gly Arg Pro Gly Pro Val Leu Val Asp Ile Pro Lys
    130                 135                 140 gac atc cag cag cag atg gct gtg ccc gtc tgg gac act cca atg agt     480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg     528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg     576
Leu Glu Gln Val Leu Arg Leu Val Gly Glu Ser Arg Arg Pro Ile Leu
            180                 185                 190 tat gtt ggt ggt ggc tgc gct gcg tct ggc gag gag ttg cgc cgc ttt     624
Tyr Val Gly Gly Gly Cys Ala Ala Ser Gly Glu Glu Leu Arg Arg Phe
        195                 200                 205 gtt gag ctt act ggg att cca gtt aca act act ctg atg ggc ctt ggc     672
Val Glu Leu Thr Gly Ile Pro Val Thr Thr Thr Leu Met Gly Leu Gly
    210                 215                 220 aac ttc ccc agc gac gac cca ctg tct ctg cgc atg ctt ggg atg nnt     720
Asn Phe Pro Ser Asp Asp Pro Leu Ser Leu Arg Met Leu Gly Met Asn
225                 230                 235                 240 ggc act gtg tat gca aat tat gca gta gat aag gct gac ctg ttg ctc     768
Gly Thr Val Tyr Ala Asn Tyr Ala Val Asp Lys Ala Asp Leu Leu Leu
                245                 250                 255 gca ttt ggt gtg cgg ttt gat gat cgt gtg act ggg aaa atc gag gct     816
Ala Phe Gly Val Arg Phe Asp Asp Arg Val Thr Gly Lys Ile Glu Ala
            260                 265                 270
```

```
ttt gca agc agg tcc aag att gtg cac att gac att gac cca gct gag      864
Phe Ala Ser Arg Ser Lys Ile Val His Ile Asp Ile Asp Pro Ala Glu
            275                 280                 285 att ggc aag aac aag cag cca cat gtc tcc att tgt gca gat gtt aag      912
Ile Gly Lys Asn Lys Gln Pro His Val Ser Ile Cys Ala Asp Val Lys
290                 295                 300 ctt gct tta cag ggg ttg aat gat cta tta aat ggg agc aaa gca caa      960
Leu Ala Leu Gln Gly Leu Asn Asp Leu Leu Asn Gly Ser Lys Ala Gln
305                 310                 315                 320 cag ggt ctg gat ttt ggt cca tgg cac aag gag ttg gat cag cag aag     1008
Gln Gly Leu Asp Phe Gly Pro Trp His Lys Glu Leu Asp Gln Gln Lys
                325                 330                 335 agg gag ttt cct cta gga ttc aag act ttt ggc gag gcc atc ccg ccg     1056
Arg Glu Phe Pro Leu Gly Phe Lys Thr Phe Gly Glu Ala Ile Pro Pro
            340                 345                 350 caa tat gct atc cag gta ctg gat gag ctg aca aaa ggg gag gcg atc     1104
Gln Tyr Ala Ile Gln Val Leu Asp Glu Leu Thr Lys Gly Glu Ala Ile
        355                 360                 365 att gcc act ggt gtt ggg cag cac cag atg tgg gcg gct cag tat tac     1152
Ile Ala Thr Gly Val Gly Gln His Gln Met Trp Ala Ala Gln Tyr Tyr
370                 375                 380 act tac aag cgg cca cgg cag tgg ctg tct tcg tct ggt ttg ggg gca     1200
Thr Tyr Lys Arg Pro Arg Gln Trp Leu Ser Ser Ser Gly Leu Gly Ala
385                 390                 395                 400 atg gga ttt ggg tta cca gct gca gct ggc gct gct gtg gcc aac cca     1248
Met Gly Phe Gly Leu Pro Ala Ala Ala Gly Ala Ala Val Ala Asn Pro
                405                 410                 415 ggt gtt aca gtt gtt gac att gat ggt gat ggt agt ttc ctc atg aac     1296
Gly Val Thr Val Val Asp Ile Asp Gly Asp Gly Ser Phe Leu Met Asn
            420                 425                 430 att cag gag ttg gcg ttg atc cgc att gag aac ctc cca gtg aag gtg     1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat     1392
Met Ile Leu Asn Asn Gln His Leu Gly Met Val Val Gln Trp Glu Asp
450                 455                 460 agg ttt tac aag gcc aat cgg gcg cac aca tac ctt ggc aac cca gaa     1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc     1488
Asn Glu Ser Glu Ile Tyr Pro Asp Phe Val Thr Ile Ala Lys Gly Phe
                485                 490                 495 aac gtt cca gca gtt cga gtg acg aag aag agc gaa gtc act gca gca     1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc ata     1584
Ile Lys Lys Met Leu Glu Thr Pro Gly Pro Tyr Leu Leu Asp Ile Ile
        515                 520                 525 gtc ccg cat cag gag cac gtg ctg cct atg atc cca aac ggt ggt gct     1632
Val Pro His Gln Glu His Val Leu Pro Met Ile Pro Asn Gly Gly Ala
530                 535                 540 ttc aag gac atg atc atg gag ggt gat ggc agg acc tcg tac             1674
Phe Lys Asp Met Ile Met Glu Gly Asp Gly Arg Thr Ser
545                 550                 555

<210> SEQ ID NO 18
<211> LENGTH: 557
<212> TYPE: PRT
<213> ORGANISM: Triticum aestivum
```

```
<400> SEQUENCE: 18

Val Asp Val Phe Ala Tyr Pro Gly Gly Ala Ser Met Glu Ile His Gln
  1               5                  10                  15

Ala Leu Thr Arg Ser Pro Val Ile Thr Asn His Leu Phe Arg His Glu
             20                  25                  30

Gln Gly Glu Ala Phe Ala Ala Ser Gly Tyr Ala Arg Ala Ser Gly Arg
         35                  40                  45

Val Gly Val Cys Val Ala Thr Ser Gly Pro Gly Ala Thr Asn Leu Val
     50                  55                  60

Ser Ala Leu Ala Asp Ala Leu Leu Asp Ser Ile Pro Met Val Ala Ile
 65                  70                  75                  80

Thr Gly Gln Val Pro Arg Arg Met Ile Gly Thr Asp Ala Phe Gln Glu
                 85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
            180                 185                 190

Tyr Val Gly Gly Gly Cys Ala Ala Ser Gly Glu Glu Leu Arg Arg Phe
        195                 200                 205

Val Glu Leu Thr Gly Ile Pro Val Thr Thr Thr Leu Met Gly Leu Gly
    210                 215                 220

Asn Phe Pro Ser Asp Asp Pro Leu Ser Leu Arg Met Leu Gly Met Asn
225                 230                 235                 240

Gly Thr Val Tyr Ala Asn Tyr Ala Val Asp Lys Ala Asp Leu Leu Leu
                245                 250                 255

Ala Phe Gly Val Arg Phe Asp Asp Arg Val Thr Gly Lys Ile Glu Ala
            260                 265                 270

Phe Ala Ser Arg Ser Lys Ile Val His Ile Asp Ile Asp Pro Ala Glu
        275                 280                 285

Ile Gly Lys Asn Lys Gln Pro His Val Ser Ile Cys Ala Asp Val Lys
    290                 295                 300

Leu Ala Leu Gln Gly Leu Asn Asp Leu Leu Asn Gly Ser Lys Ala Gln
305                 310                 315                 320

Gln Gly Leu Asp Phe Gly Pro Trp His Lys Glu Leu Asp Gln Gln Lys
                325                 330                 335

Arg Glu Phe Pro Leu Gly Phe Lys Thr Phe Gly Glu Ala Ile Pro Pro
            340                 345                 350

Gln Tyr Ala Ile Gln Val Leu Asp Glu Leu Thr Lys Gly Glu Ala Ile
        355                 360                 365

Ile Ala Thr Gly Val Gly Gln His Gln Met Trp Ala Ala Gln Tyr Tyr
    370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Gly Ala Ala Val Ala Asn Pro
                405                 410                 415
```

```
Gly Val Thr Val Val Asp Ile Asp Gly Asp Gly Ser Phe Leu Met Asn
            420                 425                 430

Ile Gln Glu Leu Ala Leu Ile Arg Ile Glu Asn Leu Pro Val Lys Val
            435                 440                 445

Met Ile Leu Asn Asn Gln His Leu Gly Met Val Val Gln Trp Glu Asp
450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
                500                 505                 510

Ile Lys Lys Met Leu Glu Thr Pro Gly Pro Tyr Leu Leu Asp Ile Ile
            515                 520                 525

Val Pro His Gln Glu His Val Leu Pro Met Ile Pro Asn Gly Gly Ala
            530                 535                 540

Phe Lys Asp Met Ile Met Glu Gly Asp Gly Arg Thr Ser
545                 550                 555

<210> SEQ ID NO 19
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (643)
<223> OTHER INFORMATION: unknown nucleotide
<220> FEATURE:
<221> NAME/KEY: modified_base
<222> LOCATION: (776)
<223> OTHER INFORMATION: unknown nucleotide
<220> FEATURE:
<221> NAME/KEY: modified_base
<222> LOCATION: (873)
<223> OTHER INFORMATION: unknown nucleotide
<220> FEATURE:
<221> NAME/KEY: modified_base
<222> LOCATION: (879)
<223> OTHER INFORMATION: unknown nucleotide

<400> SEQUENCE: 19 gtc gac gtc ttc gcc tac ccc ggc ggc gcc tcc atg gag atc cac cag      48
Val Asp Val Phe Ala Tyr Pro Gly Gly Ala Ser Met Glu Ile His Gln
  1               5                  10                  15 gcg ctg acg cgc tcg ccc gtc atc acc aac cac ctc ttc cgc cac gag      96
Ala Leu Thr Arg Ser Pro Val Ile Thr Asn His Leu Phe Arg His Glu
             20                  25                  30 cag ggg gag gcg ttc gcg gcg tcc ggc tac gcc cgc gcg tcc ggc cgc     144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc     192
Val Gly Val Cys Val Ala Thr Ser Gly Pro Gly Ala Thr Asn Leu Val
 50                  55                  60 tcc gcg ctc gcc gac gcc ctc ctc gac tcc atc ccc atg gtc gcc atc     240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gac gcg ttc cag gag     288
Thr Gly Gln Val Pro Arg Arg Met Ile Gly Thr Asp Ala Phe Gln Glu
             85                  90                  95
```

```
acg ccc ata gtg gag gtc acg cgc tcc atc acc aag cac aac tac ctg      336
Thr Pro Ile Val Glu Val Thr Arg Ser Ile Thr Lys His Asn Tyr Leu
        100                 105                 110 gtc ctt gac gtg gag gat atc ccc cgc gtc atc cag gaa gcc ttc ttc      384
Val Leu Asp Val Glu Asp Ile Pro Arg Val Ile Gln Glu Ala Phe Phe
        115                 120                 125 ctt gca tcc tct ggc cgc ccg ggg ccg gtg cta gtt gat atc ccc aag      432
Leu Ala Ser Ser Gly Arg Pro Gly Pro Val Leu Val Asp Ile Pro Lys
        130                 135                 140 gac atc cag cag cag atg gct gtg ccc gtc tgg gac act cca atg agt      480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg      528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg      576
Leu Glu Gln Val Leu Arg Leu Val Gly Glu Ser Arg Arg Pro Ile Leu
        180                 185                 190 tat gtt ggt ggt ggc tgc gct gcg tct ggc gag gag ttg cgc cgc ttt      624
Tyr Val Gly Gly Gly Cys Ala Ala Ser Gly Glu Glu Leu Arg Arg Phe
        195                 200                 205 gtt gag ctt act ggg att nca gtt aca act act ctg atg ggc ctt ggc      672
Val Glu Leu Thr Gly Ile Thr Val Thr Thr Thr Leu Met Gly Leu Gly
210                 215                 220 aac ttc ccc agc gac gac cca ctg tct ctg cgc atg ctt ggg atg cat      720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ctc      768
Gly Thr Val Tyr Ala Asn Tyr Ala Val Asp Lys Ala Asp Leu Leu Leu
                245                 250                 255 gca ttt gnt gtg cgg ttt gat gat cgt gtg act ggg aaa atc gag gct      816
Ala Phe Asp Val Arg Phe Asp Asp Arg Val Thr Gly Lys Ile Glu Ala
        260                 265                 270 ttt gca agc agg tcc aag att gtg cac att gac att gac cca gct gag      864
Phe Ala Ser Arg Ser Lys Ile Val His Ile Asp Ile Asp Pro Ala Glu
        275                 280                 285 att ggc aan aac aan cag cca cat gtc tcc att tgt gca gat gtt aag      912
Ile Gly Lys Asn Lys Gln Pro His Val Ser Ile Cys Ala Asp Val Lys
290                 295                 300 ctt gct tta cag ggg ttg aat gat cta tta aat ggg agc aaa gca caa      960
Leu Ala Leu Gln Gly Leu Asn Asp Leu Leu Asn Gly Ser Lys Ala Gln
305                 310                 315                 320 cag ggt ctg gat ttt ggt cca tgg cac aag gag ttg gat cag cag aag     1008
Gln Gly Leu Asp Phe Gly Pro Trp His Lys Glu Leu Asp Gln Gln Lys
                325                 330                 335 agg gag ttt cct cta gga ttc aag act ttt ggc gag gcc atc ccg ccg     1056
Arg Glu Phe Pro Leu Gly Phe Lys Thr Phe Gly Glu Ala Ile Pro Pro
        340                 345                 350 caa tat gct atc cag gta ctg gat gag ctg aca aaa ggg gag gcg atc     1104
Gln Tyr Ala Ile Gln Val Leu Asp Glu Leu Thr Lys Gly Glu Ala Ile
        355                 360                 365 att gcc act ggt gtt ggg cag cac cag atg tgg gcg gct cag tat tac     1152
Ile Ala Thr Gly Val Gly Gln His Gln Met Trp Ala Ala Gln Tyr Tyr
370                 375                 380 act tac aag cgg cca cgg cag tgg ctg tct tcg tct ggt ttg ggg gca     1200
Thr Tyr Lys Arg Pro Arg Gln Trp Leu Ser Ser Ser Gly Leu Gly Ala
385                 390                 395                 400 atg gga ttt ggg tta cca gct gca gct ggc gct gct gtg gcc aac cca     1248
Met Gly Phe Gly Leu Pro Ala Ala Ala Gly Ala Ala Val Ala Asn Pro
                405                 410                 415
```

```
ggt gtt aca gtt gtt gac att gat ggt gat ggt agt ttc ctc atg aac      1296
Gly Val Thr Val Val Asp Ile Asp Gly Asp Gly Ser Phe Leu Met Asn
            420                 425                 430 att cag gag ttg gcg ttg atc cgc att gag aac ctc cca gtg aag gtg      1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat      1392
Met Ile Leu Asn Asn Gln His Leu Gly Met Val Val Gln Trp Glu Asp
450                 455                 460 agg ttt tac aag gcc aat cgg gcg cac aca tac ctt ggc aac cca gaa      1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc      1488
Asn Glu Ser Glu Ile Tyr Pro Asp Phe Val Thr Ile Ala Lys Gly Phe
                485                 490                 495 aac gtt cca gca gtt cga gtg acg aag aag agc gaa gtc act gca gca      1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc ata      1584
Ile Lys Lys Met Leu Glu Thr Pro Gly Pro Tyr Leu Leu Asp Ile Ile
        515                 520                 525 gtc ccg cat cag gag cac gtg ctg cct atg atc cca aac ggt ggt gct      1632
Val Pro His Gln Glu His Val Leu Pro Met Ile Pro Asn Gly Gly Ala
530                 535                 540 ttc aag gac atg atc atg gag ggt gat ggc agg acc tcg tac              1674
Phe Lys Asp Met Ile Met Glu Gly Asp Gly Arg Thr Ser Tyr
545                 550                 555

<210> SEQ ID NO 20
<211> LENGTH: 557
<212> TYPE: PRT
<213> ORGANISM: Triticum aestivum

<400> SEQUENCE: 20

Val Asp Val Phe Ala Tyr Pro Gly Gly Ala Ser Met Glu Ile His Gln
1               5                   10                  15

Ala Leu Thr Arg Ser Pro Val Ile Thr Asn His Leu Phe Arg His Glu
            20                  25                  30

Gln Gly Glu Ala Phe Ala Ala Ser Gly Tyr Ala Arg Ala Ser Gly Arg
        35                  40                  45

Val Gly Val Cys Val Ala Thr Ser Gly Pro Gly Ala Thr Asn Leu Val
    50                  55                  60

Ser Ala Leu Ala Asp Ala Leu Leu Asp Ser Ile Pro Met Val Ala Ile
65                  70                  75                  80

Thr Gly Gln Val Pro Arg Arg Met Ile Gly Thr Asp Ala Phe Gln Glu
                85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
```

180                 185                 190
Tyr Val Gly Gly Gly Cys Ala Ala Ser Gly Glu Glu Leu Arg Arg Phe
            195                 200                 205

Val Glu Leu Thr Gly Ile Thr Val Thr Thr Thr Leu Met Gly Leu Gly
    210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Leu
                245                 250                 255

Ala Phe Asp Val Arg Phe Asp Arg Val Thr Gly Lys Ile Glu Ala
            260                 265                 270

Phe Ala Ser Arg Ser Lys Ile Val His Ile Asp Ile Asp Pro Ala Glu
            275                 280                 285

Ile Gly Lys Asn Lys Gln Pro His Val Ser Ile Cys Ala Asp Val Lys
            290                 295                 300

Leu Ala Leu Gln Gly Leu Asn Asp Leu Leu Asn Gly Ser Lys Ala Gln
305                 310                 315                 320

Gln Gly Leu Asp Phe Gly Pro Trp His Lys Glu Leu Asp Gln Gln Lys
                325                 330                 335

Arg Glu Phe Pro Leu Gly Phe Lys Thr Phe Gly Glu Ala Ile Pro Pro
            340                 345                 350

Gln Tyr Ala Ile Gln Val Leu Asp Glu Leu Thr Lys Gly Glu Ala Ile
            355                 360                 365

Ile Ala Thr Gly Val Gly Gln His Gln Met Trp Ala Ala Gln Tyr Tyr
            370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Ala Gly Ala Ala Val Ala Asn Pro
                405                 410                 415

Gly Val Thr Val Val Asp Ile Asp Gly Asp Gly Ser Phe Leu Met Asn
            420                 425                 430

Ile Gln Glu Leu Ala Leu Ile Arg Ile Glu Asn Leu Pro Val Lys Val
            435                 440                 445

Met Ile Leu Asn Asn Gln His Leu Gly Met Val Val Gln Trp Glu Asp
            450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
            500                 505                 510

Ile Lys Lys Met Leu Glu Thr Pro Gly Pro Tyr Leu Leu Asp Ile Ile
            515                 520                 525

Val Pro His Gln Glu His Val Leu Pro Met Ile Pro Asn Gly Gly Ala
            530                 535                 540

Phe Lys Asp Met Ile Met Glu Gly Asp Gly Arg Thr Ser
545                 550                 555

<210> SEQ ID NO 21
<211> LENGTH: 1674
<212> TYPE: DNA
<213> ORGANISM: Triticum aestivum
<220> FEATURE:
<221> NAME/KEY: CDS
<222> LOCATION: (1)..(1671)

<220> FEATURE:
<221> NAME/KEY: modified_base
<222> LOCATION: (766)
<223> OTHER INFORMATION: unknown nucleotide
<220> FEATURE:
<221> NAME/KEY: modified_base
<222> LOCATION: (769)
<223> OTHER INFORMATION: unknown nucleotide

<400> SEQUENCE: 21

```
gtc gac gtc ttc gcc tac ccc ggc ggc gcc tcc atg gag atc cac cag      48
Val Asp Val Phe Ala Tyr Pro Gly Gly Ala Ser Met Glu Ile His Gln
 1               5                  10                  15 gcg ctg acg cgc tcg ccc gtc atc acc aac cac ctc ttc cgc cac gag      96
Ala Leu Thr Arg Ser Pro Val Ile Thr Asn His Leu Phe Arg His Glu
             20                  25                  30 cag ggg gag gcg ttc gcg gcg tcc ggc tac gcc cgc gcg tcc ggc cgc     144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc     192
Val Gly Val Cys Val Ala Thr Ser Gly Pro Gly Ala Thr Asn Leu Val
 50                  55                  60 tcc gcg ctc gcc gac gcc ctc ctc gac tcc atc ccc atg gtc gcc atc     240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gac gcg ttc cag gag     288
Thr Gly Gln Val Pro Arg Arg Met Ile Gly Thr Asp Ala Phe Gln Glu
                 85                  90                  95 acg ccc ata gtg gag gtc acg cgc tcc atc acc aag cac aac tac ctg     336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc     384
Val Leu Asp Val Glu Asp Ile Pro Arg Val Ile Gln Glu Ala Phe Phe
        115                 120                 125 ctt gca tcc tct ggc cgc ccg ggg ccg gtg cta gtt gat atc ccc aag     432
Leu Ala Ser Ser Gly Arg Pro Gly Pro Val Leu Val Asp Ile Pro Lys
    130                 135                 140 gac atc cag cag cag atg gct gtg ccc gtc tgg gac act cca atg agt     480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg     528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg     576
Leu Glu Gln Val Leu Arg Leu Val Gly Glu Ser Arg Arg Pro Ile Leu
            180                 185                 190 tat gtt ggt ggt ggc tgc gct gcg tct ggc gag gag ttg cgc cgc ttt     624
Tyr Val Gly Gly Gly Cys Ala Ala Ser Gly Glu Glu Leu Arg Arg Phe
        195                 200                 205 gtt gag ctt act ggg att cca gtt aca act act ctg atg ggc ctt ggc     672
Val Glu Leu Thr Gly Ile Pro Val Thr Thr Thr Leu Met Gly Leu Gly
    210                 215                 220 aac ttc ccc agc gac gac cca ctg tct ctg cgc atg ctt ggg atg cat     720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ntc     768
Gly Thr Val Tyr Ala Asn Tyr Ala Val Asp Lys Ala Asp Leu Leu Ile
                245                 250                 255 nca ttt ggt gtg cgg ttt gat gat cgt gtg act ggg aaa atc gag gct     816
Thr Phe Gly Val Arg Phe Asp Asp Arg Val Thr Gly Lys Ile Glu Ala
            260                 265                 270
```

| | |
|---|---|
| ttt gca agc agg tcc aag att gtg cac att gac att gac cca gct gag<br>Phe Ala Ser Arg Ser Lys Ile Val His Ile Asp Ile Asp Pro Ala Glu<br>275                          280                        285 | 864 |
| att ggc aag aac aag cag cca cat gtc tcc att tgt gcc gat gtt aag<br>Ile Gly Lys Asn Lys Gln Pro His Val Ser Ile Cys Ala Asp Val Lys<br>290                          295                        300 | 912 |
| ctt gct tta cag ggg ttg aat gat cta tta aat ggg agc aaa gca caa<br>Leu Ala Leu Gln Gly Leu Asn Asp Leu Leu Asn Gly Ser Lys Ala Gln<br>305                          310                        315                        320 | 960 |
| cag ggt ctg gat ttt ggt cca tgg cac aag gag ttg gat cag cag aag<br>Gln Gly Leu Asp Phe Gly Pro Trp His Lys Glu Leu Asp Gln Gln Lys<br>                        325                        330                        335 | 1008 |
| agg gag ttt cct cta gga ttc aag act ttt ggc gag gcc atc ccg ccg<br>Arg Glu Phe Pro Leu Gly Phe Lys Thr Phe Gly Glu Ala Ile Pro Pro<br>                        340                        345                        350 | 1056 |
| caa tat gct atc cag gta ctg gat gag ctg aca aaa ggg gag gcg atc<br>Gln Tyr Ala Ile Gln Val Leu Asp Glu Leu Thr Lys Gly Glu Ala Ile<br>                        355                        360                        365 | 1104 |
| att gcc act ggt gtt ggg cag cac cag atg tgg gcg gct cag tat tac<br>Ile Ala Thr Gly Val Gly Gln His Gln Met Trp Ala Ala Gln Tyr Tyr<br>370                          375                        380 | 1152 |
| act tac aag cgg cca cgg cag tgg ctg tct tcg tct ggt ttg ggg gca<br>Thr Tyr Lys Arg Pro Arg Gln Trp Leu Ser Ser Ser Gly Leu Gly Ala<br>385                          390                        395                        400 | 1200 |
| atg gga ttt ggg tta cca gct gca gct ggc gct gct gtg gcc aac cca<br>Met Gly Phe Gly Leu Pro Ala Ala Ala Gly Ala Ala Val Ala Asn Pro<br>                        405                        410                        415 | 1248 |
| ggt gtt aca gtt gtt gac att gat ggt gat ggt agt ttc ctc atg aac<br>Gly Val Thr Val Val Asp Ile Asp Gly Asp Gly Ser Phe Leu Met Asn<br>                        420                        425                        430 | 1296 |
| att cag gag ttg gcg ttg atc cgc att gag aac ctc cca gtg aag gtg<br>Ile Gln Glu Leu Ala Leu Ile Arg Ile Glu Asn Leu Pro Val Lys Val<br>                        435                        440                        445 | 1344 |
| atg ata ttg aac aac cag cat ctg gga atg gtg gtg cag tgg gag gat<br>Met Ile Leu Asn Asn Gln His Leu Gly Met Val Val Gln Trp Glu Asp<br>450                          455                        460 | 1392 |
| agg ttt tac aag gcc aat cgg gcg cac aca tac ctt ggc aac cca gaa<br>Arg Phe Tyr Lys Ala Asn Arg Ala His Thr Tyr Leu Gly Asn Pro Glu<br>465                          470                        475                        480 | 1440 |
| aat gag agt gag ata tat cca gat ttt gtg acg att gct aaa gga ttc<br>Asn Glu Ser Glu Ile Tyr Pro Asp Phe Val Thr Ile Ala Lys Gly Phe<br>                        485                        490                        495 | 1488 |
| aac gtt cca gca gtt cga gtg acg aag aag agc gaa gtc act gca gca<br>Asn Val Pro Ala Val Arg Val Thr Lys Lys Ser Glu Val Thr Ala Ala<br>                        500                        505                        510 | 1536 |
| atc aag aag atg ctt gag acc cca ggg cca tac ttg ttg gat atc ata<br>Ile Lys Lys Met Leu Glu Thr Pro Gly Pro Tyr Leu Leu Asp Ile Ile<br>                        515                        520                        525 | 1584 |
| gtc ccg cat cag gag cac gtg ctg cct atg atc cca agc ggt ggt gct<br>Val Pro His Gln Glu His Val Leu Pro Met Ile Pro Ser Gly Gly Ala<br>530                          535                        540 | 1632 |
| ttc aag gac atg atc atg gag ggt gat ggc agg acc tcg tac<br>Phe Lys Asp Met Ile Met Glu Gly Asp Gly Arg Thr Ser<br>545                          550                        555 | 1674 |

<210> SEQ ID NO 22
<211> LENGTH: 557
<212> TYPE: PRT
<213> ORGANISM: Triticum aestivum

<400> SEQUENCE: 22

```
Val Asp Val Phe Ala Tyr Pro Gly Gly Ala Ser Met Glu Ile His Gln
 1               5                  10                  15

Ala Leu Thr Arg Ser Pro Val Ile Thr Asn His Leu Phe Arg His Glu
             20                  25                  30

Gln Gly Glu Ala Phe Ala Ala Ser Gly Tyr Ala Arg Ala Ser Gly Arg
         35                  40                  45

Val Gly Val Cys Val Ala Thr Ser Gly Pro Gly Ala Thr Asn Leu Val
     50                  55                  60

Ser Ala Leu Ala Asp Ala Leu Leu Asp Ser Ile Pro Met Val Ala Ile
 65              70                  75                  80

Thr Gly Gln Val Pro Arg Arg Met Ile Gly Thr Asp Ala Phe Gln Glu
                 85                  90                  95

Thr Pro Ile Val Glu Val Thr Arg Ser Ile Thr Lys His Asn Tyr Leu
             100                 105                 110

Val Leu Asp Val Glu Asp Ile Pro Arg Val Ile Gln Glu Ala Phe Phe
         115                 120                 125

Leu Ala Ser Ser Gly Arg Pro Gly Pro Val Leu Val Asp Ile Pro Lys
     130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                 165                 170                 175

Leu Glu Gln Val Leu Arg Leu Val Gly Glu Ser Arg Arg Pro Ile Leu
             180                 185                 190

Tyr Val Gly Gly Gly Cys Ala Ala Ser Gly Glu Glu Leu Arg Arg Phe
         195                 200                 205

Val Glu Leu Thr Gly Ile Pro Val Thr Thr Thr Leu Met Gly Leu Gly
     210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Ile
                 245                 250                 255

Thr Phe Gly Val Arg Phe Asp Asp Arg Val Thr Gly Lys Ile Glu Ala
             260                 265                 270

Phe Ala Ser Arg Ser Lys Ile Val His Ile Asp Ile Asp Pro Ala Glu
         275                 280                 285

Ile Gly Lys Asn Lys Gln Pro His Val Ser Ile Cys Ala Asp Val Lys
     290                 295                 300

Leu Ala Leu Gln Gly Leu Asn Asp Leu Leu Asn Gly Ser Lys Ala Gln
305                 310                 315                 320

Gln Gly Leu Asp Phe Gly Pro Trp His Lys Glu Leu Asp Gln Gln Lys
                 325                 330                 335

Arg Glu Phe Pro Leu Gly Phe Lys Thr Phe Gly Glu Ala Ile Pro Pro
             340                 345                 350

Gln Tyr Ala Ile Gln Val Leu Asp Glu Leu Thr Lys Gly Glu Ala Ile
         355                 360                 365

Ile Ala Thr Gly Val Gly Gln His Gln Met Trp Ala Ala Gln Tyr Tyr
     370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Gly Ala Ala Val Ala Asn Pro
                 405                 410                 415
```

```
Gly Val Thr Val Val Asp Ile Asp Gly Asp Gly Ser Phe Leu Met Asn
            420                 425                 430

Ile Gln Glu Leu Ala Leu Ile Arg Ile Glu Asn Leu Pro Val Lys Val
            435                 440                 445

Met Ile Leu Asn Asn Gln His Leu Gly Met Val Val Gln Trp Glu Asp
450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
            500                 505                 510

Ile Lys Lys Met Leu Glu Thr Pro Gly Pro Tyr Leu Leu Asp Ile Ile
            515                 520                 525

Val Pro His Gln Glu His Val Leu Pro Met Ile Pro Ser Gly Gly Ala
            530                 535                 540

Phe Lys Asp Met Ile Met Glu Gly Asp Gly Arg Thr Ser
545                 550                 555
```

<210> SEQ ID NO 23
<211> LENGTH: 1677
<212> TYPE: DNA
<213> ORGANISM: Triticum aestivum
<220> FEATURE:
<221> NAME/KEY: CDS
<222> LOCATION: (1)..(1674)
<220> FEATURE:
<221> NAME/KEY: modified_base
<222> LOCATION: (766)
<223> OTHER INFORMATION: unknown nucleotide
<220> FEATURE:
<221> NAME/KEY: modified_base
<222> LOCATION: (839)
<223> OTHER INFORMATION: unknown nucleotide
<220> FEATURE:
<221> NAME/KEY: modified_base
<222> LOCATION: (912)
<223> OTHER INFORMATION: unknown nucleotide
<220> FEATURE:
<221> NAME/KEY: modified_base
<222> LOCATION: (1008)
<223> OTHER INFORMATION: unknown nucleotide

<400> SEQUENCE: 23

```
gtc gac gtc ttc gcc tac ccc ggc ggc gcc tcc atg gag atc cac cag    48
Val Asp Val Phe Ala Tyr Pro Gly Gly Ala Ser Met Glu Ile His Gln
 1               5                  10                  15 gcg ctg acg cgc tcg ccc gtc atc acc aac cac ctc ttc cgc cac gag    96
Ala Leu Thr Arg Ser Pro Val Ile Thr Asn His Leu Phe Arg His Glu
                20                  25                  30 cag ggg gag gcg ttc gcg gcg tcc ggc tac gcc cgc gcg tcc ggc cgc   144
Gln Gly Glu Ala Phe Ala Ala Ser Gly Tyr Ala Arg Ala Ser Gly Arg
            35                  40                  45 gtc ggc gtc tgc gtc gcc acc tcc ggc ccg ggg gcc acc aac ctc gtc   192
Val Gly Val Cys Val Ala Thr Ser Gly Pro Gly Ala Thr Asn Leu Val
        50                  55                  60 tcc gcg ctc gcc gac gcc ctc ctc gac tcc atc ccc atg gtc gcc atc   240
Ser Ala Leu Ala Asp Ala Leu Leu Asp Ser Ile Pro Met Val Ala Ile
 65                  70                  75                  80 acg ggc cag gtc ccc cgc cgc atg atc ggc acg gac gcg ttc cag gag   288
Thr Gly Gln Val Pro Arg Arg Met Ile Gly Thr Asp Ala Phe Gln Glu
                85                  90                  95 acg ccc ata gtg gag gtc acg cgc tcc atc acc aag cac aac tac ctg   336
```

```
                Thr Pro Ile Val Glu Val Thr Arg Ser Ile Thr Lys His Asn Tyr Leu
                            100                 105                 110 gtc ctt gac gtg gag gat atc ccc cgc gtc atc cag gaa gcc ttc ttc         384
Val Leu Asp Val Glu Asp Ile Pro Arg Val Ile Gln Glu Ala Phe Phe
            115                 120                 125 ctt gca tcc tct ggc cgc ccg ggg ccg gtg cta gtt gat atc ccc aag         432
Leu Ala Ser Ser Gly Arg Pro Gly Pro Val Leu Val Asp Ile Pro Lys
        130                 135                 140 gac atc cag cag cag atg gct gtg ccc gtc tgg gac act cca atg agt         480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg         528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg         576
Leu Glu Gln Val Leu Arg Leu Val Gly Glu Ser Arg Arg Pro Ile Leu
            180                 185                 190 tat gtt ggt ggt ggc tgc gct gcg tct ggc gag gag ttg cgc cgc ttt         624
Tyr Val Gly Gly Gly Cys Ala Ala Ser Gly Glu Glu Leu Arg Arg Phe
        195                 200                 205 gtt gag ctt act ggg att cca gtt aca act act ctg atg ggc ctt ggc         672
Val Glu Leu Thr Gly Ile Pro Val Thr Thr Thr Leu Met Gly Leu Gly
210                 215                 220 aac ttc ccc agc gac gac cca ctg tct ctg cgc atg ctt ggg atg cat         720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ntc         768
Gly Thr Val Tyr Ala Asn Tyr Ala Val Asp Lys Ala Asp Leu Leu Ile
                245                 250                 255 gca ttt ggt gtg cgg ttt gat gat cgt gtg act ggg aaa atc gag gct         816
Ala Phe Gly Val Arg Phe Asp Asp Arg Val Thr Gly Lys Ile Glu Ala
            260                 265                 270 ttt gca agc agg tcc aag att gng cac att gac att gac cca gct gag         864
Phe Ala Ser Arg Ser Lys Ile Glu His Ile Asp Ile Asp Pro Ala Glu
        275                 280                 285 att ggc aag aac aag cag cca cat gtc tcc att tgt gca gat gtt aan         912
Ile Gly Lys Asn Lys Gln Pro His Val Ser Ile Cys Ala Asp Val Lys
290                 295                 300 ctt gct tta cag ggg ttg aat gat cta tta aat ggg agc aaa gca caa         960
Leu Ala Leu Gln Gly Leu Asn Asp Leu Leu Asn Gly Ser Lys Ala Gln
305                 310                 315                 320 cag ggt ctg gat ttt ggt cca tgg cac aag gag ttg gat cag can aan        1008
Gln Gly Leu Asp Phe Gly Pro Trp His Lys Glu Leu Asp Gln Thr Lys
                325                 330                 335 agg gag ttt cct cta gga ttc aag act ttt ggc gag gcc atc ccg ccg        1056
Arg Glu Phe Pro Leu Gly Phe Lys Thr Phe Gly Glu Ala Ile Pro Pro
            340                 345                 350 caa tat gct atc cag gta ctg gat gag ctg aca aaa ggg gag gcg atc        1104
Gln Tyr Ala Ile Gln Val Leu Asp Glu Leu Thr Lys Gly Glu Ala Ile
        355                 360                 365 att gcc act ggt gtt ggg cag cac cag atg tgg gcg gct cag tat tac        1152
Ile Ala Thr Gly Val Gly Gln His Gln Met Trp Ala Ala Gln Tyr Tyr
370                 375                 380 act tac aag cgg cca cgg cag tgg ctg tct tcg tct ggt ttg ggg gca        1200
Thr Tyr Lys Arg Pro Arg Gln Trp Leu Ser Ser Ser Gly Leu Gly Ala
385                 390                 395                 400 atg gga ttt ggg tta cca gct gca gct ggc gct gct gtg gca aac cca        1248
Met Gly Phe Gly Leu Pro Ala Ala Ala Gly Ala Ala Val Ala Asn Pro
                405                 410                 415
```

-continued

```
ggt gtt aca gtt gtt gac att gat ggt gat ggt agt ttc ctc atg aac    1296
Gly Val Thr Val Val Asp Ile Asp Gly Asp Gly Ser Phe Leu Met Asn
            420                 425                 430 att cag gag ttg gcg ttg atc cgc att gag aac ctc cca gtg aag gtg    1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat    1392
Met Ile Leu Asn Asn Gln His Leu Gly Met Val Val Gln Trp Glu Asp
    450                 455                 460 agg ttt tac aag gcc aat cgg gcg cac aca tac ctt ggc aac cca gaa    1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc    1488
Asn Glu Ser Glu Ile Tyr Pro Asp Phe Val Thr Ile Ala Lys Gly Phe
                485                 490                 495 aac gtt cca gca gtt cga gtg acg aag aag agc gaa gtc act gca gca    1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc ata    1584
Ile Lys Lys Met Leu Glu Thr Pro Gly Pro Tyr Leu Leu Asp Ile Ile
        515                 520                 525 gtc ccg cat cag gag cac gtg ctg cct atg atc cca aac ggt ggt gct    1632
Val Pro His Gln Glu His Val Leu Pro Met Ile Pro Asn Gly Gly Ala
    530                 535                 540 ttc aag gac atg atc atg gag ggt gat ggc agg acc tcg tac tga        1677
Phe Lys Asp Met Ile Met Glu Gly Asp Gly Arg Thr Ser Tyr
545                 550                 555
```

<210> SEQ ID NO 24
<211> LENGTH: 558
<212> TYPE: PRT
<213> ORGANISM: Triticum aestivum

<400> SEQUENCE: 24

```
Val Asp Val Phe Ala Tyr Pro Gly Gly Ala Ser Met Glu Ile His Gln
  1               5                  10                  15

Ala Leu Thr Arg Ser Pro Val Ile Thr Asn His Leu Phe Arg His Glu
                 20                  25                  30

Gln Gly Glu Ala Phe Ala Ala Ser Gly Tyr Ala Arg Ala Ser Gly Arg
             35                  40                  45

Val Gly Val Cys Val Ala Thr Ser Gly Pro Gly Ala Thr Asn Leu Val
         50                  55                  60

Ser Ala Leu Ala Asp Ala Leu Leu Asp Ser Ile Pro Met Val Ala Ile
 65                  70                  75                  80

Thr Gly Gln Val Pro Arg Arg Met Ile Gly Thr Asp Ala Phe Gln Glu
                 85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
            180                 185                 190
```

Tyr Val Gly Gly Gly Cys Ala Ala Ser Gly Glu Glu Leu Arg Arg Phe
            195                 200                 205

Val Glu Leu Thr Gly Ile Pro Val Thr Thr Thr Leu Met Gly Leu Gly
        210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Ile
            245                 250                 255

Ala Phe Gly Val Arg Phe Asp Asp Arg Val Thr Gly Lys Ile Glu Ala
        260                 265                 270

Phe Ala Ser Arg Ser Lys Ile Glu His Ile Asp Ile Asp Pro Ala Glu
        275                 280                 285

Ile Gly Lys Asn Lys Gln Pro His Val Ser Ile Cys Ala Asp Val Lys
        290                 295                 300

Leu Ala Leu Gln Gly Leu Asn Asp Leu Leu Asn Gly Ser Lys Ala Gln
305                 310                 315                 320

Gln Gly Leu Asp Phe Gly Pro Trp His Lys Glu Leu Asp Gln Thr Lys
            325                 330                 335

Arg Glu Phe Pro Leu Gly Phe Lys Thr Phe Gly Glu Ala Ile Pro Pro
        340                 345                 350

Gln Tyr Ala Ile Gln Val Leu Asp Glu Leu Thr Lys Gly Glu Ala Ile
        355                 360                 365

Ile Ala Thr Gly Val Gly Gln His Gln Met Trp Ala Ala Gln Tyr Tyr
        370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Ala Gly Ala Ala Val Ala Asn Pro
            405                 410                 415

Gly Val Thr Val Val Asp Ile Asp Gly Asp Gly Ser Phe Leu Met Asn
        420                 425                 430

Ile Gln Glu Leu Ala Leu Ile Arg Ile Glu Asn Leu Pro Val Lys Val
        435                 440                 445

Met Ile Leu Asn Asn Gln His Leu Gly Met Val Val Gln Trp Glu Asp
        450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
            485                 490                 495

Asn Val Pro Ala Val Arg Val Thr Lys Lys Ser Glu Val Thr Ala Ala
        500                 505                 510

Ile Lys Lys Met Leu Glu Thr Pro Gly Pro Tyr Leu Leu Asp Ile Ile
        515                 520                 525

Val Pro His Gln Glu His Val Leu Pro Met Ile Pro Asn Gly Gly Ala
        530                 535                 540

Phe Lys Asp Met Ile Met Glu Gly Asp Gly Arg Thr Ser Tyr
545                 550                 555

<210> SEQ ID NO 25
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:

```
<221> NAME/KEY: modified_base
<222> LOCATION: (681)
<223> OTHER INFORMATION: unknown nucleotide
<220> FEATURE:
<221> NAME/KEY: modified_base
<222> LOCATION: (766)
<223> OTHER INFORMATION: unknown nucleotide

<400> SEQUENCE: 25
```

| | | | | | | | | | | | | | | | | |
|---|---|---|---|---|---|---|---|---|---|---|---|---|---|---|---|---|
| gtc | gac | gtc | ttc | gcc | tac | cct | ggc | ggc | gcg | tcc | atg | gag | atc | cac | cag | 48 |
| Val | Asp | Val | Phe | Ala | Tyr | Pro | Gly | Gly | Ala | Ser | Met | Glu | Ile | His | Gln | |
| 1 | | | | 5 | | | | | 10 | | | | | 15 | | |
| gcg | ctg | acg | cgc | tcg | cca | gtc | atc | acc | aac | cac | ctc | ttc | cgc | cac | gag | 96 |
| Ala | Leu | Thr | Arg | Ser | Pro | Val | Ile | Thr | Asn | His | Leu | Phe | Arg | His | Glu | |
| | | | 20 | | | | | 25 | | | | | 30 | | | |
| cag | ggg | gag | gcg | ttc | gcg | gcg | tcc | ggg | tac | gcc | cgc | gcg | tcc | ggc | cgc | 144 |
| Gln | Gly | Glu | Ala | Phe | Ala | Ala | Ser | Gly | Tyr | Ala | Arg | Ala | Ser | Gly | Arg | |
| | | 35 | | | | | 40 | | | | | 45 | | | | |
| gtc | ggc | gtc | tgc | gtc | gcc | acc | tcc | ggc | ccg | ggg | gcc | acc | aac | ctc | gtc | 192 |
| Val | Gly | Val | Cys | Val | Ala | Thr | Ser | Gly | Pro | Gly | Ala | Thr | Asn | Leu | Val | |
| | 50 | | | | | 55 | | | | | 60 | | | | | |
| tcc | gcg | ctc | gcc | gac | gct | ctc | ctc | gac | tcc | atc | ccc | atg | gtc | gcc | atc | 240 |
| Ser | Ala | Leu | Ala | Asp | Ala | Leu | Leu | Asp | Ser | Ile | Pro | Met | Val | Ala | Ile | |
| 65 | | | | | 70 | | | | | 75 | | | | | 80 | |
| acg | ggc | cag | gtc | ccc | cgc | cgc | atg | atc | ggc | acg | gat | gcg | ttc | cag | gag | 288 |
| Thr | Gly | Gln | Val | Pro | Arg | Arg | Met | Ile | Gly | Thr | Asp | Ala | Phe | Gln | Glu | |
| | | | | 85 | | | | | 90 | | | | | 95 | | |
| acg | ccc | atc | gtg | gag | gtc | acg | cgc | tcc | atc | acc | aag | cac | aac | tac | ctg | 336 |
| Thr | Pro | Ile | Val | Glu | Val | Thr | Arg | Ser | Ile | Thr | Lys | His | Asn | Tyr | Leu | |
| | | | 100 | | | | | 105 | | | | | 110 | | | |
| gtc | ctt | gac | gtg | gag | gat | atc | ccc | cgc | gtc | atc | cag | gaa | gcc | ttc | ttc | 384 |
| Val | Leu | Asp | Val | Glu | Asp | Ile | Pro | Arg | Val | Ile | Gln | Glu | Ala | Phe | Phe | |
| | | 115 | | | | | 120 | | | | | 125 | | | | |
| ctc | gca | tcc | tct | ggc | cgc | ccg | ggg | ccg | gtg | ctg | gtt | gat | atc | ccc | aag | 432 |
| Leu | Ala | Ser | Ser | Gly | Arg | Pro | Gly | Pro | Val | Leu | Val | Asp | Ile | Pro | Lys | |
| | 130 | | | | | 135 | | | | | 140 | | | | | |
| gac | atc | cag | cag | cag | atg | gct | gtg | cct | gtc | tgg | gac | acg | ccg | atg | agt | 480 |
| Asp | Ile | Gln | Gln | Gln | Met | Ala | Val | Pro | Val | Trp | Asp | Thr | Pro | Met | Ser | |
| 145 | | | | | 150 | | | | | 155 | | | | | 160 | |
| ttg | cca | ggg | tac | atc | gcc | cgc | ctg | ccc | aag | cca | cca | tct | act | gaa | tcg | 528 |
| Leu | Pro | Gly | Tyr | Ile | Ala | Arg | Leu | Pro | Lys | Pro | Pro | Ser | Thr | Glu | Ser | |
| | | | | 165 | | | | | 170 | | | | | 175 | | |
| ctt | gag | cag | gtc | ctg | cgt | ctg | gtt | ggc | gag | tca | cgg | cgc | cca | att | ctg | 576 |
| Leu | Glu | Gln | Val | Leu | Arg | Leu | Val | Gly | Glu | Ser | Arg | Arg | Pro | Ile | Leu | |
| | | | 180 | | | | | 185 | | | | | 190 | | | |
| tat | gtt | ggt | ggt | ggc | tgc | gct | gca | tct | ggt | gag | gag | ttg | cgc | cgc | ttt | 624 |
| Tyr | Val | Gly | Gly | Gly | Cys | Ala | Ala | Ser | Gly | Glu | Glu | Leu | Arg | Arg | Phe | |
| | | 195 | | | | | 200 | | | | | 205 | | | | |
| gtt | gag | ctc | act | ggg | att | cca | gtt | aca | act | act | ctt | atg | ggc | ctt | ggc | 672 |
| Val | Glu | Leu | Thr | Gly | Ile | Pro | Val | Thr | Thr | Thr | Leu | Met | Gly | Leu | Gly | |
| | 210 | | | | | 215 | | | | | 220 | | | | | |
| aac | ttc | ccn | agt | gac | gac | cca | ctg | tct | ctg | cgc | atg | ctg | ggg | atg | cat | 720 |
| Asn | Phe | Pro | Ser | Asp | Asp | Pro | Leu | Ser | Leu | Arg | Met | Leu | Gly | Met | His | |
| 225 | | | | | 230 | | | | | 235 | | | | | 240 | |
| ggc | act | gtg | tat | gca | aat | tat | gca | gta | gat | aag | gct | gac | ctg | ttg | ntt | 768 |
| Gly | Thr | Val | Tyr | Ala | Asn | Tyr | Ala | Val | Asp | Lys | Ala | Asp | Leu | Leu | Ile | |
| | | | | 245 | | | | | 250 | | | | | 255 | | |
| gca | ttt | ggt | gtg | cgg | ttt | gat | gat | cgt | gtg | acc | ggg | aaa | atc | gag | gct | 816 |
| Ala | Phe | Gly | Val | Arg | Phe | Asp | Asp | Arg | Val | Thr | Gly | Lys | Ile | Glu | Ala | |
| | | | 260 | | | | | 265 | | | | | 270 | | | |
| ttt | gca | agc | agg | tcc | aag | att | gtg | cac | att | gac | att | gac | cca | gct | gag | 864 |

|  |  |  |  |  |  |  |  |  |  |  |  |  |
|---|---|---|---|---|---|---|---|---|---|---|---|---|
| Phe | Ala | Ser | Arg | Ser | Lys | Ile | Val | His | Ile | Asp | Ile | Asp | Pro | Ala | Glu |
|  |  |  | 275 |  |  |  |  | 280 |  |  |  |  | 285 |  |  |

```
att ggc aag aac aag cag cca cat gtc tcc att tgt gca gat gtt aag      912
Ile Gly Lys Asn Lys Gln Pro His Val Ser Ile Cys Ala Asp Val Lys
    290                 295                 300 ctt gct tta cag ggg ttg aat gct cta tta aat ggg agc aaa gca caa      960
Leu Ala Leu Gln Gly Leu Asn Ala Leu Leu Asn Gly Ser Lys Ala Gln
305                 310                 315                 320 cag ggt ctg gat ttt ggt cca tgg cac aag gag ttg gat cag cag aag     1008
Gln Gly Leu Asp Phe Gly Pro Trp His Lys Glu Leu Asp Gln Gln Lys
                325                 330                 335 agg gag ttt cct cta gga ttc aag act ttt ggt gag gcc atc ccg ccg     1056
Arg Glu Phe Pro Leu Gly Phe Lys Thr Phe Gly Glu Ala Ile Pro Pro
            340                 345                 350 caa tat gct atc cag gta ctg gat gag ctg aca aaa ggg gag gcg atc     1104
Gln Tyr Ala Ile Gln Val Leu Asp Glu Leu Thr Lys Gly Glu Ala Ile
        355                 360                 365 att gcc acc ggt gtt ggg cag cat cag atg tgg gcg gct cag tat tac     1152
Ile Ala Thr Gly Val Gly Gln His Gln Met Trp Ala Ala Gln Tyr Tyr
    370                 375                 380 act tac aag cgg cca cgg cag tgg ctg tct tca tcc ggt ttg ggt gca     1200
Thr Tyr Lys Arg Pro Arg Gln Trp Leu Ser Ser Ser Gly Leu Gly Ala
385                 390                 395                 400 atg gga ttt ggg ttg cca gct gca gct ggc gct gct gtg gcc aac cca     1248
Met Gly Phe Gly Leu Pro Ala Ala Ala Gly Ala Ala Val Ala Asn Pro
                405                 410                 415 ggt gtt aca gtt gtt gac att gat ggg gat ggt agt ttc ctc atg aac     1296
Gly Val Thr Val Val Asp Ile Asp Gly Asp Gly Ser Phe Leu Met Asn
            420                 425                 430 att cag gag ttg gcg ttg atc cgt att gag aac ctc cca gtg aag gtg     1344
Ile Gln Glu Leu Ala Leu Ile Arg Ile Glu Asn Leu Pro Val Lys Val
        435                 440                 445 atg ata ttg aac aac cag cat ctg gga atg gtg gtg cag tgg gag gat     1392
Met Ile Leu Asn Asn Gln His Leu Gly Met Val Val Gln Trp Glu Asp
    450                 455                 460 agg ttt tac aag gcc aac cgg gcg cac aca tac ctt ggc aac cca gaa     1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc     1488
Asn Glu Ser Glu Ile Tyr Pro Asp Phe Val Thr Ile Ala Lys Gly Phe
                485                 490                 495 aac gtt ccg gca gtt cgt gtg acg aag aag agc gaa gtc act gca gca     1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc att     1584
Ile Lys Lys Met Leu Glu Thr Pro Gly Pro Tyr Leu Leu Asp Ile Ile
        515                 520                 525 gtc ccg cat cag gag cac gtg ctg cct atg atc cca agc ggt ggt gct     1632
Val Pro His Gln Glu His Val Leu Pro Met Ile Pro Ser Gly Gly Ala
    530                 535                 540 ttt aag gac atg atc atg gag ggt gat ggc agg acc tcg tac              1674
Phe Lys Asp Met Ile Met Glu Gly Asp Gly Arg Thr Ser
545                 550                 555
```

<210> SEQ ID NO 26
<211> LENGTH: 557
<212> TYPE: PRT
<213> ORGANISM: Triticum aestivum

<400> SEQUENCE: 26

-continued

```
Val Asp Val Phe Ala Tyr Pro Gly Gly Ala Ser Met Glu Ile His Gln
 1               5                  10                  15

Ala Leu Thr Arg Ser Pro Val Ile Thr Asn His Leu Phe Arg His Glu
             20                  25                  30

Gln Gly Glu Ala Phe Ala Ala Ser Gly Tyr Ala Arg Ala Ser Gly Arg
         35                  40                  45

Val Gly Val Cys Val Ala Thr Ser Gly Pro Gly Ala Thr Asn Leu Val
     50                  55                  60

Ser Ala Leu Ala Asp Ala Leu Leu Asp Ser Ile Pro Met Val Ala Ile
 65                  70                  75                  80

Thr Gly Gln Val Pro Arg Arg Met Ile Gly Thr Asp Ala Phe Gln Glu
                 85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Ser Thr Glu Ser
                165                 170                 175

Leu Glu Gln Val Leu Arg Leu Val Gly Glu Ser Arg Arg Pro Ile Leu
                180                 185                 190

Tyr Val Gly Gly Gly Cys Ala Ala Ser Gly Glu Glu Leu Arg Arg Phe
            195                 200                 205

Val Glu Leu Thr Gly Ile Pro Val Thr Thr Thr Leu Met Gly Leu Gly
        210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Ile
                245                 250                 255

Ala Phe Gly Val Arg Phe Asp Asp Arg Val Thr Gly Lys Ile Glu Ala
            260                 265                 270

Phe Ala Ser Arg Ser Lys Ile Val His Ile Asp Ile Asp Pro Ala Glu
        275                 280                 285

Ile Gly Lys Asn Lys Gln Pro His Val Ser Ile Cys Ala Asp Val Lys
    290                 295                 300

Leu Ala Leu Gln Gly Leu Asn Ala Leu Leu Asn Gly Ser Lys Ala Gln
305                 310                 315                 320

Gln Gly Leu Asp Phe Gly Pro Trp His Lys Glu Leu Asp Gln Lys
                325                 330                 335

Arg Glu Phe Pro Leu Gly Phe Lys Thr Phe Gly Glu Ala Ile Pro Pro
                340                 345                 350

Gln Tyr Ala Ile Gln Val Leu Asp Glu Leu Thr Lys Gly Glu Ala Ile
            355                 360                 365

Ile Ala Thr Gly Val Gly Gln His Gln Met Trp Ala Ala Gln Tyr Tyr
        370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Ala Gly Ala Ala Val Ala Asn Pro
                405                 410                 415

Gly Val Thr Val Val Asp Ile Asp Gly Asp Gly Ser Phe Leu Met Asn
```

```
                420             425             430
Ile Gln Glu Leu Ala Leu Ile Arg Ile Glu Asn Leu Pro Val Lys Val
            435             440             445

Met Ile Leu Asn Asn Gln His Leu Gly Met Val Val Gln Trp Glu Asp
        450             455             460

Arg Phe Tyr Lys Ala Asn Arg Ala His Thr Tyr Leu Gly Asn Pro Glu
465             470             475             480

Asn Glu Ser Glu Ile Tyr Pro Asp Phe Val Thr Ile Ala Lys Gly Phe
                485             490             495

Asn Val Pro Ala Val Arg Val Thr Lys Lys Ser Glu Val Thr Ala Ala
            500             505             510

Ile Lys Lys Met Leu Glu Thr Pro Gly Pro Tyr Leu Leu Asp Ile Ile
        515             520             525

Val Pro His Gln Glu His Val Leu Pro Met Ile Pro Ser Gly Gly Ala
            530             535             540

Phe Lys Asp Met Ile Met Glu Gly Asp Gly Arg Thr Ser
545             550             555

<210> SEQ ID NO 27
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (644)
<223> OTHER INFORMATION: unknown nucleotide

<400> SEQUENCE: 27 gtc gac gtc ttc gcc tac cct ggc ggc gcg tcc atg gag atc cac cag        48
Val Asp Val Phe Ala Tyr Pro Gly Gly Ala Ser Met Glu Ile His Gln
1               5                  10                  15 gcg ctg acg cgc tcg cca gtc atc acc aac cac ctc ttc cgc cac gag        96
Ala Leu Thr Arg Ser Pro Val Ile Thr Asn His Leu Phe Arg His Glu
                20                  25                  30 cag ggg gag gcc ttc gcg gcg tcc ggg tac gcc cgc gcg tcc ggc cgc       144
Gln Gly Glu Ala Phe Ala Ala Ser Gly Tyr Ala Arg Ala Ser Gly Arg
            35                  40                  45 gtc ggc gtc tgc gtc gcc acc tcc ggc ccg ggg gcc acc aac ctc gtc       192
Val Gly Val Cys Val Ala Thr Ser Gly Pro Gly Ala Thr Asn Leu Val
        50                  55                  60 tcc gcg ctc gcc gac gct ctc ctc gac tcc atc ccc atg gtc gcc atc       240
Ser Ala Leu Ala Asp Ala Leu Leu Asp Ser Ile Pro Met Val Ala Ile
65                  70                  75                  80 acg ggc cag gtc ccc cgc cgc atg atc ggc acg gat gcg ttc cag gag       288
Thr Gly Gln Val Pro Arg Arg Met Ile Gly Thr Asp Ala Phe Gln Glu
                85                  90                  95 acg ccc atc gtg gag gtc acg cgc tcc atc acc aag cac aac tac ctg       336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc       384
Val Leu Asp Val Glu Asp Ile Pro Arg Val Ile Gln Glu Ala Phe Phe
        115                 120                 125 ctc gca tcc tct ggc cgc ccg ggg ccg gtg ctg gtt gat atc ccc aag       432
Leu Ala Ser Ser Gly Arg Pro Gly Pro Val Leu Val Asp Ile Pro Lys
    130                 135                 140 gac atc cag cag cag atg gct gtg cct gtc tgg gac acg ccg atg agt       480
Asp Ile Gln Gln Gln Met Ala Val Pro Val Trp Asp Thr Pro Met Ser
```

-continued

```
      145                 150                 155                 160
ttg cca ggg tac atc gcc cgc ctg ccc aag cca cca tct act gaa tcg        528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg        576
Leu Glu Gln Val Leu Arg Leu Val Gly Glu Ser Arg Arg Pro Ile Leu
                180                 185                 190 tat gtt ggt ggt ggc tgc gct gca tct ggt gag gag ttg cgc cgc ttt        624
Tyr Val Gly Gly Gly Cys Ala Ala Ser Gly Glu Glu Leu Arg Arg Phe
                195                 200                 205 gtt gag ctc act ggg att cna gtt aca act act ctt atg ggc ctt ggc        672
Val Glu Leu Thr Gly Ile Xaa Val Thr Thr Thr Leu Met Gly Leu Gly
                210                 215                 220 aac ttc ccc agt gac gac cca ctg tct ctg cgc atg ctg ggg atg cat        720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ctt        768
Gly Thr Val Tyr Ala Asn Tyr Ala Val Asp Lys Ala Asp Leu Leu Leu
                245                 250                 255 gca ttt ggt gtg cgg ttt gat gat cgt gtg acc ggg aaa atc gag gct        816
Ala Phe Gly Val Arg Phe Asp Asp Arg Val Thr Gly Lys Ile Glu Ala
                260                 265                 270 ttt gca agc agg tcc aag att gtg cac att gac att gac cca gct gag        864
Phe Ala Ser Arg Ser Lys Ile Val His Ile Asp Ile Asp Pro Ala Glu
                275                 280                 285 att ggc aag aac aag cag cca cat gtc tcc att tgt gca gat gtt aag        912
Ile Gly Lys Asn Lys Gln Pro His Val Ser Ile Cys Ala Asp Val Lys
                290                 295                 300 ctt gct tta cag ggg ttg aat gct cta tta aat ggg agc aaa gca caa        960
Leu Ala Leu Gln Gly Leu Asn Ala Leu Leu Asn Gly Ser Lys Ala Gln
305                 310                 315                 320 cag ggt ctg gat ttt ggt cca tgg cac aag gag ttg gat cag cag aag       1008
Gln Gly Leu Asp Phe Gly Pro Trp His Lys Glu Leu Asp Gln Gln Lys
                325                 330                 335 agg gag ttt cct cta gga ttc aag act ttt ggt gag gcc atc ccg ccg       1056
Arg Glu Phe Pro Leu Gly Phe Lys Thr Phe Gly Glu Ala Ile Pro Pro
                340                 345                 350 caa tat gct atc cag gta ctg gat gag ctg aca aaa ggg gag gcg atc       1104
Gln Tyr Ala Ile Gln Val Leu Asp Glu Leu Thr Lys Gly Glu Ala Ile
                355                 360                 365 att gcc acc ggt gtt ggg cag cat cag atg tgg gcg gct cag tat tac       1152
Ile Ala Thr Gly Val Gly Gln His Gln Met Trp Ala Ala Gln Tyr Tyr
                370                 375                 380 act tac aag cgg cca cgg cag tgg ctg tct tca tcc ggt ttg ggt gca       1200
Thr Tyr Lys Arg Pro Arg Gln Trp Leu Ser Ser Ser Gly Leu Gly Ala
385                 390                 395                 400 atg gga ttt ggg ttg cca gct gca gct ggc gct gct gtg gcc aac cca       1248
Met Gly Phe Gly Leu Pro Ala Ala Ala Gly Ala Ala Val Ala Asn Pro
                405                 410                 415 ggt gtt aca gtt gtt gac att gat ggg gat ggt agt ttc ctc atg aac       1296
Gly Val Thr Val Val Asp Ile Asp Gly Asp Gly Ser Phe Leu Met Asn
                420                 425                 430 att cag gag ttg gcg ttg atc cgt att gag aac ctc cca gtg aag gtg       1344
Ile Gln Glu Leu Ala Leu Ile Arg Ile Glu Asn Leu Pro Val Lys Val
                435                 440                 445 atg ata ttg aac aac cag cat ctg gga atg gtg gtg cag tgg gag gat       1392
Met Ile Leu Asn Asn Gln His Leu Gly Met Val Val Gln Trp Glu Asp
                450                 455                 460 agg ttt tac aag gcc aac cgg gcg cac aca tac ctt ggc aac cca gaa       1440
Arg Phe Tyr Lys Ala Asn Arg Ala His Thr Tyr Leu Gly Asn Pro Glu
```

```
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc     1488
Asn Glu Ser Glu Ile Tyr Pro Asp Phe Val Thr Ile Ala Lys Gly Phe
                    485                 490                 495 aac gtt ccg gca gtt cgt gtg acg aag aag agc gaa gtc act gca gca     1536
Asn Val Pro Ala Val Arg Val Thr Lys Lys Ser Glu Val Thr Ala Ala
                500                 505                 510 atc aag aag atg ctt gag acc cca ggg cca tac ttg ttg gat atc att     1584
Ile Lys Lys Met Leu Glu Thr Pro Gly Pro Tyr Leu Leu Asp Ile Ile
            515                 520                 525 gtc ccg cat cag gag cac gtg ctg cct atg atc cca agc ggt ggt gct     1632
Val Pro His Gln Glu His Val Leu Pro Met Ile Pro Ser Gly Gly Ala
        530                 535                 540 ttt aag gac atg atc atg gag ggt gat ggc agg acc tcg tac             1674
Phe Lys Asp Met Ile Met Glu Gly Asp Gly Arg Thr Ser
545                 550                 555
```

<210> SEQ ID NO 28
<211> LENGTH: 557
<212> TYPE: PRT
<213> ORGANISM: Triticum aestivum
<220> FEATURE:
<221> NAME/KEY: MOD_RES
<222> LOCATION: (215)
<223> OTHER INFORMATION: unknown amino acid

<400> SEQUENCE: 28

```
Val Asp Val Phe Ala Tyr Pro Gly Gly Ala Ser Met Glu Ile His Gln
1               5                   10                  15

Ala Leu Thr Arg Ser Pro Val Ile Thr Asn His Leu Phe Arg His Glu
                20                  25                  30

Gln Gly Glu Ala Phe Ala Ala Ser Gly Tyr Ala Arg Ala Ser Gly Arg
            35                  40                  45

Val Gly Val Cys Val Ala Thr Ser Gly Pro Gly Ala Thr Asn Leu Val
        50                  55                  60

Ser Ala Leu Ala Asp Ala Leu Leu Asp Ser Ile Pro Met Val Ala Ile
65                  70                  75                  80

Thr Gly Gln Val Pro Arg Arg Met Ile Gly Thr Asp Ala Phe Gln Glu
                85                  90                  95

Thr Pro Ile Val Glu Val Thr Arg Ser Ile Thr Lys His Asn Tyr Leu
                100                 105                 110

Val Leu Asp Val Glu Asp Ile Pro Arg Val Ile Gln Glu Ala Phe Phe
            115                 120                 125

Leu Ala Ser Ser Gly Arg Pro Gly Pro Val Leu Val Asp Ile Pro Lys
130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
                180                 185                 190

Tyr Val Gly Gly Gly Cys Ala Ala Ser Gly Glu Glu Leu Arg Arg Phe
            195                 200                 205

Val Glu Leu Thr Gly Ile Xaa Val Thr Thr Thr Leu Met Gly Leu Gly
        210                 215                 220

Asn Phe Pro Ser Asp Asp Pro Leu Ser Leu Arg Met Leu Gly Met His
225                 230                 235                 240
```

-continued

```
Gly Thr Val Tyr Ala Asn Tyr Ala Val Asp Lys Ala Asp Leu Leu Leu
                245                 250                 255

Ala Phe Gly Val Arg Phe Asp Asp Arg Val Thr Gly Lys Ile Glu Ala
            260                 265                 270

Phe Ala Ser Arg Ser Lys Ile Val His Ile Asp Ile Asp Pro Ala Glu
        275                 280                 285

Ile Gly Lys Asn Lys Gln Pro His Val Ser Ile Cys Ala Asp Val Lys
    290                 295                 300

Leu Ala Leu Gln Gly Leu Asn Ala Leu Leu Asn Gly Ser Lys Ala Gln
305                 310                 315                 320

Gln Gly Leu Asp Phe Gly Pro Trp His Lys Glu Leu Asp Gln Gln Lys
                325                 330                 335

Arg Glu Phe Pro Leu Gly Phe Lys Thr Phe Gly Glu Ala Ile Pro Pro
            340                 345                 350

Gln Tyr Ala Ile Gln Val Leu Asp Glu Leu Thr Lys Gly Glu Ala Ile
        355                 360                 365

Ile Ala Thr Gly Val Gly Gln His Gln Met Trp Ala Ala Gln Tyr Tyr
    370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Ala Gly Ala Val Ala Asn Pro
                405                 410                 415

Gly Val Thr Val Val Asp Ile Asp Gly Asp Gly Ser Phe Leu Met Asn
            420                 425                 430

Ile Gln Glu Leu Ala Leu Ile Arg Ile Glu Asn Leu Pro Val Lys Val
        435                 440                 445

Met Ile Leu Asn Asn Gln His Leu Gly Met Val Val Gln Trp Glu Asp
    450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
            500                 505                 510

Ile Lys Lys Met Leu Glu Thr Pro Gly Pro Tyr Leu Leu Asp Ile Ile
        515                 520                 525

Val Pro His Gln Glu His Val Leu Pro Met Ile Pro Ser Gly Gly Ala
    530                 535                 540

Phe Lys Asp Met Ile Met Glu Gly Asp Gly Arg Thr Ser
545                 550                 555

<210> SEQ ID NO 29
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (782)
<223> OTHER INFORMATION: unknown nucleotide
<220> FEATURE:
<221> NAME/KEY: modified_base
<222> LOCATION: (800)
<223> OTHER INFORMATION: unknown nucleotide
<220> FEATURE:
<221> NAME/KEY: modified_base
```

-continued

```
<222> LOCATION: (813)
<223> OTHER INFORMATION: unknown nucleotide
<220> FEATURE:
<221> NAME/KEY: modified_base
<222> LOCATION: (839)
<223> OTHER INFORMATION: unknown nucleotide
<220> FEATURE:
<221> NAME/KEY: modified_base
<222> LOCATION: (887)
<223> OTHER INFORMATION: unknown nucleotide
<220> FEATURE:
<221> NAME/KEY: modified_base
<222> LOCATION: (912)
<223> OTHER INFORMATION: unknown nucleotide
<220> FEATURE:
<221> NAME/KEY: modified_base
<222> LOCATION: (936)
<223> OTHER INFORMATION: unknown nucleotide
<220> FEATURE:
<221> NAME/KEY: modified_base
<222> LOCATION: (966)
<223> OTHER INFORMATION: unknown nucleotide
<220> FEATURE:
<221> NAME/KEY: modified_base
<222> LOCATION: (986)
<223> OTHER INFORMATION: unknown nucleotide
<220> FEATURE:
<221> NAME/KEY: modified_base
<222> LOCATION: (1010)
<223> OTHER INFORMATION: unknown nucleotide
<220> FEATURE:
<221> NAME/KEY: modified_base
<222> LOCATION: (1032)
<223> OTHER INFORMATION: unknown nucleotide
<220> FEATURE:
<221> NAME/KEY: modified_base
<222> LOCATION: (1042)
<223> OTHER INFORMATION: unknown nucleotide
<220> FEATURE:
<221> NAME/KEY: modified_base
<222> LOCATION: (1045)
<223> OTHER INFORMATION: unknown nucleotide
<220> FEATURE:
<221> NAME/KEY: modified_base
<222> LOCATION: (1116)
<223> OTHER INFORMATION: unknown nucleotide
<220> FEATURE:
<221> NAME/KEY: modified_base
<222> LOCATION: (1131)
<223> OTHER INFORMATION: unknown nucleotide
<220> FEATURE:
<221> NAME/KEY: modified_base
<222> LOCATION: (1167)
<223> OTHER INFORMATION: unknown nucleotide
<220> FEATURE:
<221> NAME/KEY: modified_base
<222> LOCATION: (1236)
<223> OTHER INFORMATION: unknown nucleotide

<400> SEQUENCE: 29 gtc gac gtc ttc gcc tac cct ggc ggc gcg tcc atg gag atc cac cag      48
Val Asp Val Phe Ala Tyr Pro Gly Gly Ala Ser Met Glu Ile His Gln
 1               5                  10                  15 gcg ctg acg cgc tcg cca gtc atc acc aac cac ctc ttc cgc cac gag      96
Ala Leu Thr Arg Ser Pro Val Ile Thr Asn His Leu Phe Arg His Glu
             20                  25                  30 cag ggg gag gcg ttc gcg gcg tcc ggg tac gcc cgc gcg tcc ggc cgc     144
Gln Gly Glu Ala Phe Ala Ala Ser Gly Tyr Ala Arg Ala Ser Gly Arg
         35                  40                  45 gtc ggc gtc tgc gtc gcc acc tcc ggc ccg ggg gcc acc aac ctc gtc     192
Val Gly Val Cys Val Ala Thr Ser Gly Pro Gly Ala Thr Asn Leu Val
     50                  55                  60 tcc gcg ctc gcc gac gct ctc ctc gac tcc atc ccc atg gtc gcc atc     240
Ser Ala Leu Ala Asp Ala Leu Leu Asp Ser Ile Pro Met Val Ala Ile
 65                  70                  75                  80
```

```
            65                  70                  75                  80
acg ggc cag gtc ccc cgc cgc atg atc ggc acg gat gcg ttc cag gag         288
Thr Gly Gln Val Pro Arg Arg Met Ile Gly Thr Asp Ala Phe Gln Glu
                85                  90                  95 acg ccc atc gtg gag gtc acg cgc tcc atc acc aag cac aac tac ctg         336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc         384
Val Leu Asp Val Glu Asp Ile Pro Arg Val Ile Gln Glu Ala Phe Phe
                115                 120                 125 ctc gca tcc tct ggc cgc ccg ggg ccg gtg ctg gtt gat atc ccc aag         432
Leu Ala Ser Ser Gly Arg Pro Gly Pro Val Leu Val Asp Ile Pro Lys
            130                 135                 140 gac atc cag cag cag atg gct gtg cct gtc tgg gac acg ccg atg agt         480
Asp Ile Gln Gln Gln Met Ala Val Pro Val Trp Asp Thr Pro Met Ser
145                 150                 155                 160 ttg cca ggg tac atc gcc cgc ctg ccc aag cca cca tct act gaa tcg         528
Leu Pro Gly Tyr Ile Ala Arg Leu Pro Lys Pro Pro Ser Thr Glu Ser
                165                 170                 175 ctt gag cag gtc ctg cgt ctg gtt ggc gag tca cgg cgc cca att ctg         576
Leu Glu Gln Val Leu Arg Leu Val Gly Glu Ser Arg Arg Pro Ile Leu
            180                 185                 190 tat gtt ggt ggt ggc tgc gct gca tct ggt gag gag ttg cgc cgc ttt         624
Tyr Val Gly Gly Gly Cys Ala Ala Ser Gly Glu Glu Leu Arg Arg Phe
                195                 200                 205 gtt gag ctc act ggg att cca gtt aca act act ctt atg ggc ctt ggc         672
Val Glu Leu Thr Gly Ile Pro Val Thr Thr Thr Leu Met Gly Leu Gly
            210                 215                 220 aac ttc ccc agt gac gac cca ctg tct ctg cgc atg ctg ggg atg cat         720
Asn Phe Pro Ser Asp Asp Pro Leu Ser Leu Arg Met Leu Gly Met His
225                 230                 235                 240 ggc act gtg tat gca aat tat gca gta gat aag gct gac ctg ttg ctt         768
Gly Thr Val Tyr Ala Asn Tyr Ala Val Asp Lys Ala Asp Leu Leu Leu
                245                 250                 255 gca ttt ggt gtg cng gtt gat gat cgt gtg anc ggg aaa atc gan gct         816
Ala Phe Gly Val Gln Val Asp Asp Arg Val Asn Gly Lys Ile Glu Ala
            260                 265                 270 ttt gca agc agg tcc aag att gng cac att gac att gac cca gct gag         864
Phe Ala Ser Arg Ser Lys Ile Glu His Ile Asp Ile Asp Pro Ala Glu
            275                 280                 285 att ggc aag aac aag cag cca cnt gtc tcc att tgt gca gat gtt aan         912
Ile Gly Lys Asn Lys Gln Pro His Val Ser Ile Cys Ala Asp Val Xaa
            290                 295                 300 ctt gct tta cag ggg ttg aat gcn cta tta aat ggg agc aaa gca caa         960
Leu Ala Leu Gln Gly Leu Asn Ala Leu Leu Asn Gly Ser Lys Ala Gln
305                 310                 315                 320 cag ggn ctg gat ttt ggt cca tgg cnc aag gag ttg gat cag caa aag         1008
Gln Gly Leu Asp Phe Gly Pro Trp His Lys Glu Leu Asp Gln Gln Lys
                325                 330                 335 ang gag ttt cct cta gga ttc aan act ttt ggn gan gcc atc ccg ccg         1056
Lys Glu Phe Pro Leu Gly Phe Lys Thr Phe Gly Glu Ala Ile Pro Pro
            340                 345                 350 cca tat gct atc cag gta ctg gat gag ctg aca aaa ggg gag gcg atc         1104
Pro Tyr Ala Ile Gln Val Leu Asp Glu Leu Thr Lys Gly Glu Ala Ile
            355                 360                 365 att gcc acc ggn gtt ggg cag cat can atg tgg gcg gct cag tat tac         1152
Ile Ala Thr Xaa Val Gly Gln His Thr Met Trp Ala Ala Gln Tyr Tyr
            370                 375                 380 act tac aag cgg ccn cgg cag tgg ctg tct tca tcc ggt ttg ggt gca         1200
```

```
                Thr Tyr Lys Arg Pro Arg Gln Trp Leu Ser Ser Gly Leu Gly Ala
                385                 390                 395                 400 atg gga ttt ggg ttg cca gct gca gct ggc ggc nct gtg gcc aac cca            1248
Met Gly Phe Gly Leu Pro Ala Ala Ala Gly Gly Xaa Val Ala Asn Pro
                        405                 410                 415 ggt gtt aca gtt gtt gac att gat ggg gat ggt agt ttc ctc atg aac            1296
Gly Val Thr Val Val Asp Ile Asp Gly Asp Gly Ser Phe Leu Met Asn
                420                 425                 430 att cag gag ttg gcg ttg atc cgt att gag aac ctc cca gtg aag gtg            1344
Ile Gln Glu Leu Ala Leu Ile Arg Ile Glu Asn Leu Pro Val Lys Val
            435                 440                 445 atg ata ttg aac aac cag cat ctg gga atg gtg gtg cag tgg gag gat            1392
Met Ile Leu Asn Asn Gln His Leu Gly Met Val Val Gln Trp Glu Asp
        450                 455                 460 agg ttt tac aag gcc aac cgg gcg cac aca tac ctt ggc aac cca gaa            1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc            1488
Asn Glu Ser Glu Ile Tyr Pro Asp Phe Val Thr Ile Ala Lys Gly Phe
                485                 490                 495 aac gtt ccg gca gtt cgt gtg acg aag aag agc gaa gtc act gca gca            1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc att            1584
Ile Lys Lys Met Leu Glu Thr Pro Gly Pro Tyr Leu Leu Asp Ile Ile
        515                 520                 525 gtc ccg cat cag gag cac gtg ctg cct atg atc cca agc ggt ggt gct            1632
Val Pro His Gln Glu His Val Leu Pro Met Ile Pro Ser Gly Gly Ala
530                 535                 540 ttt aag gac atg atc atg gag ggt gat ggc agg acc tcg tac                    1674
Phe Lys Asp Met Ile Met Glu Gly Asp Gly Arg Thr Ser
545                 550                 555

<210> SEQ ID NO 30
<211> LENGTH: 557
<212> TYPE: PRT
<213> ORGANISM: Triticum aestivum
<220> FEATURE:
<221> NAME/KEY: MOD_RES
<222> LOCATION: (412)
<223> OTHER INFORMATION: unknown amino acid

<400> SEQUENCE: 30

Val Asp Val Phe Ala Tyr Pro Gly Gly Ala Ser Met Glu Ile His Gln
1               5                   10                  15

Ala Leu Thr Arg Ser Pro Val Ile Thr Asn His Leu Phe Arg His Glu
                20                  25                  30

Gln Gly Glu Ala Phe Ala Ala Ser Gly Tyr Ala Arg Ala Ser Gly Arg
            35                  40                  45

Val Gly Val Cys Val Ala Thr Ser Gly Pro Gly Ala Thr Asn Leu Val
        50                  55                  60

Ser Ala Leu Ala Asp Ala Leu Leu Asp Ser Ile Pro Met Val Ala Ile
65                  70                  75                  80

Thr Gly Gln Val Pro Arg Arg Met Ile Gly Thr Asp Ala Phe Gln Glu
                85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125
```

-continued

Leu Ala Ser Ser Gly Arg Pro Gly Pro Val Leu Val Asp Ile Pro Lys
130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
                180                 185                 190

Tyr Val Gly Gly Cys Ala Ala Ser Gly Glu Glu Leu Arg Arg Phe
        195                 200                 205

Val Glu Leu Thr Gly Ile Pro Val Thr Thr Thr Leu Met Gly Leu Gly
210                 215                 220

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Leu
                245                 250                 255

Ala Phe Gly Val Gln Val Asp Asp Arg Val Asn Gly Lys Ile Glu Ala
                260                 265                 270

Phe Ala Ser Arg Ser Lys Ile Glu His Ile Asp Ile Asp Pro Ala Glu
        275                 280                 285

Ile Gly Lys Asn Lys Gln Pro His Val Ser Ile Cys Ala Asp Val Lys
290                 295                 300

Leu Ala Leu Gln Gly Leu Asn Ala Leu Leu Asn Gly Ser Lys Ala Gln
305                 310                 315                 320

Gln Gly Leu Asp Phe Gly Pro Trp His Lys Glu Leu Asp Gln Gln Lys
                325                 330                 335

Lys Glu Phe Pro Leu Gly Phe Lys Thr Phe Gly Glu Ala Ile Pro Pro
                340                 345                 350

Pro Tyr Ala Ile Gln Val Leu Asp Glu Leu Thr Lys Gly Glu Ala Ile
        355                 360                 365

Ile Ala Thr Xaa Val Gly Gln His Thr Met Trp Ala Ala Gln Tyr Tyr
370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Gly Gly Xaa Val Ala Asn Pro
                405                 410                 415

Gly Val Thr Val Val Asp Ile Asp Gly Asp Gly Ser Phe Leu Met Asn
                420                 425                 430

Ile Gln Glu Leu Ala Leu Ile Arg Ile Glu Asn Leu Pro Val Lys Val
        435                 440                 445

Met Ile Leu Asn Asn Gln His Leu Gly Met Val Val Gln Trp Glu Asp
450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
                500                 505                 510

Ile Lys Lys Met Leu Glu Thr Pro Gly Pro Tyr Leu Leu Asp Ile Ile
        515                 520                 525

Val Pro His Gln Glu His Val Leu Pro Met Ile Pro Ser Gly Gly Ala
530                 535                 540

Phe Lys Asp Met Ile Met Glu Gly Asp Gly Arg Thr Ser

<210> SEQ ID NO 31
<211> LENGTH: 1674
<212> TYPE: DNA
<213> ORGANISM: Triticum aestivum
<220> FEATURE:
<221> NAME/KEY: CDS
<222> LOCATION: (1)..(1671)

<400> SEQUENCE: 31

| | | | | | | | | | | | | | | | |
|---|---|---|---|---|---|---|---|---|---|---|---|---|---|---|---|
| gtc | gac | gtc | ttc | gcc | tac | cct | ggc | ggc | gcg | tcc | atg | gag | atc | cac | cag | 48 |
| Val | Asp | Val | Phe | Ala | Tyr | Pro | Gly | Gly | Ala | Ser | Met | Glu | Ile | His | Gln | |
| 1 | | | | 5 | | | | | 10 | | | | | 15 | | |

| gcg | ctg | acg | cgc | tcg | cca | gtc | atc | acc | aac | cac | ctc | ttc | cgc | cac | gag | 96 |
|---|---|---|---|---|---|---|---|---|---|---|---|---|---|---|---|---|
| Ala | Leu | Thr | Arg | Ser | Pro | Val | Ile | Thr | Asn | His | Leu | Phe | Arg | His | Glu | |
| | | | 20 | | | | | 25 | | | | | 30 | | | |

| cag | ggg | gag | gcg | ttc | gcg | gcg | tcc | ggg | tac | gcc | cgc | gcg | tcc | ggc | cgc | 144 |
|---|---|---|---|---|---|---|---|---|---|---|---|---|---|---|---|---|
| Gln | Gly | Glu | Ala | Phe | Ala | Ala | Ser | Gly | Tyr | Ala | Arg | Ala | Ser | Gly | Arg | |
| | 35 | | | | | 40 | | | | | 45 | | | | | |

| gtc | ggc | gtc | tgc | gtc | gcc | acc | tcc | ggc | ccg | ggg | gcc | acc | aac | ctc | gtc | 192 |
|---|---|---|---|---|---|---|---|---|---|---|---|---|---|---|---|---|
| Val | Gly | Val | Cys | Val | Ala | Thr | Ser | Gly | Pro | Gly | Ala | Thr | Asn | Leu | Val | |
| 50 | | | | | 55 | | | | | 60 | | | | | | |

| tcc | gcg | ctc | gcc | gac | gct | ctc | ctc | gac | tcc | atc | ccc | atg | gtc | gcc | atc | 240 |
|---|---|---|---|---|---|---|---|---|---|---|---|---|---|---|---|---|
| Ser | Ala | Leu | Ala | Asp | Ala | Leu | Leu | Asp | Ser | Ile | Pro | Met | Val | Ala | Ile | |
| 65 | | | | 70 | | | | | 75 | | | | | 80 | | |

| acg | ggc | cag | gtc | ccc | cgc | cgc | atg | atc | ggc | acg | gat | gcg | ttc | cag | gag | 288 |
|---|---|---|---|---|---|---|---|---|---|---|---|---|---|---|---|---|
| Thr | Gly | Gln | Val | Pro | Arg | Arg | Met | Ile | Gly | Thr | Asp | Ala | Phe | Gln | Glu | |
| | | | 85 | | | | | 90 | | | | | 95 | | | |

| acg | ccc | atc | gtg | gag | gtc | acg | cgc | tcc | atc | acc | aag | cac | aac | tac | ctg | 336 |
|---|---|---|---|---|---|---|---|---|---|---|---|---|---|---|---|---|
| Thr | Pro | Ile | Val | Glu | Val | Thr | Arg | Ser | Ile | Thr | Lys | His | Asn | Tyr | Leu | |
| | | 100 | | | | | 105 | | | | | 110 | | | | |

| gtc | ctt | gac | gtg | gag | gat | atc | ccc | cgc | gtc | atc | cag | gaa | gcc | ttc | ttc | 384 |
|---|---|---|---|---|---|---|---|---|---|---|---|---|---|---|---|---|
| Val | Leu | Asp | Val | Glu | Asp | Ile | Pro | Arg | Val | Ile | Gln | Glu | Ala | Phe | Phe | |
| | 115 | | | | | 120 | | | | | 125 | | | | | |

| ctc | gca | tcc | tct | ggc | cgc | ccg | ggg | ccg | gtg | ctg | gtt | gat | atc | ccc | aag | 432 |
|---|---|---|---|---|---|---|---|---|---|---|---|---|---|---|---|---|
| Leu | Ala | Ser | Ser | Gly | Arg | Pro | Gly | Pro | Val | Leu | Val | Asp | Ile | Pro | Lys | |
| | 130 | | | | | 135 | | | | | 140 | | | | | |

| gac | atc | cag | cag | cag | atg | gct | gtg | cct | gtc | tgg | gac | acg | ccg | atg | agt | 480 |
|---|---|---|---|---|---|---|---|---|---|---|---|---|---|---|---|---|
| Asp | Ile | Gln | Gln | Gln | Met | Ala | Val | Pro | Val | Trp | Asp | Thr | Pro | Met | Ser | |
| 145 | | | | | 150 | | | | | 155 | | | | | 160 | |

| ttg | cca | ggg | tac | atc | gcc | cgc | ctg | ccc | aag | cca | cca | tct | act | gaa | tcg | 528 |
|---|---|---|---|---|---|---|---|---|---|---|---|---|---|---|---|---|
| Leu | Pro | Gly | Tyr | Ile | Ala | Arg | Leu | Pro | Lys | Pro | Pro | Ser | Thr | Glu | Ser | |
| | | | | 165 | | | | | 170 | | | | | 175 | | |

| ctt | gag | cag | gtc | ctg | cgt | ctg | gtt | ggc | gag | tca | cgg | cgc | cca | att | ctg | 576 |
|---|---|---|---|---|---|---|---|---|---|---|---|---|---|---|---|---|
| Leu | Glu | Gln | Val | Leu | Arg | Leu | Val | Gly | Glu | Ser | Arg | Arg | Pro | Ile | Leu | |
| | | | 180 | | | | | 185 | | | | | 190 | | | |

| tat | gtt | ggt | ggt | ggc | tgc | gct | gca | tct | ggt | gag | gag | ttg | cgc | cgc | ttt | 624 |
|---|---|---|---|---|---|---|---|---|---|---|---|---|---|---|---|---|
| Tyr | Val | Gly | Gly | Gly | Cys | Ala | Ala | Ser | Gly | Glu | Glu | Leu | Arg | Arg | Phe | |
| | | 195 | | | | | 200 | | | | | 205 | | | | |

| gtt | gag | ctc | act | ggg | att | cca | gtt | aca | act | act | ctt | atg | ggc | ctt | ggc | 672 |
|---|---|---|---|---|---|---|---|---|---|---|---|---|---|---|---|---|
| Val | Glu | Leu | Thr | Gly | Ile | Pro | Val | Thr | Thr | Thr | Leu | Met | Gly | Leu | Gly | |
| | 210 | | | | | 215 | | | | | 220 | | | | | |

| aac | ttc | ccc | agt | gac | gac | cca | ctg | tct | ctg | cgc | atg | ctg | ggg | atg | cat | 720 |
|---|---|---|---|---|---|---|---|---|---|---|---|---|---|---|---|---|
| Asn | Phe | Pro | Ser | Asp | Asp | Pro | Leu | Ser | Leu | Arg | Met | Leu | Gly | Met | His | |
| 225 | | | | | 230 | | | | | 235 | | | | | 240 | |

| ggc | act | gtg | tat | gca | aat | tat | gca | gta | gat | aag | gct | gac | ctg | ttg | ctt | 768 |
|---|---|---|---|---|---|---|---|---|---|---|---|---|---|---|---|---|
| Gly | Thr | Val | Tyr | Ala | Asn | Tyr | Ala | Val | Asp | Lys | Ala | Asp | Leu | Leu | Leu | |
| | | | | 245 | | | | | 250 | | | | | 255 | | |

| gca | ttt | ggt | gtg | cgg | ttt | gat | gat | cgt | gtg | acc | ggg | aaa | atc | gag | gct | 816 |
|---|---|---|---|---|---|---|---|---|---|---|---|---|---|---|---|---|
| Ala | Phe | Gly | Val | Arg | Phe | Asp | Asp | Arg | Val | Thr | Gly | Lys | Ile | Glu | Ala | |

|  |  |  |  |  |  |  |  |  |  |  |  |  |  |  |  |
|---|---|---|---|---|---|---|---|---|---|---|---|---|---|---|---|
|  |  |  | 260 |  |  |  | 265 |  |  |  | 270 |  |  |  |  |
| ttt | gca | agc | agg | tcc | aag | att | gtg | cac | att | gac | att | gac | cca | gct | gag | 864 |
| Phe | Ala | Ser | Arg | Ser | Lys | Ile | Val | His | Ile | Asp | Ile | Asp | Pro | Ala | Glu |  |
|  |  |  | 275 |  |  |  | 280 |  |  |  | 285 |  |  |  |  |  |
| att | ggc | aag | aac | aag | cag | cca | cat | gtc | tcc | att | tgt | gca | gat | gtt | aag | 912 |
| Ile | Gly | Lys | Asn | Lys | Gln | Pro | His | Val | Ser | Ile | Cys | Ala | Asp | Val | Lys |  |
|  | 290 |  |  |  |  | 295 |  |  |  |  | 300 |  |  |  |  |  |
| ctt | gct | tta | cag | ggg | ttg | aat | gct | cta | tta | aat | ggg | agc | aaa | gca | caa | 960 |
| Leu | Ala | Leu | Gln | Gly | Leu | Asn | Ala | Leu | Leu | Asn | Gly | Ser | Lys | Ala | Gln |  |
| 305 |  |  |  |  | 310 |  |  |  |  | 315 |  |  |  |  | 320 |  |
| cag | ggt | ctg | gat | ttt | ggt | cca | tgg | cac | aag | gag | ttg | gat | cag | cag | aag | 1008 |
| Gln | Gly | Leu | Asp | Phe | Gly | Pro | Trp | His | Lys | Glu | Leu | Asp | Gln | Gln | Lys |  |
|  |  |  | 325 |  |  |  | 330 |  |  |  | 335 |  |  |  |  |  |
| agg | gag | ttt | cct | cta | gga | ttc | aag | act | ttt | ggt | gag | gcc | atc | ccg | ccg | 1056 |
| Arg | Glu | Phe | Pro | Leu | Gly | Phe | Lys | Thr | Phe | Gly | Glu | Ala | Ile | Pro | Pro |  |
|  |  |  | 340 |  |  |  | 345 |  |  |  | 350 |  |  |  |  |  |
| caa | tat | gct | atc | cag | gta | ctg | gat | gag | ctg | aca | aaa | ggg | gag | gcg | atc | 1104 |
| Gln | Tyr | Ala | Ile | Gln | Val | Leu | Asp | Glu | Leu | Thr | Lys | Gly | Glu | Ala | Ile |  |
|  |  |  | 355 |  |  |  | 360 |  |  |  | 365 |  |  |  |  |  |
| att | gcc | acc | ggt | gtt | ggg | cag | cat | cag | atg | tgg | gcg | gct | cag | tat | tac | 1152 |
| Ile | Ala | Thr | Gly | Val | Gly | Gln | His | Gln | Met | Trp | Ala | Ala | Gln | Tyr | Tyr |  |
|  | 370 |  |  |  |  | 375 |  |  |  |  | 380 |  |  |  |  |  |
| act | tac | aag | cgg | cca | cgg | cag | tgg | ctg | tct | tca | tcc | ggt | ttg | ggt | gca | 1200 |
| Thr | Tyr | Lys | Arg | Pro | Arg | Gln | Trp | Leu | Ser | Ser | Ser | Gly | Leu | Gly | Ala |  |
| 385 |  |  |  |  | 390 |  |  |  |  | 395 |  |  |  |  | 400 |  |
| atg | gga | ttt | ggg | ttg | cca | gct | gca | gct | ggc | gct | gct | gtg | gcc | aac | cca | 1248 |
| Met | Gly | Phe | Gly | Leu | Pro | Ala | Ala | Ala | Gly | Ala | Ala | Val | Ala | Asn | Pro |  |
|  |  |  |  | 405 |  |  |  |  | 410 |  |  |  |  | 415 |  |  |
| ggt | gtt | aca | gtt | gtt | gac | att | gat | ggg | gat | ggt | agt | ttc | ctc | atg | aac | 1296 |
| Gly | Val | Thr | Val | Val | Asp | Ile | Asp | Gly | Asp | Gly | Ser | Phe | Leu | Met | Asn |  |
|  |  | 420 |  |  |  |  | 425 |  |  |  |  | 430 |  |  |  |  |
| att | cag | gag | ttg | gcg | ttg | atc | cgt | att | gag | aac | ctc | cca | gtg | aag | gtg | 1344 |
| Ile | Gln | Glu | Leu | Ala | Leu | Ile | Arg | Ile | Glu | Asn | Leu | Pro | Val | Lys | Val |  |
|  |  | 435 |  |  |  |  | 440 |  |  |  |  | 445 |  |  |  |  |
| atg | ata | ttg | aac | aac | cag | cat | ctg | gga | atg | gtg | gtg | cag | tgg | gag | gat | 1392 |
| Met | Ile | Leu | Asn | Asn | Gln | His | Leu | Gly | Met | Val | Val | Gln | Trp | Glu | Asp |  |
| 450 |  |  |  |  | 455 |  |  |  |  | 460 |  |  |  |  |  |  |
| agg | ttt | tac | aag | gcc | aac | cgg | gcg | cac | aca | tac | ctt | ggc | aac | cca | gaa | 1440 |
| Arg | Phe | Tyr | Lys | Ala | Asn | Arg | Ala | His | Thr | Tyr | Leu | Gly | Asn | Pro | Glu |  |
| 465 |  |  |  |  | 470 |  |  |  |  | 475 |  |  |  |  | 480 |  |
| aat | gag | agt | gag | ata | tat | cca | gat | ttt | gtg | acg | att | gct | aaa | gga | ttc | 1488 |
| Asn | Glu | Ser | Glu | Ile | Tyr | Pro | Asp | Phe | Val | Thr | Ile | Ala | Lys | Gly | Phe |  |
|  |  |  |  | 485 |  |  |  |  | 490 |  |  |  |  | 495 |  |  |
| aac | gtt | ccg | gca | gtt | cgt | gtg | acg | aag | aag | agc | gaa | gtc | act | gca | gca | 1536 |
| Asn | Val | Pro | Ala | Val | Arg | Val | Thr | Lys | Lys | Ser | Glu | Val | Thr | Ala | Ala |  |
|  |  |  | 500 |  |  |  |  | 505 |  |  |  |  | 510 |  |  |  |
| atc | aag | aag | atg | ctt | gag | acc | cca | ggg | cca | tac | ttg | ttg | gat | atc | att | 1584 |
| Ile | Lys | Lys | Met | Leu | Glu | Thr | Pro | Gly | Pro | Tyr | Leu | Leu | Asp | Ile | Ile |  |
|  |  | 515 |  |  |  |  | 520 |  |  |  |  | 525 |  |  |  |  |
| gtc | ccg | cat | cag | gag | cac | gtg | ctg | cct | atg | atc | cca | aac | ggt | ggt | gct | 1632 |
| Val | Pro | His | Gln | Glu | His | Val | Leu | Pro | Met | Ile | Pro | Asn | Gly | Gly | Ala |  |
|  |  | 530 |  |  |  |  | 535 |  |  |  |  | 540 |  |  |  |  |
| ttt | aag | gac | atg | atc | atg | gag | ggt | gat | ggc | agg | acc | tcg | tac |  |  | 1674 |
| Phe | Lys | Asp | Met | Ile | Met | Glu | Gly | Asp | Gly | Arg | Thr | Ser | Tyr |  |  |  |
| 545 |  |  |  |  | 550 |  |  |  |  | 555 |  |  |  |  |  |  |

<210> SEQ ID NO 32
<211> LENGTH: 557
<212> TYPE: PRT
<213> ORGANISM: Triticum aestivum

<400> SEQUENCE: 32

| Val | Asp | Val | Phe | Ala | Tyr | Pro | Gly | Gly | Ala | Ser | Met | Glu | Ile | His | Gln |
| 1 | | | | 5 | | | | | 10 | | | | | 15 | |

| Ala | Leu | Thr | Arg | Ser | Pro | Val | Ile | Thr | Asn | His | Leu | Phe | Arg | His | Glu |
| | | | 20 | | | | | 25 | | | | | 30 | | |

| Gln | Gly | Glu | Ala | Phe | Ala | Ala | Ser | Gly | Tyr | Ala | Arg | Ala | Ser | Gly | Arg |
| | | 35 | | | | | 40 | | | | | 45 | | | |

| Val | Gly | Val | Cys | Val | Ala | Thr | Ser | Gly | Pro | Gly | Ala | Thr | Asn | Leu | Val |
| | 50 | | | | | 55 | | | | | 60 | | | | |

| Ser | Ala | Leu | Ala | Asp | Ala | Leu | Leu | Asp | Ser | Ile | Pro | Met | Val | Ala | Ile |
| 65 | | | | 70 | | | | | 75 | | | | | 80 | |

| Thr | Gly | Gln | Val | Pro | Arg | Arg | Met | Ile | Gly | Thr | Asp | Ala | Phe | Gln | Glu |
| | | | 85 | | | | | 90 | | | | | 95 | | |

| Thr | Pro | Ile | Val | Glu | Val | Thr | Arg | Ser | Ile | Thr | Lys | His | Asn | Tyr | Leu |
| | | | 100 | | | | | 105 | | | | | 110 | | |

| Val | Leu | Asp | Val | Glu | Asp | Ile | Pro | Arg | Val | Ile | Gln | Glu | Ala | Phe | Phe |
| | | 115 | | | | | 120 | | | | | 125 | | | |

| Leu | Ala | Ser | Ser | Gly | Arg | Pro | Gly | Pro | Val | Leu | Val | Asp | Ile | Pro | Lys |
| | 130 | | | | | 135 | | | | | 140 | | | | |

| Asp | Ile | Gln | Gln | Gln | Met | Ala | Val | Pro | Val | Trp | Asp | Thr | Pro | Met | Ser |
| 145 | | | | 150 | | | | | 155 | | | | | 160 | |

| Leu | Pro | Gly | Tyr | Ile | Ala | Arg | Leu | Pro | Lys | Pro | Pro | Ser | Thr | Glu | Ser |
| | | | 165 | | | | | 170 | | | | | 175 | | |

| Leu | Glu | Gln | Val | Leu | Arg | Leu | Val | Gly | Glu | Ser | Arg | Arg | Pro | Ile | Leu |
| | | 180 | | | | | 185 | | | | | 190 | | | |

| Tyr | Val | Gly | Gly | Gly | Cys | Ala | Ala | Ser | Gly | Glu | Glu | Leu | Arg | Arg | Phe |
| | 195 | | | | | 200 | | | | | 205 | | | | |

| Val | Glu | Leu | Thr | Gly | Ile | Pro | Val | Thr | Thr | Thr | Leu | Met | Gly | Leu | Gly |
| 210 | | | | | 215 | | | | | 220 | | | | | |

| Asn | Phe | Pro | Ser | Asp | Asp | Pro | Leu | Ser | Leu | Arg | Met | Leu | Gly | Met | His |
| 225 | | | | 230 | | | | | 235 | | | | | 240 | |

| Gly | Thr | Val | Tyr | Ala | Asn | Tyr | Ala | Val | Asp | Lys | Ala | Asp | Leu | Leu | Leu |
| | | | 245 | | | | | 250 | | | | | 255 | | |

| Ala | Phe | Gly | Val | Arg | Phe | Asp | Asp | Arg | Val | Thr | Gly | Lys | Ile | Glu | Ala |
| | | | 260 | | | | | 265 | | | | | 270 | | |

| Phe | Ala | Ser | Arg | Ser | Lys | Ile | Val | His | Ile | Asp | Ile | Asp | Pro | Ala | Glu |
| | | 275 | | | | | 280 | | | | | 285 | | | |

| Ile | Gly | Lys | Asn | Lys | Gln | Pro | His | Val | Ser | Ile | Cys | Ala | Asp | Val | Lys |
| | 290 | | | | | 295 | | | | | 300 | | | | |

| Leu | Ala | Leu | Gln | Gly | Leu | Asn | Ala | Leu | Leu | Asn | Gly | Ser | Lys | Ala | Gln |
| 305 | | | | 310 | | | | | 315 | | | | | 320 | |

| Gln | Gly | Leu | Asp | Phe | Gly | Pro | Trp | His | Lys | Glu | Leu | Asp | Gln | Gln | Lys |
| | | | 325 | | | | | 330 | | | | | 335 | | |

| Arg | Glu | Phe | Pro | Leu | Gly | Phe | Lys | Thr | Phe | Gly | Glu | Ala | Ile | Pro | Pro |
| | | | 340 | | | | | 345 | | | | | 350 | | |

| Gln | Tyr | Ala | Ile | Gln | Val | Leu | Asp | Glu | Leu | Thr | Lys | Gly | Glu | Ala | Ile |
| | | 355 | | | | | 360 | | | | | 365 | | | |

| Ile | Ala | Thr | Gly | Val | Gly | Gln | His | Gln | Met | Trp | Ala | Ala | Gln | Tyr | Tyr |
| | 370 | | | | | 375 | | | | | 380 | | | | |

| Thr | Tyr | Lys | Arg | Pro | Arg | Gln | Trp | Leu | Ser | Ser | Gly | Leu | Gly | Ala |
| 385 | | | | 390 | | | | | 395 | | | | | 400 |

| Met | Gly | Phe | Gly | Leu | Pro | Ala | Ala | Ala | Gly | Ala | Ala | Val | Ala | Asn | Pro |

```
                    405                 410                 415
Gly Val Thr Val Val Asp Ile Asp Gly Asp Gly Ser Phe Leu Met Asn
            420                 425                 430

Ile Gln Glu Leu Ala Leu Ile Arg Ile Glu Asn Leu Pro Val Lys Val
        435                 440                 445

Met Ile Leu Asn Asn Gln His Leu Gly Met Val Val Gln Trp Glu Asp
    450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
                485                 490                 495

Asn Val Pro Ala Val Arg Val Thr Lys Lys Ser Glu Val Thr Ala Ala
            500                 505                 510

Ile Lys Lys Met Leu Glu Thr Pro Gly Pro Tyr Leu Leu Asp Ile Ile
        515                 520                 525

Val Pro His Gln Glu His Val Leu Pro Met Ile Pro Asn Gly Gly Ala
    530                 535                 540

Phe Lys Asp Met Ile Met Glu Gly Asp Gly Arg Thr Ser
545                 550                 555

<210> SEQ ID NO 33
<211> LENGTH: 1674
<212> TYPE: DNA
<213> ORGANISM: Triticum aestivum
<220> FEATURE:
<221> NAME/KEY: CDS
<222> LOCATION: (1)..(1671)
<220> FEATURE:
<221> NAME/KEY: modified_base
<222> LOCATION: (723)
<223> OTHER INFORMATION: unknown nucleotide
<220> FEATURE:
<221> NAME/KEY: modified_base
<222> LOCATION: (1089)
<223> OTHER INFORMATION: unknown nucleotide

<400> SEQUENCE: 33 gtc gac gtc ttc gcc tac cct ggc ggc gcg tcc atg gag atc cac cag        48
Val Asp Val Phe Ala Tyr Pro Gly Gly Ala Ser Met Glu Ile His Gln
 1               5                  10                  15 gcg ctg acg cgc tcg cca gtc atc acc aac cac ctc ttc cgc cac gag        96
Ala Leu Thr Arg Ser Pro Val Ile Thr Asn His Leu Phe Arg His Glu
            20                  25                  30 cag ggg gag gcg ttc gcg gcg tcc ggg tac gcc cgc gcg tcc ggc cgc       144
Gln Gly Glu Ala Phe Ala Ala Ser Gly Tyr Ala Arg Ala Ser Gly Arg
        35                  40                  45 gtc ggc gtc tgc gtc gcc acc tcc ggc ccg ggg gcc acc aac ctc gtc       192
Val Gly Val Cys Val Ala Thr Ser Gly Pro Gly Ala Thr Asn Leu Val
    50                  55                  60 tcc gcg ctc gcc gac gct ctc ctc gac tcc atc ccc atg gtc gcc atc       240
Ser Ala Leu Ala Asp Ala Leu Leu Asp Ser Ile Pro Met Val Ala Ile
65                  70                  75                  80 acg ggc cag gtc ccc cgc cgc atg atc ggc acg gat gcg ttc cag gag       288
Thr Gly Gln Val Pro Arg Arg Met Ile Gly Thr Asp Ala Phe Gln Glu
                85                  90                  95 acg ccc atc gtg gag gtc acg cgc tcc atc acc aag cac aac tac ctg       336
Thr Pro Ile Val Glu Val Thr Arg Ser Ile Thr Lys His Asn Tyr Leu
            100                 105                 110 gtc ctt gac gtg gag gat atc ccc cgc gtc atc cag gaa gcc ttc ttc       384
Val Leu Asp Val Glu Asp Ile Pro Arg Val Ile Gln Glu Ala Phe Phe
        115                 120                 125
```

| | | |
|---|---|---|
| ctc gca tcc tct ggc cgc ccg ggg ccg gtg ctg gtt gat atc ccc aag<br>Leu Ala Ser Ser Gly Arg Pro Gly Pro Val Leu Val Asp Ile Pro Lys<br>130                            135                          140 | | 432 |
| gac atc cag cag cag atg gct gtg cct gtc tgg gac acg ccg atg agt<br>Asp Ile Gln Gln Gln Met Ala Val Pro Val Trp Asp Thr Pro Met Ser<br>145                            150                          155                      160 | | 480 |
| ttg cca ggg tac atc gcc cgc ctg ccc aag cca cca tct act gaa tcg<br>Leu Pro Gly Tyr Ile Ala Arg Leu Pro Lys Pro Pro Ser Thr Glu Ser<br>                        165                          170                          175 | | 528 |
| ctt gag cag gtc ctg cgt ctg gtt ggc gag tca cgg cgc cca att ctg<br>Leu Glu Gln Val Leu Arg Leu Val Gly Glu Ser Arg Arg Pro Ile Leu<br>                        180                          185                          190 | | 576 |
| tat gtt ggt ggt ggc tgc gct gca tct ggt gag gag ttg cgc cgc ttt<br>Tyr Val Gly Gly Gly Cys Ala Ala Ser Gly Glu Glu Leu Arg Arg Phe<br>                        195                          200                          205 | | 624 |
| gtt gag ctc act ggg att cca gtt aca act act ctt atg ggc ctt ggc<br>Val Glu Leu Thr Gly Ile Pro Val Thr Thr Thr Leu Met Gly Leu Gly<br>          210                          215                          220 | | 672 |
| aac ttc ccc agt gac gac cca ctg tct ctg cgc atg ctg ggg atg cat<br>Asn Phe Pro Ser Asp Asp Pro Leu Ser Leu Arg Met Leu Gly Met His<br>225                            230                          235                      240 | | 720 |
| ggn act gtg tat gca aat tat gca gta gat aag gct gac ctg ttg ctt<br>Gly Thr Val Tyr Ala Asn Tyr Ala Val Asp Lys Ala Asp Leu Leu Leu<br>                        245                          250                          255 | | 768 |
| gca ttt ggt gtg cgg ttt gat gat cgt gtg acc ggg aaa atc gag gct<br>Ala Phe Gly Val Arg Phe Asp Asp Arg Val Thr Gly Lys Ile Glu Ala<br>                          260                          265                          270 | | 816 |
| ttt gca agc agg tcc aag att gtg cac att gac att gac cca gct gag<br>Phe Ala Ser Arg Ser Lys Ile Val His Ile Asp Ile Asp Pro Ala Glu<br>                  275                          280                          285 | | 864 |
| att ggc aag aac aag cag cca cat gtc tcc att tgt gca gat gtt aag<br>Ile Gly Lys Asn Lys Gln Pro His Val Ser Ile Cys Ala Asp Val Lys<br>          290                          295                          300 | | 912 |
| ctt gct tta cag ggg ttg aat gct cta tta aat ggg agc aaa gca caa<br>Leu Ala Leu Gln Gly Leu Asn Ala Leu Leu Asn Gly Ser Lys Ala Gln<br>305                            310                          315                      320 | | 960 |
| cag ggt ctg gat ttt ggt cca tgg cac aag gag ttg gat cag cag aag<br>Gln Gly Leu Asp Phe Gly Pro Trp His Lys Glu Leu Asp Gln Gln Lys<br>                          325                          330                          335 | | 1008 |
| agg gag ttt cct cta gga ttc aag act ttt ggt gag gcc atc ccg ccg<br>Arg Glu Phe Pro Leu Gly Phe Lys Thr Phe Gly Glu Ala Ile Pro Pro<br>                  340                          345                          350 | | 1056 |
| caa tat gct atc cag gta ctg gat gag ctg acn aaa ggg gag gcg atc<br>Gln Tyr Ala Ile Gln Val Leu Asp Glu Leu Thr Lys Gly Glu Ala Ile<br>                  355                          360                          365 | | 1104 |
| att gcc acc ggt gtt ggg cag cat cag atg tgg gcg gct cag tat tac<br>Ile Ala Thr Gly Val Gly Gln His Gln Met Trp Ala Ala Gln Tyr Tyr<br>          370                          375                          380 | | 1152 |
| act tac aag cgg cca cgg cag tgg ctg tct tca tcc ggt ttg ggt gca<br>Thr Tyr Lys Arg Pro Arg Gln Trp Leu Ser Ser Ser Gly Leu Gly Ala<br>385                            390                          395                      400 | | 1200 |
| atg gga ttt ggg ttg cca gct gca gct ggc gct gct gtg gcc aac cca<br>Met Gly Phe Gly Leu Pro Ala Ala Ala Gly Ala Ala Val Ala Asn Pro<br>                  405                          410                          415 | | 1248 |
| ggt gtt aca gtt gtt gac att gat ggg gat ggt agt ttc ctc atg aac<br>Gly Val Thr Val Val Asp Ile Asp Gly Asp Gly Ser Phe Leu Met Asn<br>          420                          425                          430 | | 1296 |
| att cag gag ttg gcg ttg atc cgt att gag aac ctc cca gtg aag gtg<br>Ile Gln Glu Leu Ala Leu Ile Arg Ile Glu Asn Leu Pro Val Lys Val | | 1344 |

```
atg ata ttg aac aac cag cat ctg gga atg gtg gtg cag tgg gag gat    1392
Met Ile Leu Asn Asn Gln His Leu Gly Met Val Val Gln Trp Glu Asp
450             455                 460 agg ttt tac aag gcc aac cgg gcg cac aca tac ctt ggc aac cca gaa    1440
Arg Phe Tyr Lys Ala Asn Arg Ala His Thr Tyr Leu Gly Asn Pro Glu
465                 470                 475                 480 aat gag agt gag ata tat cca gat ttt gtg acg att gct aaa gga ttc    1488
Asn Glu Ser Glu Ile Tyr Pro Asp Phe Val Thr Ile Ala Lys Gly Phe
                485                 490                 495 aac gtt ccg gca gtt cgt gtg acg aag aag agc gaa gtc act gca gca    1536
Asn Val Pro Ala Val Arg Val Thr Lys Lys Ser Glu Val Thr Ala Ala
            500                 505                 510 atc aag aag atg ctt gag acc cca ggg cca tac ttg ttg gat atc att    1584
Ile Lys Lys Met Leu Glu Thr Pro Gly Pro Tyr Leu Leu Asp Ile Ile
        515                 520                 525 gtc ccg cat cag gag cac gtg ctg cct atg atc cca agc ggt ggt gct    1632
Val Pro His Gln Glu His Val Leu Pro Met Ile Pro Ser Gly Gly Ala
    530                 535                 540 ttt aag gac atg atc atg gag ggt gat ggc agg acc tcg tac            1674
Phe Lys Asp Met Ile Met Glu Gly Asp Gly Arg Thr Ser Tyr
545                 550                 555

<210> SEQ ID NO 34
<211> LENGTH: 557
<212> TYPE: PRT
<213> ORGANISM: Triticum aestivum

<400> SEQUENCE: 34

Val Asp Val Phe Ala Tyr Pro Gly Gly Ala Ser Met Glu Ile His Gln
 1               5                  10                  15

Ala Leu Thr Arg Ser Pro Val Ile Thr Asn His Leu Phe Arg His Glu
            20                  25                  30

Gln Gly Glu Ala Phe Ala Ala Ser Gly Tyr Ala Arg Ala Ser Gly Arg
        35                  40                  45

Val Gly Val Cys Val Ala Thr Ser Gly Pro Gly Ala Thr Asn Leu Val
    50                  55                  60

Ser Ala Leu Ala Asp Ala Leu Leu Asp Ser Ile Pro Met Val Ala Ile
65                  70                  75                  80

Thr Gly Gln Val Pro Arg Arg Met Ile Gly Thr Asp Ala Phe Gln Glu
                85                  90                  95

Thr Pro Ile Val Glu Val Thr Arg Ser Ile Thr Lys His Asn Tyr Leu
            100                 105                 110

Val Leu Asp Val Glu Asp Ile Pro Arg Val Ile Gln Glu Ala Phe Phe
        115                 120                 125

Leu Ala Ser Ser Gly Arg Pro Gly Pro Val Leu Val Asp Ile Pro Lys
    130                 135                 140

Asp Ile Gln Gln Gln Met Ala Val Pro Val Trp Asp Thr Pro Met Ser
145                 150                 155                 160

Leu Pro Gly Tyr Ile Ala Arg Leu Pro Lys Pro Pro Ser Thr Glu Ser
                165                 170                 175

Leu Glu Gln Val Leu Arg Leu Val Gly Glu Ser Arg Arg Pro Ile Leu
            180                 185                 190

Tyr Val Gly Gly Gly Cys Ala Ala Ser Gly Glu Glu Leu Arg Arg Phe
        195                 200                 205

Val Glu Leu Thr Gly Ile Pro Val Thr Thr Thr Leu Met Gly Leu Gly
    210                 215                 220
```

Asn Phe Pro Ser Asp Asp Pro Leu Ser Leu Arg Met Leu Gly Met His
225                 230                 235                 240

Gly Thr Val Tyr Ala Asn Tyr Ala Val Asp Lys Ala Asp Leu Leu Leu
            245                 250                 255

Ala Phe Gly Val Arg Phe Asp Asp Arg Val Thr Gly Lys Ile Glu Ala
        260                 265                 270

Phe Ala Ser Arg Ser Lys Ile Val His Ile Asp Ile Asp Pro Ala Glu
    275                 280                 285

Ile Gly Lys Asn Lys Gln Pro His Val Ser Ile Cys Ala Asp Val Lys
290                 295                 300

Leu Ala Leu Gln Gly Leu Asn Ala Leu Leu Asn Gly Ser Lys Ala Gln
305                 310                 315                 320

Gln Gly Leu Asp Phe Gly Pro Trp His Lys Glu Leu Asp Gln Gln Lys
            325                 330                 335

Arg Glu Phe Pro Leu Gly Phe Lys Thr Phe Gly Glu Ala Ile Pro Pro
        340                 345                 350

Gln Tyr Ala Ile Gln Val Leu Asp Glu Leu Thr Lys Gly Glu Ala Ile
    355                 360                 365

Ile Ala Thr Gly Val Gly Gln His Gln Met Trp Ala Ala Gln Tyr Tyr
370                 375                 380

Thr Tyr Lys Arg Pro Arg Gln Trp Leu Ser Ser Gly Leu Gly Ala
385                 390                 395                 400

Met Gly Phe Gly Leu Pro Ala Ala Gly Ala Val Ala Asn Pro
            405                 410                 415

Gly Val Thr Val Val Asp Ile Asp Gly Asp Gly Ser Phe Leu Met Asn
        420                 425                 430

Ile Gln Glu Leu Ala Leu Ile Arg Ile Glu Asn Leu Pro Val Lys Val
    435                 440                 445

Met Ile Leu Asn Asn Gln His Leu Gly Met Val Val Gln Trp Glu Asp
450                 455                 460

Arg Phe Tyr Lys Ala Asn Arg Ala His Thr Tyr Leu Gly Asn Pro Glu
465                 470                 475                 480

Asn Glu Ser Glu Ile Tyr Pro Asp Phe Val Thr Ile Ala Lys Gly Phe
            485                 490                 495

Asn Val Pro Ala Val Arg Val Thr Lys Lys Ser Glu Val Thr Ala Ala
        500                 505                 510

Ile Lys Lys Met Leu Glu Thr Pro Gly Pro Tyr Leu Leu Asp Ile Ile
    515                 520                 525

Val Pro His Gln Glu His Val Leu Pro Met Ile Pro Ser Gly Gly Ala
530                 535                 540

Phe Lys Asp Met Ile Met Glu Gly Asp Gly Arg Thr Ser
545                 550                 555

<210> SEQ ID NO 35
<211> LENGTH: 1524
<212> TYPE: DNA
<213> ORGANISM: Artificial Sequence
<220> FEATURE:
<223> OTHER INFORMATION: Description of Artificial Sequence: Consensus
      sequence
<220> FEATURE:
<221> NAME/KEY: modified_base
<222> LOCATION: (1125)
<223> OTHER INFORMATION: a, t, c or g

<400> SEQUENCE: 35

-continued

```
gtctgcgtcg ccacctccgg cccggggcc accaacctcg tctccgcgct cgccgacgcc      60
ctcctcgact ccatccccat ggtcgccatc acgggccagg tccccgccg catgatcggc     120
acggacgcgt tccaggagac gcccatagtg gaggtcacgc gctccatcac caagcacaac   180
tacctggtcc ttgacgtgga ggatatcccc cgcgtcatcc aggaagcctt cttcctcgca   240
tcctctggcc gcccggggcc ggtgctggtt gatatcccca aggacatcca gcagcagatg   300
gctgtgcctg tctgggacac gccgatgagt ttgccagggt acatcgcccg cctgcccaag   360
ccaccatcta ctgaatcgct tgagcaggtc ctgcgtctgg ttggcgagtc acggcgccca   420
attctgtatg ttggtggtgg ctgcgctgca tctggcgagg agttgcgccg ctttgttgag   480
ctcactggga ttccagttac aactactctg atgggccttg gcaacttccc cagcgacgac   540
ccactgtctc tgcgcatgct tgggatgcat ggcactgtgt atgcaaatta tgcagtagat   600
aaggctgacc tgttgcttgc atttggtgtg cggtttgatg atcgtgtgac tgggaaaatc   660
gaggcttttg caagcaggtc caagattgtg cacattgaca ttgacccagc tgagattggc   720
aagaacaagc agccacatgt ctccatttgt gcagatgtta agcttgcttt acaggggttg   780
aatgctctat taaatgggag caaagcacaa cagggtctgg attttggtcc atggcacaag   840
gagttggatc agcagaagag ggagtttcct ctaggattca agactttgg cgaggccatc    900
ccgccgcaat atgctatcca ggtactggat gagctgacaa aaggggaggc gatcattgcc   960
actggtgttg ggcagcacca gatgtgggcg gctcagtatt acacttacaa gcggccacgg   1020
cagtggctgt cttcgtctgg tttgggggca atgggatttg ggttaccagc tgcagctggc   1080
gctgctgtgg ccaacccagg tgttacagtt gttgacattg atggngatgg tagtttcctc   1140
atgaacattc aggagttggc gttgatccgt attgagaacc tcccagtgaa ggtgatgata   1200
ttgaacaacc agcatctggg aatggtggtg cagtgggagg ataggtttta caaggccaat   1260
cgggcgcaca catacctgg caacccagaa aatgagagtg agatatatcc agattttgtg   1320
acgattgcta aaggattcaa cgttccggca gttcgtgtga cgaagaagag cgaagtcact   1380
gcagcaatca agaagatgct tgagacccca gggccatact tgttggatat catngtcccg   1440
catcaggagc acgtgctgcc tatgatccca agcggtggtg ctttcaagga catgatcatg   1500
gagggtgatg gcaggacctc gtac                                           1524
```